US009550818B2

(12) United States Patent
Bottaro et al.

(10) Patent No.: US 9,550,818 B2
(45) Date of Patent: Jan. 24, 2017

(54) METHODS FOR USE OF VASCULAR ENDOTHELIAL GROWTH FACTOR ANTAGONISTS

(71) Applicant: The United States of America, as represented by the Secretary, Dept. of Health and Human Services, Washington, DC (US)

(72) Inventors: Donald P. Bottaro, Rockville, MD (US); Fabiola Cecchi, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 45 days.

(21) Appl. No.: 14/397,435

(22) PCT Filed: Apr. 26, 2013

(86) PCT No.: PCT/US2013/038506

§ 371 (c)(1),
(2) Date: Oct. 27, 2014

(87) PCT Pub. No.: WO2013/163606

PCT Pub. Date: Oct. 31, 2013

(65) Prior Publication Data

US 2015/0126446 A1 May 7, 2015

Related U.S. Application Data

(60) Provisional application No. 61/639,230, filed on Apr. 27, 2012.

(51) Int. Cl.

*A61K 38/18* (2006.01)
*C07K 14/475* (2006.01)
*C07K 14/52* (2006.01)
*C07K 14/71* (2006.01)

(52) U.S. Cl.

CPC ......... *C07K 14/475* (2013.01); *A61K 38/1866* (2013.01); *C07K 14/52* (2013.01); *C07K 14/71* (2013.01)

(58) Field of Classification Search

None

See application file for complete search history.

(56) References Cited

FOREIGN PATENT DOCUMENTS

WO WO 2006/119035 11/2006
WO WO 2007/044534 4/2007

OTHER PUBLICATIONS

Cecchi et al. (2012) Cancer Cell 22:250-262 "Targeted Disruption of Heparan Sulfate Interaction with Hepatocyte and Vascular Endothelial Growth Factors Blocks Normal and Oncogenic Signaling".

Grënwald et al. (2010) Biochimica et Biophysica Acta 1804:567-580 "Structure-function analysis of VEGF receptor activation and the role of coreceptors in angiogenic signaling".

International Search Report and Written Opinion for PCT/US2013/038506 dated Aug. 13, 2013.

Krilleke et al. (2007) J. Biol. Chem. 282:28045-28056 "Molecular Mapping and Functional Characterization of the VEGF164 Heparin-binding Domain".

*Primary Examiner* — Christine J Saoud

(74) *Attorney, Agent, or Firm* — Swanson & Bratschun, L.L.C.

(57) ABSTRACT

The present invention provides variant VEGF polypeptides which have been altered in their C-terminal heparin binding region to lower their heparin binding affinity. These variants have been found to act as receptor antagonists for VEGF receptors and antagonize angiogenesis. These variants are useful to treat diseases characterized by pathological angiogenesis.

6 Claims, 14 Drawing Sheets

Figure 1A signal peptide: 1-26 ▶ mature peptide

| Position | Sequence | | Accession | Species |
|---|---|---|---|---|
| 1 | MNFLLSWVHWSLALLLYLHHAKWSQAAPMAE-GGGQNHHEVVKFMDVYQRSYCHPIETLVDIFQEYPDEIEYIFKPSCVP | 79 | NP_001165097 | H sapiens (Human) |
| 1 | MNFLLSWVHWSLALLLYLHHAKWSQAAPMA--DGEHKPHEVVKFMDVYQRSYCRPIETLVDIFQEYPDEIEYIFKPSCVP | 78 | NP_001009854 | F catus (Cat) |
| 1 | MNFLLSWVHWSLALLLYLHHAKWSQAAPMA--GGEHKPHEVVKFMDVYQRSYCRPIETLVDIFQEYPDEIEYIFKPSCVP | 78 | NP_001103972 | C familiaris (Dog) |
| 1 | MNFLLSWVHWSLALLLYLHHAKWSQAAPMA--EGGQKPHEVVKFMDVYQRSFCRPIETLVDIFQEYPDEIEFIFKPSCVP | 78 | NP_776641 | B Taurus (Bovine) |
| 1 | MNFLLSWVHWSLALLLYLHHAKWSQAAPMA--EGEHKTHEVVKFMDVYQRSYCRPIETLVDIFQEYPDEIEYIFKPSCVP | 78 | NP_001075290 | E caballus (Horse) |
| 1 | MNFLLSWVHWTLALLLYLHHAKWSQAAPTT--EGEQKAHEVVKFMDVYQRSYCRPIETLVDIFQEYPDEIEYIFKPSCVP | 78 | EDM18778 | R norvegicus (Rat) |
| 1 | MNFLLSWVHWTLALLLYLHHAKWSQAAPTT--EGEQKSHEVIKFMDVYQRSYCRPIETLVDIFQEYPDEIEYIFKPSCVP | 78 | AAH61468 | M musculus (Mouse) |
| 1 | MNFLLTWIHWGLAALLYLQSAELSKAAPAL-GDGERKPNEVIKFLEVYERSFCRTIETLVDIFQEYPDEVEYIFRPSCVP | 79 | NP_001103825 | G gallus (Chicken) |
| 1 | MNFLPSWIHWGLAVLLYIPLAQLSGAAPMP-GEGDHKPTEVVKFLKVYERSMCQVREILVDIFQEYPEEVEYIFKPSCVP | 79 | NP_001091254 | X laevis (Frog) |
| 80 | LMRCGGCCNDEGLECVPTEESNITMQIMRIKPHQGQHIGEMSFLQHNKCECRPKKD-RARQENPCGPCSER--RKHLFVQ | 156 | NP_001165097 | H sapiens (Human) |
| 79 | LMRCGGCCNDEGLECVPTEEFNITMQIMRIKPHQGQHIGEMSFLQHSKCECRPKKD-RAK-ENPCGPCSER--RKHLFVQ | 154 | NP_001009854 | F catus (Cat) |
| 79 | LMRCGGCCNDEGLECVPTEEFNITMQIMRIKPHQGQHIGEMSFLQHSKCECRPKKD-RARQENPCGPCSER--RKHLFVQ | 155 | NP_001103972 | C familiaris (Dog) |
| 79 | LMRCGGCCNDESLECVPTEEFNITMQIMRIKPHQSQHIGEMSFLQHNKCECRPKKD-KARQENPCGPCSER--RKHLFVQ | 155 | NP_776641 | B Taurus (Bovine) |
| 79 | LMRCGGCCNDEGLECVPTAEFNITMQIMRIKPHQSQHIGEMSFLQHSKCECRPKKD-KARQENPCGPCSER--RKHLFVQ | 155 | NP_001075290 | E caballus (Horse) |
| 79 | LMRCAGCCNDEALECVPTSESNVTMQIMRIKPHQSQHIGEMSFLQHSRCECRPKKD-RTKPENHCEPCSER--RKHLFVQ | 155 | EDM18778 | R norvegicus (Rat) |
| 79 | LMRCAGCCNDEALECVPTSESNITMQIMRIKPHQSQHIGEMSFLQHSRCECRPKKD-RTKPENHCEPCSER--RKHLFVQ | 155 | AAH61468 | M musculus (Mouse) |
| 80 | LMRCAGCCGDEGLECVPVDVYNVTMEIARIKPHQSQHIAHMSFLQHSKCDCRPKKDVKNKQENHCEPCSER--RKHLFVQ | 157 | NP_001103825 | G gallus (Chicken) |
| 80 | LMRCAGCCNDESLECVSTESYNITMQIMKIKPHISQHIMDMSFQQHSHCECRPKKEVKIKQENHCEPCTEKSQRKHLFVQ | 159 | NP_001091254 | X laevis (Frog) |
| 157 | DPQTCKCSCKNTDSRCKARQLELNERTCRCDKPRR | 191 SEQ ID NO:2 | NP_001165097 | H sapiens (Human) |
| 155 | DPQTCKCSCKNTDSRCKARQLELNERTCRCDKPRR | 189 SEQ ID NO:39 | NP_001009854 | F catus (Cat) |
| 156 | DPQTCKCSCKNTDSRCKARQLELNERTCRCDKPRR | 190 SEQ ID NO:40 | NP_001103972 | C familiaris (Dog) |
| 156 | DPQTCKCSCKNTDSRCKARQLELNERTCRCDKPRR | 190 SEQ ID NO:41 | NP_776641 | B Taurus (Bovine) |
| 156 | DPQTCKCSCKNTDSRCKARQLELNERTCRCDKPRR | 190 SEQ ID NO:42 | NP_001075290 | E caballus (Horse) |
| 156 | DPQTCKCSCKNTDSRCKARQLELNERTCRCDKPRR | 190 SEQ ID NO:43 | EDM18778 | R norvegicus (Rat) |
| 156 | DPQTCKCSCKNTDSRCKARQLELNERTCRCDKPRR | 190 SEQ ID NO:44 | AAH61468 | M musculus (Mouse) |
| 158 | DPQTCKCSCKFTDSRCKSRQLELNERTCRCEKPRR | 192 SEQ ID NO:45 | NP_001103825 | G gallus (Chicken) |
| 160 | DPQTCKCSCKNTDSRCKTRQLELNERTCRCEKPRR | 194 SEQ ID NO:46 | NP_001091254 | X laevis (Frog) |

heparin binding domain heparin binding domain

VEGF165
HS binding domain

```
CLUSTAL W (1.83) multiple sequence alignment: all hVEGFA isoforms
GROUP 1
NP_001165097.1          ------------------------------------------------------------
NP_001165100.1          ------------------------------------------------------------
NP_001028928.1          MTDRQTDTAPSPSYHLLPGRRRTVDAAASRGQGPEPAPGGGVEGVGARGVALKLFVQLLG
NP_001020539.2          MTDRQTDTAPSPSYHLLPGRRRTVDAAASRGQGPEPAPGGGVEGVGARGVALKLFVQLLG
BAG70265.1              ------------------------------------------------------------
BAG70136.1              ------------------------------------------------------------
GROUP 2
NP_001020538.2          MTDRQTDTAPSPSYHLLPGRRRTVDAAASRGQGPEPAPGGGVEGVGARGVALKLFVQLLG
NP_001165096.1          ------------------------------------------------------------
NP_001165095.1          ------------------------------------------------------------
NP_003367.4             MTDRQTDTAPSPSYHLLPGRRRTVDAAASRGQGPEPAPGGGVEGVGARGVALKLFVQLLG
NP_001020537.2          MTDRQTDTAPSPSYHLLPGRRRTVDAAASRGQGPEPAPGGGVEGVGARGVALKLFVQLLG
P15692.2                ------------------------------------------------------------
NP_001165094.1          ------------------------------------------------------------


GROUP 1
NP_001165097.1          ------------------------------------------------------------
NP_001165100.1          ------------------------------------------------------------
NP_001028928.1          CSRFGGAVVRAGEAEPSGAARSASSGREEPQPEEGEEEEEKEEERGPQWRLGARKPGSWT
NP_001020539.2          CSRFGGAVVRAGEAEPSGAARSASSGREEPQPEEGEEEEEKEEERGPQWRLGARKPGSWT
BAG70265.1              ------------------------------------------------------------
BAG70136.1              ------------------------------------------------------------
GROUP 2
NP_001020538.2          CSRFGGAVVRAGEAEPSGAARSASSGREEPQPEEGEEEEEKEEERGPQWRLGARKPGSWT
NP_001165096.1          ------------------------------------------------------------
NP_001165095.1          ------------------------------------------------------------
NP_003367.4             CSRFGGAVVRAGEAEPSGAARSASSGREEPQPEEGEEEEEKEEERGPQWRLGARKPGSWT
NP_001020537.2          CSRFGGAVVRAGEAEPSGAARSASSGREEPQPEEGEEEEEKEEERGPQWRLGARKPGSWT
P15692.2                ------------------------------------------------------------
NP_001165094.1          ------------------------------------------------------------
```

FIGURE 6

```
GROUP 1
NP_001165097.1      ------------------------------------------------------------
NP_001165100.1      ------------------------------------------------------------
NP_001028928.1      GEAAVCADSAPAARAPQALARASGRGGRVARRGAEESGPPHSPSRRGSASRAGPGRASET
NP_001020539.2      GEAAVCADSAPAARAPQALARASGRGGRVARRGAEESGPPHSPSRRGSASRAGPGRASET
BAG70265.1          ------------------------------------------------------------
BAG70136.1          ------------------------------------------------------------
GROUP 2
NP_001020538.2      GEAAVCADSAPAARAPQALARASGRGGRVARRGAEESGPPHSPSRRGSASRAGPGRASET
NP_001165096.1      ------------------------------------------------------------
NP_001165095.1      ------------------------------------------------------------
NP_003367.4         GEAAVCADSAPAARAPQALARASGRGGRVARRGAEESGPPHSPSRRGSASRAGPGRASET
NP_001020537.2      GEAAVCADSAPAARAPQALARASGRGGRVARRGAEESGPPHSPSRRGSASRAGPGRASET
P15692.2            ------------------------------------------------------------
NP_001165094.1      ------------------------------------------------------------

GROUP 1
NP_001165097.1      MNFLLSWVHWSLALLLYLHHAKWSQAAPMAEGGGQNHHEVVKFMDVYQRSYCHPIETLVD
NP_001165100.1      MNFLLSWVHWSLALLLYLHHAKWSQAAPMAEGGGQNHHEVVKFMDVYQRSYCHPIETLVD
NP_001028928.1      MNFLLSWVHWSLALLLYLHHAKWSQAAPMAEGGGQNHHEVVKFMDVYQRSYCHPIETLVD
NP_001020539.2      MNFLLSWVHWSLALLLYLHHAKWSQAAPMAEGGGQNHHEVVKFMDVYQRSYCHPIETLVD
BAG70265.1          MNFLLSWVHWSLALLLYLHHAKWSQAAPMAEGGGQNHHEVVKFMDVYQRSYCHPIETLVD
BAG70136.1          MNFLLSWVHWSLALLLYLHHAKWSQAAPMAEGGGQNHHEVVKFMDVYQRSYCHPIETLVD
GROUP 2
NP_001020538.2      MNFLLSWVHWSLALLLYLHHAKWSQAAPMAEGGGQNHHEVVKFMDVYQRSYCHPIETLVD
NP_001165096.1      MNFLLSWVHWSLALLLYLHHAKWSQAAPMAEGGGQNHHEVVKFMDVYQRSYCHPIETLVD
NP_001165095.1      MNFLLSWVHWSLALLLYLHHAKWSQAAPMAEGGGQNHHEVVKFMDVYQRSYCHPIETLVD
NP_003367.4         MNFLLSWVHWSLALLLYLHHAKWSQAAPMAEGGGQNHHEVVKFMDVYQRSYCHPIETLVD
NP_001020537.2      MNFLLSWVHWSLALLLYLHHAKWSQAAPMAEGGGQNHHEVVKFMDVYQRSYCHPIETLVD
P15692.2            MNFLLSWVHWSLALLLYLHHAKWSQAAPMAEGGGQNHHEVVKFMDVYQRSYCHPIETLVD
NP_001165094.1      MNFLLSWVHWSLALLLYLHHAKWSQAAPMAEGGGQNHHEVVKFMDVYQRSYCHPIETLVD
                    ************************************************************
```

FIGURE 6 (continued)

```
GROUP 1
NP_001165097.1        IFQEYPDEIEYIFKPSCVPLMRCGGCCNDEGLECVPTEESNITMQIMRIKPHQGQHIGEM
NP_001165100.1        IFQEYPDEIEYIFKPSCVPLMRCGGCCNDEGLECVPTEESNITMQIMRIKPHQGQHIGEM
NP_001028928.1        IFQEYPDEIEYIFKPSCVPLMRCGGCCNDEGLECVPTEESNITMQIMRIKPHQGQHIGEM
NP_001020539.2        IFQEYPDEIEYIFKPSCVPLMRCGGCCNDEGLECVPTEESNITMQIMRIKPHQGQHIGEM
BAG70265.1            IFQEYPDEIEYIFKPSCVPLMRCGGCCNDEGLECVPTEESNITMQIMRIKPHQGQHIGEM
BAG70136.1            IFQEYPDEIEYIFKPSCVPLMRCGGCCNDEGLECVPTEESNITMQIMRIKPHQGQHIGEM
GROUP 2
NP_001020538.2        IFQEYPDEIEYIFKPSCVPLMRCGGCCNDEGLECVPTEESNITMQIMRIKPHQGQHIGEM
NP_001165096.1        IFQEYPDEIEYIFKPSCVPLMRCGGCCNDEGLECVPTEESNITMQIMRIKPHQGQHIGEM
NP_001165095.1        IFQEYPDEIEYIFKPSCVPLMRCGGCCNDEGLECVPTEESNITMQIMRIKPHQGQHIGEM
NP_003367.4           IFQEYPDEIEYIFKPSCVPLMRCGGCCNDEGLECVPTEESNITMQIMRIKPHQGQHIGEM
NP_001020537.2        IFQEYPDEIEYIFKPSCVPLMRCGGCCNDEGLECVPTEESNITMQIMRIKPHQGQHIGEM
P15692.2              IFQEYPDEIEYIFKPSCVPLMRCGGCCNDEGLECVPTEESNITMQIMRIKPHQGQHIGEM
NP_001165094.1        IFQEYPDEIEYIFKPSCVPLMRCGGCCNDEGLECVPTEESNITMQIMRIKPHQGQHIGEM
                      ************************************************************

                                     HBD1->
GROUP 1
NP_001165097.1        SFLQHNKCECRPKKDRARQE------------------N---------------------
NP_001165100.1        SFLQHNKCECRPKKDRARQE------------------N---------------------
NP_001028928.1        SFLQHNKCECRPKKDRARQE------------------N---------------------
NP_001020539.2        SFLQHNKCECRPKKDRARQE------------------N---------------------
BAG70265.1            SFLQHNKCECRPKKDRARQE------------------N---------------------
BAG70136.1            SFLQHNKCECRPKKDRARQE------------------N---------------------
GROUP 2
NP_001020538.2        SFLQHNKCECRPKKDRARQEKKSVRGKGKGQKRKRKKSR---------------------
NP_001165096.1        SFLQHNKCECRPKKDRARQEKKSVRGKGKGQKRKRKKSR---------------------
NP_001165095.1        SFLQHNKCECRPKKDRARQEKKSVRGKGKGQKRKRKKSRYKSWSV---------------
NP_003367.4           SFLQHNKCECRPKKDRARQEKKSVRGKGKGQKRKRKKSRYKSWSV---------------
NP_001020537.2        SFLQHNKCECRPKKDRARQEKKSVRGKGKGQKRKRKKSRYKSWSVYVGARCCLMPWSLPG
P15692.2              SFLQHNKCECRPKKDRARQEKKSVRGKGKGQKRKRKKSRYKSWSVYVGARCCLMPWSLPG
NP_001165094.1        SFLQHNKCECRPKKDRARQEKKSVRGKGKGQKRKRKKSRYKSWSVYVGARCCLMPWSLPG
                      ********************
```

FIGURE 6 (continued)

```
                             13   14                                 49
                              \   /                                   |
GROUP 1               HBD6     **                                     *
NP_001165097.1        --PCGPCSERRKHLFVQDPQTCKCSCKNTDSRCKARQLELNERTCRCDKPRR-
NP_001165100.1        --PCGPCSERRKHLFVQDPQTCKCSCKNTDSRCKARQLELNERTCR-SLTRKD
NP_001028928.1        --PCGPCSERRKHLFVQDPQTCKCSCKNTDSRCKARQLELNERTCR-SLTRKD
NP_001020539.2        --PCGPCSERRKHLFVQDPQTCKCSCKNTDSRCKARQLELNERTCRCDKPRR-
BAG70265.1            --PCGPCSERRKHLFVQDPQTCKCSCKNTDSRCKARQLELNERTCRCDKPRR-
BAG70136.1            --PCGPCSERRKHLFVQDPQTCKCSCKNTDSRCKARQLELNERTCRCDKPRR-
GROUP 2
NP_001020538.2        --PCGPCSERRKHLFVQDPQTCKCSCKNTDSRCKARQLELNERTCRCDKPRR-   31,32,67
NP_001165096.1        --PCGPCSERRKHLFVQDPQTCKCSCKNTDSRCKARQLELNERTCRCDKPRR-   31,32,67
NP_001165095.1        --PCGPCSERRKHLFVQDPQTCKCSCKNTDSRCKARQLELNERTCRCDKPRR-   37,38,73
NP_003367.4           --PCGPCSERRKHLFVQDPQTCKCSCKNTDSRCKARQLELNERTCRCDKPRR-   37,38,73
NP_001020537.2        PHPCGPCSERRKHLFVQDPQTCKCSCKNTDSRCKARQLELNERTCRCDKPRR-   54,55,90
P15692.2              PHPCGPCSERRKHLFVQDPQTCKCSCKNTDSRCKARQLELNERTCRCDKPRR-   54,55,90
NP_001165094.1        PHPCGPCSERRKHLFVQDPQTCKCSCKNTDSRCKARQLELNERTCRCDKPRR-   54,55,90
                        ********************************************    *
```

FIGURE 6 (continued)

SEQUENCE LISTING

```
<160> NUMBER OF SEQ ID NOS: 69

<210> SEQ ID NO 1
<211> LENGTH: 576
<212> TYPE: DNA
<213> ORGANISM: Homo sapiens
<220> FEATURE:
<221> NAME/KEY: CDS
<222> LOCATION: (1)..(576)

<400> SEQUENCE: 1

atg aac ttt ctg ctg agc tgg gtg cac tgg tcc ctg gcc ctg ctg ctg       48
Met Asn Phe Leu Leu Ser Trp Val His Trp Ser Leu Ala Leu Leu Leu
1               5                   10                  15

tac ctg cac cac gcc aag tgg tcc cag gcc gct cct atg gcc gag ggc       96
Tyr Leu His His Ala Lys Trp Ser Gln Ala Ala Pro Met Ala Glu Gly
            20                  25                  30

gga ggc cag aac cac cac gag gtg gtg aaa ttc atg gac gtg tac cag      144
Gly Gly Gln Asn His His Glu Val Val Lys Phe Met Asp Val Tyr Gln
```

```
        35                  40                  45

cgg agc tac tgc cac ccc atc gag aca ctg gtg gac atc ttc cag gaa      192
Arg Ser Tyr Cys His Pro Ile Glu Thr Leu Val Asp Ile Phe Gln Glu
    50                  55                  60

tac ccc gac gag atc gag tac atc ttc aag ccc agc tgc gtg ccc ctg      240
Tyr Pro Asp Glu Ile Glu Tyr Ile Phe Lys Pro Ser Cys Val Pro Leu
65                  70                  75                  80

atg aga tgc ggc ggc tgc tgc aac gac gag ggc ctg gaa tgc gtg ccc      288
Met Arg Cys Gly Gly Cys Cys Asn Asp Glu Gly Leu Glu Cys Val Pro
                85                  90                  95

acc gag gaa tcc aac atc acc atg cag atc atg cgg atc aag ccc cac      336
Thr Glu Glu Ser Asn Ile Thr Met Gln Ile Met Arg Ile Lys Pro His
            100                 105                 110

cag ggc cag cat atc ggc gag atg agc ttc ctg cag cac aac aag tgc      384
Gln Gly Gln His Ile Gly Glu Met Ser Phe Leu Gln His Asn Lys Cys
        115                 120                 125

gag tgc cgg ccc aag aag gac cgg gcc aga cag gaa aac ccc tgc ggc      432
Glu Cys Arg Pro Lys Lys Asp Arg Ala Arg Gln Glu Asn Pro Cys Gly
    130                 135                 140

ccc tgc agc gag cgg aga aag cac ctg ttc gtg cag gac ccc cag acc      480
Pro Cys Ser Glu Arg Arg Lys His Leu Phe Val Gln Asp Pro Gln Thr
145                 150                 155                 160

tgc aag tgc tcc tgc aag aac acc gac agc cgg tgc aag gcc cgg cag      528
Cys Lys Cys Ser Cys Lys Asn Thr Asp Ser Arg Cys Lys Ala Arg Gln
                165                 170                 175

ctg gaa ctg aac gag cgg acc tgc aga tgc gac aag ccc aga cgg taa      576
Leu Glu Leu Asn Glu Arg Thr Cys Arg Cys Asp Lys Pro Arg Arg
            180                 185                 190


<210> SEQ ID NO 2
<211> LENGTH: 191
<212> TYPE: PRT
<213> ORGANISM: Homo sapiens

<400> SEQUENCE: 2

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175
```

```
Leu Glu Leu Asn Glu Arg Thr Cys Arg Cys Asp Lys Pro Arg Arg
            180                 185                 190


<210> SEQ ID NO 3
<211> LENGTH: 165
<212> TYPE: PRT
<213> ORGANISM: Homo sapiens

<400> SEQUENCE: 3

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Arg Cys
145                 150                 155                 160

Asp Lys Pro Arg Arg
                165


<210> SEQ ID NO 4
<211> LENGTH: 55
<212> TYPE: PRT
<213> ORGANISM: Homo sapiens

<400> SEQUENCE: 4

Ala Arg Gln Glu Asn Pro Cys Gly Pro Cys Ser Glu Arg Arg Lys His
1               5                   10                  15

Leu Phe Val Gln Asp Pro Gln Thr Cys Lys Cys Ser Cys Lys Asn Thr
            20                  25                  30

Asp Ser Arg Cys Lys Ala Arg Gln Leu Glu Leu Asn Glu Arg Thr Cys
        35                  40                  45

Arg Cys Asp Lys Pro Arg Arg
    50                  55


<210> SEQ ID NO 5
<211> LENGTH: 576
<212> TYPE: DNA
<213> ORGANISM: Homo sapiens
<220> FEATURE:
<221> NAME/KEY: CDS
<222> LOCATION: (1)..(576)

<400> SEQUENCE: 5

atg aac ttt ctg ctg agc tgg gtg cac tgg tcc ctg gcc ctg ctg ctg       48
Met Asn Phe Leu Leu Ser Trp Val His Trp Ser Leu Ala Leu Leu Leu
1               5                   10                  15
```

-continued

```
tac ctg cac cac gcc aag tgg tcc cag gcc gct cct atg gcc gag ggc        96
Tyr Leu His His Ala Lys Trp Ser Gln Ala Ala Pro Met Ala Glu Gly
            20                  25                  30

gga ggc cag aac cac cac gag gtg gtg aaa ttc atg gac gtg tac cag       144
Gly Gly Gln Asn His His Glu Val Val Lys Phe Met Asp Val Tyr Gln
        35                  40                  45

cgg agc tac tgc cac ccc atc gag aca ctg gtg gac atc ttc cag gaa       192
Arg Ser Tyr Cys His Pro Ile Glu Thr Leu Val Asp Ile Phe Gln Glu
    50                  55                  60

tac ccc gac gag atc gag tac atc ttc aag ccc agc tgc gtg ccc ctg       240
Tyr Pro Asp Glu Ile Glu Tyr Ile Phe Lys Pro Ser Cys Val Pro Leu
65                  70                  75                  80

atg aga tgc ggc ggc tgc tgc aac gac gag ggc ctg gaa tgc gtg ccc       288
Met Arg Cys Gly Gly Cys Cys Asn Asp Glu Gly Leu Glu Cys Val Pro
                85                  90                  95

acc gag gaa tcc aac atc acc atg cag atc atg cgg atc aag ccc cac       336
Thr Glu Glu Ser Asn Ile Thr Met Gln Ile Met Arg Ile Lys Pro His
            100                 105                 110

cag ggc cag cat atc ggc gag atg agc ttc ctg cag cac aac aag tgc       384
Gln Gly Gln His Ile Gly Glu Met Ser Phe Leu Gln His Asn Lys Cys
        115                 120                 125

gag tgc cgg ccc aag aag gac cgg gcc aga cag gaa aac ccc tgc ggc       432
Glu Cys Arg Pro Lys Lys Asp Arg Ala Arg Gln Glu Asn Pro Cys Gly
    130                 135                 140

ccc tgc agc gag gag gaa aag cac ctg ttc gtg cag gac ccc cag acc       480
Pro Cys Ser Glu Glu Glu Lys His Leu Phe Val Gln Asp Pro Gln Thr
145                 150                 155                 160

tgc aag tgc tcc tgc aag aac acc gac agc cgg tgc aag gcc cgg cag       528
Cys Lys Cys Ser Cys Lys Asn Thr Asp Ser Arg Cys Lys Ala Arg Gln
                165                 170                 175

ctg gaa ctg aac gag cgg acc tgc gaa tgc gac aag ccc aga cgg taa       576
Leu Glu Leu Asn Glu Arg Thr Cys Glu Cys Asp Lys Pro Arg Arg
            180                 185                 190
```

<210> SEQ ID NO 6
<211> LENGTH: 191
<212> TYPE: PRT
<213> ORGANISM: Homo sapiens

<400> SEQUENCE: 6

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140
```

```
Pro Cys Ser Glu Glu Glu Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Glu Cys Asp Lys Pro Arg Arg
            180                 185                 190


<210> SEQ ID NO 7
<211> LENGTH: 165
<212> TYPE: PRT
<213> ORGANISM: Homo sapiens

<400> SEQUENCE: 7

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Glu Glu Lys His Leu Phe
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Glu Cys
145                 150                 155                 160

Asp Lys Pro Arg Arg
                165


<210> SEQ ID NO 8
<211> LENGTH: 55
<212> TYPE: PRT
<213> ORGANISM: Homo sapiens

<400> SEQUENCE: 8

Ala Arg Gln Glu Asn Pro Cys Gly Pro Cys Ser Glu Glu Glu Lys His
1               5                   10                  15

Leu Phe Val Gln Asp Pro Gln Thr Cys Lys Cys Ser Cys Lys Asn Thr
            20                  25                  30

Asp Ser Arg Cys Lys Ala Arg Gln Leu Glu Leu Asn Glu Arg Thr Cys
        35                  40                  45

Glu Cys Asp Lys Pro Arg Arg
    50                  55


<210> SEQ ID NO 9
<211> LENGTH: 576
<212> TYPE: DNA
<213> ORGANISM: Homo sapiens
<220> FEATURE:
<221> NAME/KEY: CDS
<222> LOCATION: (1)..(576)
```

<400> SEQUENCE: 9

```
atg aac ttt ctg ctg agc tgg gtg cac tgg tcc ctg gcc ctg ctg ctg      48
Met Asn Phe Leu Leu Ser Trp Val His Trp Ser Leu Ala Leu Leu Leu
1               5                   10                  15

tac ctg cac cac gcc aag tgg tcc cag gcc gct cct atg gcc gag ggc      96
Tyr Leu His His Ala Lys Trp Ser Gln Ala Ala Pro Met Ala Glu Gly
            20                  25                  30

gga ggc cag aac cac cac gag gtg gtg aaa ttc atg gac gtg tac cag     144
Gly Gly Gln Asn His His Glu Val Val Lys Phe Met Asp Val Tyr Gln
        35                  40                  45

cgg agc tac tgc cac ccc atc gag aca ctg gtg gac atc ttc cag gaa     192
Arg Ser Tyr Cys His Pro Ile Glu Thr Leu Val Asp Ile Phe Gln Glu
    50                  55                  60

tac ccc gac gag atc gag tac atc ttc aag ccc agc tgc gtg ccc ctg     240
Tyr Pro Asp Glu Ile Glu Tyr Ile Phe Lys Pro Ser Cys Val Pro Leu
65                  70                  75                  80

atg aga tgc ggc ggc tgc tgc aac gac gag ggc ctg gaa tgc gtg ccc     288
Met Arg Cys Gly Gly Cys Cys Asn Asp Glu Gly Leu Glu Cys Val Pro
                85                  90                  95

acc gag gaa tcc aac atc acc atg cag atc atg cgg atc aag ccc cac     336
Thr Glu Glu Ser Asn Ile Thr Met Gln Ile Met Arg Ile Lys Pro His
            100                 105                 110

cag ggc cag cat atc ggc gag atg agc ttc ctg cag cac aac aag tgc     384
Gln Gly Gln His Ile Gly Glu Met Ser Phe Leu Gln His Asn Lys Cys
        115                 120                 125

gag tgc cgg ccc aag aag gac cgg gcc aga cag gaa aac ccc tgc ggc     432
Glu Cys Arg Pro Lys Lys Asp Arg Ala Arg Gln Glu Asn Pro Cys Gly
    130                 135                 140

ccc tgc agc gag gag gaa aag cac ctg ttc gtg cag gac ccc cag acc     480
Pro Cys Ser Glu Glu Glu Lys His Leu Phe Val Gln Asp Pro Gln Thr
145                 150                 155                 160

tgc aag tgc tcc tgc aag aac acc gac agc cgg tgc aag gcc cgg cag     528
Cys Lys Cys Ser Cys Lys Asn Thr Asp Ser Arg Cys Lys Ala Arg Gln
                165                 170                 175

ctg gaa ctg aac gag cgg acc tgc aga tgc gac aag ccc aga cgg taa     576
Leu Glu Leu Asn Glu Arg Thr Cys Arg Cys Asp Lys Pro Arg Arg
            180                 185                 190
```

<210> SEQ ID NO 10
<211> LENGTH: 191
<212> TYPE: PRT
<213> ORGANISM: Homo sapiens

<400> SEQUENCE: 10

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110
```

Gln Gly Gln His Ile Gly Glu Met Ser Phe Leu Gln His Asn Lys Cys
115 120 125

Glu Cys Arg Pro Lys Lys Asp Arg Ala Arg Gln Glu Asn Pro Cys Gly
130 135 140

Pro Cys Ser Glu Glu Glu Lys His Leu Phe Val Gln Asp Pro Gln Thr
145 150 155 160

Cys Lys Cys Ser Cys Lys Asn Thr Asp Ser Arg Cys Lys Ala Arg Gln
165 170 175

Leu Glu Leu Asn Glu Arg Thr Cys Arg Cys Asp Lys Pro Arg Arg
180 185 190

<210> SEQ ID NO 11
<211> LENGTH: 165
<212> TYPE: PRT
<213> ORGANISM: Homo sapiens

<400> SEQUENCE: 11

Ala Pro Met Ala Glu Gly Gly Gly Gln Asn His His Glu Val Val Lys
1 5 10 15

Phe Met Asp Val Tyr Gln Arg Ser Tyr Cys His Pro Ile Glu Thr Leu
20 25 30

Val Asp Ile Phe Gln Glu Tyr Pro Asp Glu Ile Glu Tyr Ile Phe Lys
35 40 45

Pro Ser Cys Val Pro Leu Met Arg Cys Gly Gly Cys Cys Asn Asp Glu
50 55 60

Gly Leu Glu Cys Val Pro Thr Glu Glu Ser Asn Ile Thr Met Gln Ile
65 70 75 80

Met Arg Ile Lys Pro His Gln Gly Gln His Ile Gly Glu Met Ser Phe
85 90 95

Leu Gln His Asn Lys Cys Glu Cys Arg Pro Lys Lys Asp Arg Ala Arg
100 105 110

Gln Glu Asn Pro Cys Gly Pro Cys Ser Glu Glu Glu Lys His Leu Phe
115 120 125

Val Gln Asp Pro Gln Thr Cys Lys Cys Ser Cys Lys Asn Thr Asp Ser
130 135 140

Arg Cys Lys Ala Arg Gln Leu Glu Leu Asn Glu Arg Thr Cys Arg Cys
145 150 155 160

Asp Lys Pro Arg Arg
165

<210> SEQ ID NO 12
<211> LENGTH: 55
<212> TYPE: PRT
<213> ORGANISM: Homo sapiens

<400> SEQUENCE: 12

Ala Arg Gln Glu Asn Pro Cys Gly Pro Cys Ser Glu Glu Glu Lys His
1 5 10 15

Leu Phe Val Gln Asp Pro Gln Thr Cys Lys Cys Ser Cys Lys Asn Thr
20 25 30

Asp Ser Arg Cys Lys Ala Arg Gln Leu Glu Leu Asn Glu Arg Thr Cys
35 40 45

Arg Cys Asp Lys Pro Arg Arg
50 55

<210> SEQ ID NO 13
<211> LENGTH: 576

```
<212> TYPE: DNA
<213> ORGANISM: Homo sapiens
<220> FEATURE:
<221> NAME/KEY: CDS
<222> LOCATION: (1)..(576)

<400> SEQUENCE: 13

atg aac ttt ctg ctg agc tgg gtg cac tgg tcc ctg gcc ctg ctg ctg       48
Met Asn Phe Leu Leu Ser Trp Val His Trp Ser Leu Ala Leu Leu Leu
1               5                   10                  15

tac ctg cac cac gcc aag tgg tcc cag gcc gct cct atg gcc gag ggc       96
Tyr Leu His His Ala Lys Trp Ser Gln Ala Ala Pro Met Ala Glu Gly
            20                  25                  30

gga ggc cag aac cac cac gag gtg gtg aaa ttc atg gac gtg tac cag      144
Gly Gly Gln Asn His His Glu Val Val Lys Phe Met Asp Val Tyr Gln
        35                  40                  45

cgg agc tac tgc cac ccc atc gag aca ctg gtg gac atc ttc cag gaa      192
Arg Ser Tyr Cys His Pro Ile Glu Thr Leu Val Asp Ile Phe Gln Glu
    50                  55                  60

tac ccc gac gag atc gag tac atc ttc aag ccc agc tgc gtg ccc ctg      240
Tyr Pro Asp Glu Ile Glu Tyr Ile Phe Lys Pro Ser Cys Val Pro Leu
65                  70                  75                  80

atg aga tgc ggc ggc tgc tgc aac gac gag ggc ctg gaa tgc gtg ccc      288
Met Arg Cys Gly Gly Cys Cys Asn Asp Glu Gly Leu Glu Cys Val Pro
                85                  90                  95

acc gag gaa tcc aac atc acc atg cag atc atg cgg atc aag ccc cac      336
Thr Glu Glu Ser Asn Ile Thr Met Gln Ile Met Arg Ile Lys Pro His
            100                 105                 110

cag ggc cag cat atc ggc gag atg agc ttc ctg cag cac aac aag tgc      384
Gln Gly Gln His Ile Gly Glu Met Ser Phe Leu Gln His Asn Lys Cys
        115                 120                 125

gag tgc cgg ccc aag aag gac cgg gcc aga cag gaa aac ccc tgc ggc      432
Glu Cys Arg Pro Lys Lys Asp Arg Ala Arg Gln Glu Asn Pro Cys Gly
    130                 135                 140

ccc tgc agc gag cgg aga aag cac ctg ttc gtg cag gac ccc cag acc      480
Pro Cys Ser Glu Arg Arg Lys His Leu Phe Val Gln Asp Pro Gln Thr
145                 150                 155                 160

tgc aag tgc tcc tgc aag aac acc gac agc cgg tgc aag gcc cgg cag      528
Cys Lys Cys Ser Cys Lys Asn Thr Asp Ser Arg Cys Lys Ala Arg Gln
                165                 170                 175

ctg gaa ctg aac gag cgg acc tgc gaa tgc gac aag ccc aga cgg taa      576
Leu Glu Leu Asn Glu Arg Thr Cys Glu Cys Asp Lys Pro Arg Arg
            180                 185                 190


<210> SEQ ID NO 14
<211> LENGTH: 191
<212> TYPE: PRT
<213> ORGANISM: Homo sapiens

<400> SEQUENCE: 14

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80
```

```
Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Glu Cys Asp Lys Pro Arg Arg
            180                 185                 190


<210> SEQ ID NO 15
<211> LENGTH: 165
<212> TYPE: PRT
<213> ORGANISM: Homo sapiens

<400> SEQUENCE: 15

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Glu Cys
145                 150                 155                 160

Asp Lys Pro Arg Arg
                165


<210> SEQ ID NO 16
<211> LENGTH: 55
<212> TYPE: PRT
<213> ORGANISM: Homo sapiens

<400> SEQUENCE: 16

Ala Arg Gln Glu Asn Pro Cys Gly Pro Cys Ser Glu Arg Arg Lys His
1               5                   10                  15

Leu Phe Val Gln Asp Pro Gln Thr Cys Lys Cys Ser Cys Lys Asn Thr
            20                  25                  30

Asp Ser Arg Cys Lys Ala Arg Gln Leu Glu Leu Asn Glu Arg Thr Cys
        35                  40                  45
```

```
Glu Cys Asp Lys Pro Arg Arg
    50                  55


<210> SEQ ID NO 17
<211> LENGTH: 576
<212> TYPE: DNA
<213> ORGANISM: Homo sapiens
<220> FEATURE:
<221> NAME/KEY: CDS
<222> LOCATION: (1)..(576)

<400> SEQUENCE: 17

atg aac ttt ctg ctg agc tgg gtg cac tgg tcc ctg gcc ctg ctg ctg        48
Met Asn Phe Leu Leu Ser Trp Val His Trp Ser Leu Ala Leu Leu Leu
1               5                   10                  15

tac ctg cac cac gcc aag tgg tcc cag gcc gct cct atg gcc gag ggc        96
Tyr Leu His His Ala Lys Trp Ser Gln Ala Ala Pro Met Ala Glu Gly
            20                  25                  30

gga ggc cag aac cac cac gag gtg gtg aaa ttc atg gac gtg tac cag       144
Gly Gly Gln Asn His His Glu Val Val Lys Phe Met Asp Val Tyr Gln
        35                  40                  45

cgg agc tac tgc cac ccc atc gag aca ctg gtg gac atc ttc cag gaa       192
Arg Ser Tyr Cys His Pro Ile Glu Thr Leu Val Asp Ile Phe Gln Glu
    50                  55                  60

tac ccc gac gag atc gag tac atc ttc aag ccc agc tgc gtg ccc ctg       240
Tyr Pro Asp Glu Ile Glu Tyr Ile Phe Lys Pro Ser Cys Val Pro Leu
65                  70                  75                  80

atg aga tgc ggc ggc tgc tgc aac gac gag ggc ctg gaa tgc gtg ccc       288
Met Arg Cys Gly Gly Cys Cys Asn Asp Glu Gly Leu Glu Cys Val Pro
                85                  90                  95

acc gag gaa tcc aac atc acc atg cag atc atg cgg atc aag ccc cac       336
Thr Glu Glu Ser Asn Ile Thr Met Gln Ile Met Arg Ile Lys Pro His
            100                 105                 110

cag ggc cag cat atc ggc gag atg agc ttc ctg cag cac aac aag tgc       384
Gln Gly Gln His Ile Gly Glu Met Ser Phe Leu Gln His Asn Lys Cys
        115                 120                 125

gag tgc cgg ccc aag aag gac cgg gcc aga cag gaa aac ccc tgc ggc       432
Glu Cys Arg Pro Lys Lys Asp Arg Ala Arg Gln Glu Asn Pro Cys Gly
    130                 135                 140

ccc tgc agc gag cgg gaa aag cac ctg ttc gtg cag gac ccc cag acc       480
Pro Cys Ser Glu Arg Glu Lys His Leu Phe Val Gln Asp Pro Gln Thr
145                 150                 155                 160

tgc aag tgc tcc tgc aag aac acc gac agc cgg tgc aag gcc cgg cag       528
Cys Lys Cys Ser Cys Lys Asn Thr Asp Ser Arg Cys Lys Ala Arg Gln
                165                 170                 175

ctg gaa ctg aac gag cgg acc tgc aga tgc gac aag ccc aga cgg taa       576
Leu Glu Leu Asn Glu Arg Thr Cys Arg Cys Asp Lys Pro Arg Arg
            180                 185                 190


<210> SEQ ID NO 18
<211> LENGTH: 191
<212> TYPE: PRT
<213> ORGANISM: Homo sapiens

<400> SEQUENCE: 18

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45
```

-continued

```
Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Glu Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190


<210> SEQ ID NO 19
<211> LENGTH: 165
<212> TYPE: PRT
<213> ORGANISM: Homo sapiens

<400> SEQUENCE: 19

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Glu Lys His Leu Phe
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Arg Cys
145                 150                 155                 160

Asp Lys Pro Arg Arg
                165


<210> SEQ ID NO 20
<211> LENGTH: 55
<212> TYPE: PRT
<213> ORGANISM: Homo sapiens

<400> SEQUENCE: 20

Ala Arg Gln Glu Asn Pro Cys Gly Pro Cys Ser Glu Arg Glu Lys His
1               5                   10                  15
```

```
Leu Phe Val Gln Asp Pro Gln Thr Cys Lys Cys Ser Cys Lys Asn Thr
            20                  25                  30

Asp Ser Arg Cys Lys Ala Arg Gln Leu Glu Leu Asn Glu Arg Thr Cys
        35                  40                  45

Arg Cys Asp Lys Pro Arg Arg
    50                  55


<210> SEQ ID NO 21
<211> LENGTH: 576
<212> TYPE: DNA
<213> ORGANISM: Homo sapiens
<220> FEATURE:
<221> NAME/KEY: CDS
<222> LOCATION: (1)..(576)

<400> SEQUENCE: 21

atg aac ttt ctg ctg agc tgg gtg cac tgg tcc ctg gcc ctg ctg ctg       48
Met Asn Phe Leu Leu Ser Trp Val His Trp Ser Leu Ala Leu Leu Leu
1               5                   10                  15

tac ctg cac cac gcc aag tgg tcc cag gcc gct cct atg gcc gag ggc       96
Tyr Leu His His Ala Lys Trp Ser Gln Ala Ala Pro Met Ala Glu Gly
            20                  25                  30

gga ggc cag aac cac cac gag gtg gtg aaa ttc atg gac gtg tac cag      144
Gly Gly Gln Asn His His Glu Val Val Lys Phe Met Asp Val Tyr Gln
        35                  40                  45

cgg agc tac tgc cac ccc atc gag aca ctg gtg gac atc ttc cag gaa      192
Arg Ser Tyr Cys His Pro Ile Glu Thr Leu Val Asp Ile Phe Gln Glu
    50                  55                  60

tac ccc gac gag atc gag tac atc ttc aag ccc agc tgc gtg ccc ctg      240
Tyr Pro Asp Glu Ile Glu Tyr Ile Phe Lys Pro Ser Cys Val Pro Leu
65                  70                  75                  80

atg aga tgc ggc ggc tgc tgc aac gac gag ggc ctg gaa tgc gtg ccc      288
Met Arg Cys Gly Gly Cys Cys Asn Asp Glu Gly Leu Glu Cys Val Pro
                85                  90                  95

acc gag gaa tcc aac atc acc atg cag atc atg cgg atc aag ccc cac      336
Thr Glu Glu Ser Asn Ile Thr Met Gln Ile Met Arg Ile Lys Pro His
            100                 105                 110

cag ggc cag cat atc ggc gag atg agc ttc ctg cag cac aac aag tgc      384
Gln Gly Gln His Ile Gly Glu Met Ser Phe Leu Gln His Asn Lys Cys
        115                 120                 125

gag tgc cgg ccc aag aag gac cgg gcc aga cag gaa aac ccc tgc ggc      432
Glu Cys Arg Pro Lys Lys Asp Arg Ala Arg Gln Glu Asn Pro Cys Gly
    130                 135                 140

ccc tgc agc gag gag aga aag cac ctg ttc gtg cag gac ccc cag acc      480
Pro Cys Ser Glu Glu Arg Lys His Leu Phe Val Gln Asp Pro Gln Thr
145                 150                 155                 160

tgc aag tgc tcc tgc aag aac acc gac agc cgg tgc aag gcc cgg cag      528
Cys Lys Cys Ser Cys Lys Asn Thr Asp Ser Arg Cys Lys Ala Arg Gln
                165                 170                 175

ctg gaa ctg aac gag cgg acc tgc aga tgc gac aag ccc aga cgg taa      576
Leu Glu Leu Asn Glu Arg Thr Cys Arg Cys Asp Lys Pro Arg Arg
            180                 185                 190


<210> SEQ ID NO 22
<211> LENGTH: 191
<212> TYPE: PRT
<213> ORGANISM: Homo sapiens

<400> SEQUENCE: 22

Met Asn Phe Leu Leu Ser Trp Val His Trp Ser Leu Ala Leu Leu Leu
1               5                   10                  15
```

```
Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Glu Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190
```

<210> SEQ ID NO 23
<211> LENGTH: 165
<212> TYPE: PRT
<213> ORGANISM: Homo sapiens

<400> SEQUENCE: 23

```
Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Glu Arg Lys His Leu Phe
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Arg Cys
145                 150                 155                 160

Asp Lys Pro Arg Arg
                165
```

<210> SEQ ID NO 24
<211> LENGTH: 55
<212> TYPE: PRT
<213> ORGANISM: Homo sapiens

<400> SEQUENCE: 24

Ala Arg Gln Glu Asn Pro Cys Gly Pro Cys Ser Glu Glu Arg Lys His
1 5 10 15

Leu Phe Val Gln Asp Pro Gln Thr Cys Lys Cys Ser Cys Lys Asn Thr
20 25 30

Asp Ser Arg Cys Lys Ala Arg Gln Leu Glu Leu Asn Glu Arg Thr Cys
35 40 45

Arg Cys Asp Lys Pro Arg Arg
50 55

<210> SEQ ID NO 25
<211> LENGTH: 191
<212> TYPE: PRT
<213> ORGANISM: Homo sapiens
<220> FEATURE:
<221> NAME/KEY: VARIANT
<222> LOCATION: (149)..(150)
<223> OTHER INFORMATION: Xaa is Asp or Glu
<220> FEATURE:
<221> NAME/KEY: VARIANT
<222> LOCATION: (185)..(185)
<223> OTHER INFORMATION: Xaa is Asp or Glu

<400> SEQUENCE: 25

Met Asn Phe Leu Leu Ser Trp Val His Trp Ser Leu Ala Leu Leu Leu
1 5 10 15

Tyr Leu His His Ala Lys Trp Ser Gln Ala Ala Pro Met Ala Glu Gly
20 25 30

Gly Gly Gln Asn His His Glu Val Val Lys Phe Met Asp Val Tyr Gln
35 40 45

Arg Ser Tyr Cys His Pro Ile Glu Thr Leu Val Asp Ile Phe Gln Glu
50 55 60

Tyr Pro Asp Glu Ile Glu Tyr Ile Phe Lys Pro Ser Cys Val Pro Leu
65 70 75 80

Met Arg Cys Gly Gly Cys Cys Asn Asp Glu Gly Leu Glu Cys Val Pro
85 90 95

Thr Glu Glu Ser Asn Ile Thr Met Gln Ile Met Arg Ile Lys Pro His
100 105 110

Gln Gly Gln His Ile Gly Glu Met Ser Phe Leu Gln His Asn Lys Cys
115 120 125

Glu Cys Arg Pro Lys Lys Asp Arg Ala Arg Gln Glu Asn Pro Cys Gly
130 135 140

Pro Cys Ser Glu Xaa Xaa Lys His Leu Phe Val Gln Asp Pro Gln Thr
145 150 155 160

Cys Lys Cys Ser Cys Lys Asn Thr Asp Ser Arg Cys Lys Ala Arg Gln
165 170 175

Leu Glu Leu Asn Glu Arg Thr Cys Xaa Cys Asp Lys Pro Arg Arg
180 185 190

<210> SEQ ID NO 26
<211> LENGTH: 165
<212> TYPE: PRT
<213> ORGANISM: Homo sapiens
<220> FEATURE:
<221> NAME/KEY: VARIANT
<222> LOCATION: (123)..(124)
<223> OTHER INFORMATION: Xaa is Asp or Glu
<220> FEATURE:
<221> NAME/KEY: VARIANT
<222> LOCATION: (159)..(159)

<223> OTHER INFORMATION: Xaa is Asp or Glu

<400> SEQUENCE: 26

```
Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Xaa Xaa Lys His Leu Phe
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Xaa Cys
145                 150                 155                 160

Asp Lys Pro Arg Arg
                165
```

<210> SEQ ID NO 27
<211> LENGTH: 55
<212> TYPE: PRT
<213> ORGANISM: Homo sapiens
<220> FEATURE:
<221> NAME/KEY: VARIANT
<222> LOCATION: (13)..(14)
<223> OTHER INFORMATION: Xaa is Asp or Glu
<220> FEATURE:
<221> NAME/KEY: VARIANT
<222> LOCATION: (49)..(49)
<223> OTHER INFORMATION: Xaa is Asp or Glu

<400> SEQUENCE: 27

```
Ala Arg Gln Glu Asn Pro Cys Gly Pro Cys Ser Glu Xaa Xaa Lys His
1               5                   10                  15

Leu Phe Val Gln Asp Pro Gln Thr Cys Lys Cys Ser Cys Lys Asn Thr
            20                  25                  30

Asp Ser Arg Cys Lys Ala Arg Gln Leu Glu Leu Asn Glu Arg Thr Cys
        35                  40                  45

Xaa Cys Asp Lys Pro Arg Arg
    50                  55
```

<210> SEQ ID NO 28
<211> LENGTH: 6072
<212> TYPE: DNA
<213> ORGANISM: Artificial Sequence
<220> FEATURE:
<223> OTHER INFORMATION: Plasmid containing Hs.VEGF165 wild type
sequence (6072 bp DNA circular)
<220> FEATURE:
<221> NAME/KEY: promoter
<222> LOCATION: (232)..(819)
<223> OTHER INFORMATION: /gene="pCMV"
/product="CMV promoter (-601 to +15)"
<220> FEATURE:

<221> NAME/KEY: promoter
<222> LOCATION: (863)..(882)
<223> OTHER INFORMATION: /gene="pT7"
/product="T7 promoter"
<220> FEATURE:
<221> NAME/KEY: misc_recomb
<222> LOCATION: (911)..(932)
<223> OTHER INFORMATION: /gene="attB1"
/product="attB1 recombination site"
<220> FEATURE:
<221> NAME/KEY: misc_feature
<222> LOCATION: (938)..(1513)
<223> OTHER INFORMATION: /gene="Hs.VEGF165"
<220> FEATURE:
<221> NAME/KEY: misc_recomb
<222> LOCATION: (1515)..(1536)
<223> OTHER INFORMATION: /gene="attB2"
/product="attB2 recombination site"
<220> FEATURE:
<221> NAME/KEY: misc_feature
<222> LOCATION: (1562)..(1603)
<223> OTHER INFORMATION: /gene="V5"
<220> FEATURE:
<221> NAME/KEY: polyA_site
<222> LOCATION: (1630)..(1901)
<223> OTHER INFORMATION: /gene="pA"
/product="TK polyA"
<220> FEATURE:
<221> NAME/KEY: misc_feature
<222> LOCATION: (1937)..(2365)
<223> OTHER INFORMATION: /gene="f1"
/product="f1 origin"
<220> FEATURE:
<221> NAME/KEY: promoter
<222> LOCATION: (2392)..(2700)
<223> OTHER INFORMATION: /gene="pS"
/product="SV40 promoter"
<220> FEATURE:
<221> NAME/KEY: misc_feature
<222> LOCATION: (2775)..(3569)
<223> OTHER INFORMATION: /gene="neo"
<220> FEATURE:
<221> NAME/KEY: polyA_signal
<222> LOCATION: (3745)..(3875)
<220> FEATURE:
<221> NAME/KEY: misc_feature
<222> LOCATION: (4258)..(4931)
<223> OTHER INFORMATION: /gene="oriP"
/product="pUC origin"
<220> FEATURE:
<221> NAME/KEY: misc_feature
<222> LOCATION: (5076)..(5936)
<223> OTHER INFORMATION: /gene="bla"

<400> SEQUENCE: 28
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720

-continued

```
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagt    900
taagctatca acaagtttgt acaaaaaagt tggcaccatg aactttctgc tgagctgggt    960
gcactggtcc ctggccctgc tgctgtacct gcaccacgcc aagtggtccc aggccgctcc   1020
tatggccgag ggcggaggcc agaaccacca cgaggtggtg aaattcatgg acgtgtacca   1080
gcggagctac tgccacccca tcgagacact ggtggacatc ttccaggaat accccgacga   1140
gatcgagtac atcttcaagc ccagctgcgt gcccctgatg agatgcggcg gctgctgcaa   1200
cgacgagggc ctggaatgcg tgcccaccga ggaatccaac atcaccatgc agatcatgcg   1260
gatcaagccc caccagggcc agcatatcgg cgagatgagc ttcctgcagc acaacaagtg   1320
cgagtgccgg cccaagaagg accgggccag acaggaaaac ccctgcggcc cctgcagcga   1380
gcggagaaag cacctgttcg tgcaggaccc ccagacctgc aagtgctcct gcaagaacac   1440
cgacagccgg tgcaaggccc ggcagctgga actgaacgag cggacctgca gatgcgacaa   1500
gcccagacgg taatcaactt tcttgtacaa agtggttgat ctagagggcc cgcggttcga   1560
aggtaagcct atccctaacc ctctcctcgg tctcgattct acgcgtaccg gttagtaatg   1620
agtttaaacg gggaggcta actgaaacac ggaaggagac aataccggaa ggaacccgcg   1680
ctatgacggc aataaaaaga cagaataaaa cgcacgggtg ttgggtcgtt tgttcataaa   1740
cgcggggttc ggtcccaggg ctggcactct gtcgataccc caccgagacc ccattggggc   1800
caatacgccc gcgtttcttc cttttcccca ccccaccccc caagttcggg tgaaggccca   1860
gggctcgcag ccaacgtcgg ggcggcaggc cctgccatag cagatctgcg cagctggggc   1920
tctagggggt atccccacgc gccctgtagc ggcgcattaa gcgcggcggg tgtggtggtt   1980
acgcgcagcg tgaccgctac acttgccagc gccctagcgc ccgctccttt cgctttcttc   2040
ccttcctttc tcgccacgtt cgccggcttt ccccgtcaag ctctaaatcg ggcatccct   2100
ttagggttcc gatttagtgc tttacggcac ctcgacccca aaaaacttga ttagggtgat   2160
ggttcacgta gtgggccatc gccctgatag acggtttttc gccctttgac gttggagtcc   2220
acgttcttta atagtggact cttgttccaa actggaacaa cactcaaccc tatctcggtc   2280
tattcttttg atttataagg gattttgggg atttcggcct attggttaaa aaatgagctg   2340
atttaacaaa aatttaacgc gaattaattc tgtggaatgt gtgtcagtta gggtgtggaa   2400
agtccccagg ctccccagca ggcagaagta tgcaaagcat gcatctcaat tagtcagcaa   2460
ccaggtgtgg aaagtcccca ggctccccag caggcagaag tatgcaaagc atgcatctca   2520
attagtcagc aaccatagtc ccgcccctaa ctccgcccat cccgccccta actccgccca   2580
gttccgccca ttctccgccc catggctgac taatttttt tatttatgca gaggccgagg   2640
ccgcctctgc ctctgagcta ttccagaagt agtgaggagg cttttttgga ggcctaggct   2700
tttgcaaaaa gctcccggga gcttgtatat ccattttcgg atctgatcaa gagacaggat   2760
gaggatcgtt tcgcatgatt gaacaagatg gattgcacgc aggttctccg gccgcttggg   2820
tggagaggct attcggctat gactgggcac aacagacaat cggctgctct gatgccgccg   2880
tgttccggct gtcagcgcag gggcgcccgg ttctttttgt caagaccgac ctgtccggtg   2940
ccctgaatga actgcaggac gaggcagcgc ggctatcgtg gctggccacg acgggcgttc   3000
cttgcgcagc tgtgctcgac gttgtcactg aagcgggaag ggactggctg ctattgggcg   3060
```

-continued

```
aagtgccggg gcaggatctc ctgtcatctc accttgctcc tgccgagaaa gtatccatca   3120
tggctgatgc aatgcggcgg ctgcatacgc ttgatccggc tacctgccca ttcgaccacc   3180
aagcgaaaca tcgcatcgag cgagcacgta ctcggatgga agccggtctt gtcgatcagg   3240
atgatctgga cgaagagcat caggggctcg cgccagccga actgttcgcc aggctcaagg   3300
cgcgcatgcc cgacggcgag gatctcgtcg tgacccatgg cgatgcctgc ttgccgaata   3360
tcatggtgga aaatggccgc ttttctggat tcatcgactg tggccggctg ggtgtggcgg   3420
accgctatca ggacatagcg ttggctaccc gtgatattgc tgaagagctt ggcggcgaat   3480
gggctgaccg cttcctcgtg ctttacggta tcgccgctcc cgattcgcag cgcatcgcct   3540
tctatcgcct tcttgacgag ttcttctgag cgggactctg gggttcgcga aatgaccgac   3600
caagcgacgc ccaacctgcc atcacgagat ttcgattcca ccgccgcctt ctatgaaagg   3660
ttgggcttcg gaatcgtttt ccgggacgcc ggctggatga tcctccagcg cggggatctc   3720
atgctggagt tcttcgccca ccccaacttg tttattgcag cttataatgg ttacaaataa   3780
agcaatagca tcacaaattt cacaaataaa gcattttttt cactgcattc tagttgtggt   3840
ttgtccaaac tcatcaatgt atcttatcat gtctgtatac cgtcgacctc tagctagagc   3900
ttggcgtaat catggtcata gctgtttcct gtgtgaaatt gttatccgct cacaattcca   3960
cacaacatac gagccggaag cataaagtgt aaagcctggg gtgcctaatg agtgagctaa   4020
ctcacattaa ttgcgttgcg ctcactgccc gctttccagt cgggaaacct gtcgtgccag   4080
ctgcattaat gaatcggcca acgcgcgggg agaggcggtt tgcgtattgg gcgctcttcc   4140
gcttcctcgc tcactgactc gctgcgctcg gtcgttcggc tgcggcgagc ggtatcagct   4200
cactcaaagg cggtaatacg gttatccaca gaatcagggg ataacgcagg aaagaacatg   4260
tgagcaaaag gccagcaaaa ggccaggaac cgtaaaaagg ccgcgttgct ggcgtttttc   4320
cataggctcc gcccccctga cgagcatcac aaaaatcgac gctcaagtca gaggtggcga   4380
aacccgacag gactataaag ataccaggcg tttccccctg gaagctccct cgtgcgctct   4440
cctgttccga ccctgccgct taccggatac ctgtccgcct ttctcccttc gggaagcgtg   4500
gcgctttctc aatgctcacg ctgtaggtat ctcagttcgg tgtaggtcgt tcgctccaag   4560
ctgggctgtg tgcacgaacc ccccgttcag cccgaccgct gcgccttatc cggtaactat   4620
cgtcttgagt ccaacccggt aagacacgac ttatcgccac tggcagcagc cactggtaac   4680
aggattagca gagcgaggta tgtaggcggt gctacagagt tcttgaagtg gtggcctaac   4740
tacggctaca ctagaaggac agtatttggt atctgcgctc tgctgaagcc agttaccttc   4800
ggaaaaagag ttggtagctc ttgatccggc aaacaaacca ccgctggtag cggtggtttt   4860
tttgtttgca agcagcagat tacgcgcaga aaaaaaggat ctcaagaaga tcctttgatc   4920
ttttctacgg ggtctgacgc tcagtggaac gaaaactcac gttaagggat tttggtcatg   4980
agattatcaa aaaggatctt cacctagatc cttttaaatt aaaaatgaag ttttaaatca   5040
atctaaagta tatatgagta aacttggtct gacagttacc aatgcttaat cagtgaggca   5100
cctatctcag cgatctgtct atttcgttca tccatagttg cctgactccc cgtcgtgtag   5160
ataactacga tacgggaggg cttaccatct ggccccagtg ctgcaatgat accgcgagac   5220
ccacgctcac cggctccaga tttatcagca ataaaccagc cagccggaag ggccgagcgc   5280
agaagtggtc ctgcaacttt atccgcctcc atccagtcta ttaattgttg ccgggaagct   5340
agagtaagta gttcgccagt taatagtttg cgcaacgttg ttgccattgc tacaggcatc   5400
gtggtgtcac gctcgtcgtt tggtatggct tcattcagct ccggttccca acgatcaagg   5460
```

```
cgagttacat gatcccccat gttgtgcaaa aaagcggtta gctccttcgg tcctccgatc   5520

gttgtcagaa gtaagttggc cgcagtgtta tcactcatgg ttatggcagc actgcataat   5580

tctcttactg tcatgccatc cgtaagatgc ttttctgtga ctggtgagta ctcaaccaag   5640

tcattctgag aatagtgtat gcggcgaccg agttgctctt gcccggcgtc aatacgggat   5700

aataccgcgc cacatagcag aactttaaaa gtgctcatca ttggaaaacg ttcttcgggg   5760

cgaaaactct caaggatctt accgctgttg agatccagtt cgatgtaacc cactcgtgca   5820

cccaactgat cttcagcatc ttttactttc accagcgttt ctgggtgagc aaaaacagga   5880

aggcaaaatg ccgcaaaaaa gggaataagg gcgacacgga aatgttgaat actcatactc   5940

ttcctttttc aatattattg aagcatttat cagggttatt gtctcatgag cggatacata   6000

tttgaatgta tttagaaaaa taaacaaata ggggttccgc gcacatttcc ccgaaaagtg   6060

ccacctgacg tc                                                       6072
```

<210> SEQ ID NO 29
<211> LENGTH: 6072
<212> TYPE: DNA
<213> ORGANISM: Artificial Sequence
<220> FEATURE:
<223> OTHER INFORMATION: Plasmid containing Hs.VEGF165 R149E/R150E/R185E
(6072 bp DNA circular)
<220> FEATURE:
<221> NAME/KEY: promoter
<222> LOCATION: (232)..(819)
<223> OTHER INFORMATION: /gene="pCMV"
/product="CMV promoter (-601 to +15)"
<220> FEATURE:
<221> NAME/KEY: promoter
<222> LOCATION: (863)..(882)
<223> OTHER INFORMATION: /gene="pT7"
/product="T7 promoter"
<220> FEATURE:
<221> NAME/KEY: misc_recomb
<222> LOCATION: (911)..(932)
<223> OTHER INFORMATION: /gene="attB1"
/product="attB1 recombination site"
<220> FEATURE:
<221> NAME/KEY: misc_feature
<222> LOCATION: (938)..(1513)
<223> OTHER INFORMATION: /gene="Hs.VEGF165 R149E/R150E/R185E"
<220> FEATURE:
<221> NAME/KEY: misc_recomb
<222> LOCATION: (1515)..(1536)
<223> OTHER INFORMATION: /gene="attB2"
/product="attB2 recombination site"
<220> FEATURE:
<221> NAME/KEY: misc_feature
<222> LOCATION: (1562)..(1603)
<223> OTHER INFORMATION: /gene="V5"
<220> FEATURE:
<221> NAME/KEY: polyA_site
<222> LOCATION: (1630)..(1901)
<223> OTHER INFORMATION: /gene="pA"
/product="TK polyA"
<220> FEATURE:
<221> NAME/KEY: misc_feature
<222> LOCATION: (1937)..(2365)
<223> OTHER INFORMATION: /gene="f1"
/product="f1 origin"
<220> FEATURE:
<221> NAME/KEY: promoter
<222> LOCATION: (2392)..(2700)
<223> OTHER INFORMATION: /gene="pS"
/product="SV40 promoter"
<220> FEATURE:
<221> NAME/KEY: misc_feature
<222> LOCATION: (2775)..(3569)
<223> OTHER INFORMATION: /gene="neo"
<220> FEATURE:

<221> NAME/KEY: polyA_site
<222> LOCATION: (3745)..(3875)
<223> OTHER INFORMATION: /gene="pA"
/product="SV40 polyA"
<220> FEATURE:
<221> NAME/KEY: misc_feature
<222> LOCATION: (4258)..(4931)
<223> OTHER INFORMATION: /gene="oriP"
/product="pUC origin"
<220> FEATURE:
<221> NAME/KEY: misc_feature
<222> LOCATION: (5076)..(5936)
<223> OTHER INFORMATION: /gene="bla"

<400> SEQUENCE: 29

```
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagt    900
taagctatca acaagtttgt acaaaaaagt tggcaccatg aactttctgc tgagctgggt    960
gcactggtcc ctggccctgc tgctgtacct gcaccacgcc aagtggtccc aggccgctcc   1020
tatggccgag ggcggaggcc agaaccacca cgaggtggtg aaattcatgg acgtgtacca   1080
gcggagctac tgccacccca tcgagacact ggtggacatc ttccaggaat accccgacga   1140
gatcgagtac atcttcaagc ccagctgcgt gcccctgatg agatgcggcg gctgctgcaa   1200
cgacgagggc ctggaatgcg tgcccaccga ggaatccaac atcaccatgc agatcatgcg   1260
gatcaagccc caccagggcc agcatatcgg cgagatgagc ttcctgcagc acaacaagtg   1320
cgagtgccgg cccaagaagg accgggccag acaggaaaac ccctgcggcc cctgcagcga   1380
ggaggaaaag cacctgttcg tgcaggaccc ccagacctgc aagtgctcct gcaagaacac   1440
cgacagccgg tgcaaggccc ggcagctgga actgaacgag cggacctgcg aatgcgacaa   1500
gcccagacgg taatcaactt tcttgtacaa agtggttgat ctagagggcc cgcggttcga   1560
aggtaagcct atccctaacc ctctcctcgg tctcgattct acgcgtaccg gttagtaatg   1620
agtttaaacg gggaggcta actgaaacac ggaaggagac aataccggaa ggaacccgcg   1680
ctatgacggc aataaaaaga cagaataaaa cgcacgggtg ttgggtcgtt tgttcataaa   1740
cgcggggttc ggtcccaggg ctggcactct gtcgataccc caccgagacc ccattggggc   1800
caatacgccc gcgtttcttc cttttcccca ccccaccccc caagttcggg tgaaggccca   1860
gggctcgcag ccaacgtcgg ggcggcaggc cctgccatag cagatctgcg cagctggggc   1920
```

```
tctagggggt atccccacgc gccctgtagc ggcgcattaa gcgcggcggg tgtggtggtt   1980
acgcgcagcg tgaccgctac acttgccagc gccctagcgc ccgctccttt cgctttcttc   2040
ccttcctttc tcgccacgtt cgccggcttt ccccgtcaag ctctaaatcg ggcatccct    2100
ttagggttcc gatttagtgc tttacggcac ctcgacccca aaaaacttga ttagggtgat   2160
ggttcacgta gtgggccatc gccctgatag acggtttttc gccctttgac gttggagtcc   2220
acgttcttta atagtggact cttgttccaa actggaacaa cactcaaccc tatctcggtc   2280
tattcttttg atttataagg gattttgggg atttcggcct attggttaaa aaatgagctg   2340
atttaacaaa aatttaacgc gaattaattc tgtggaatgt gtgtcagtta gggtgtggaa   2400
agtccccagg ctccccagca ggcagaagta tgcaaagcat gcatctcaat tagtcagcaa   2460
ccaggtgtgg aaagtcccca ggctccccag caggcagaag tatgcaaagc atgcatctca   2520
attagtcagc aaccatagtc ccgcccctaa ctccgcccat cccgccccta actccgccca   2580
gttccgccca ttctccgccc catggctgac taattttttt tatttatgca gaggccgagg   2640
ccgcctctgc ctctgagcta ttccagaagt agtgaggagg cttttttgga ggcctaggct   2700
tttgcaaaaa gctcccggga gcttgtatat ccattttcgg atctgatcaa gagacaggat   2760
gaggatcgtt tcgcatgatt gaacaagatg gattgcacgc aggttctccg gccgcttggg   2820
tggagaggct attcggctat gactgggcac aacagacaat cggctgctct gatgccgccg   2880
tgttccggct gtcagcgcag gggcgcccgg ttctttttgt caagaccgac ctgtccggtg   2940
ccctgaatga actgcaggac gaggcagcgc ggctatcgtg gctggccacg acgggcgttc   3000
cttgcgcagc tgtgctcgac gttgtcactg aagcgggaag ggactggctg ctattgggcg   3060
aagtgccggg gcaggatctc ctgtcatctc accttgctcc tgccgagaaa gtatccatca   3120
tggctgatgc aatgcggcgg ctgcatacgc ttgatccggc tacctgccca ttcgaccacc   3180
aagcgaaaca tcgcatcgag cgagcacgta ctcggatgga agccggtctt gtcgatcagg   3240
atgatctgga cgaagagcat caggggctcg cgccagccga actgttcgcc aggctcaagg   3300
cgcgcatgcc cgacggcgag gatctcgtcg tgacccatgg cgatgcctgc ttgccgaata   3360
tcatggtgga aaatggccgc ttttctggat tcatcgactg tggccggctg ggtgtggcgg   3420
accgctatca ggacatagcg ttggctaccc gtgatattgc tgaagagctt ggcggcgaat   3480
gggctgaccg cttcctcgtg ctttacggta tcgccgctcc cgattcgcag cgcatcgcct   3540
tctatcgcct tcttgacgag ttcttctgag cgggactctg gggttcgcga aatgaccgac   3600
caagcgacgc ccaacctgcc atcacgagat ttcgattcca ccgccgcctt ctatgaaagg   3660
ttgggcttcg gaatcgtttt ccgggacgcc ggctggatga tcctccagcg cggggatctc   3720
atgctggagt tcttcgccca ccccaacttg tttattgcag cttataatgg ttacaaataa   3780
agcaatagca tcacaaattt cacaaataaa gcattttttt cactgcattc tagttgtggt   3840
ttgtccaaac tcatcaatgt atcttatcat gtctgtatac cgtcgacctc tagctagagc   3900
ttggcgtaat catggtcata gctgtttcct gtgtgaaatt gttatccgct cacaattcca   3960
cacaacatac gagccggaag cataaagtgt aaagcctggg gtgcctaatg agtgagctaa   4020
ctcacattaa ttgcgttgcg ctcactgccc gctttccagt cgggaaacct gtcgtgccag   4080
ctgcattaat gaatcggcca acgcgcgggg agaggcggtt tgcgtattgg gcgctcttcc   4140
gcttcctcgc tcactgactc gctgcgctcg gtcgttcggc tgcggcgagc ggtatcagct   4200
cactcaaagg cggtaatacg gttatccaca gaatcagggg ataacgcagg aaagaacatg   4260
```

-continued

```
tgagcaaaag gccagcaaaa ggccaggaac cgtaaaaagg ccgcgttgct ggcgtttttc   4320

cataggctcc gcccccctga cgagcatcac aaaaatcgac gctcaagtca gaggtggcga   4380

aacccgacag gactataaag ataccaggcg tttccccctg gaagctccct cgtgcgctct   4440

cctgttccga ccctgccgct taccggatac ctgtccgcct ttctcccttc gggaagcgtg   4500

gcgctttctc aatgctcacg ctgtaggtat ctcagttcgg tgtaggtcgt tcgctccaag   4560

ctgggctgtg tgcacgaacc ccccgttcag cccgaccgct gcgccttatc cggtaactat   4620

cgtcttgagt ccaacccggt aagacacgac ttatcgccac tggcagcagc cactggtaac   4680

aggattagca gagcgaggta tgtaggcggt gctacagagt tcttgaagtg gtggcctaac   4740

tacggctaca ctagaaggac agtatttggt atctgcgctc tgctgaagcc agttaccttc   4800

ggaaaaagag ttggtagctc ttgatccggc aaacaaacca ccgctggtag cggtggtttt   4860

tttgtttgca agcagcagat tacgcgcaga aaaaaaggat ctcaagaaga tcctttgatc   4920

ttttctacgg ggtctgacgc tcagtggaac gaaaactcac gttaagggat tttggtcatg   4980

agattatcaa aaaggatctt cacctagatc cttttaaatt aaaaatgaag ttttaaatca   5040

atctaaagta tatatgagta aacttggtct gacagttacc aatgcttaat cagtgaggca   5100

cctatctcag cgatctgtct atttcgttca tccatagttg cctgactccc cgtcgtgtag   5160

ataactacga tacgggaggg cttaccatct ggccccagtg ctgcaatgat accgcgagac   5220

ccacgctcac cggctccaga tttatcagca ataaaccagc cagccggaag ggccgagcgc   5280

agaagtggtc ctgcaacttt atccgcctcc atccagtcta ttaattgttg ccgggaagct   5340

agagtaagta gttcgccagt taatagtttg cgcaacgttg ttgccattgc tacaggcatc   5400

gtggtgtcac gctcgtcgtt tggtatggct tcattcagct ccggttccca acgatcaagg   5460

cgagttacat gatcccccat gttgtgcaaa aaagcggtta gctccttcgg tcctccgatc   5520

gttgtcagaa gtaagttggc cgcagtgtta tcactcatgg ttatggcagc actgcataat   5580

tctcttactg tcatgccatc cgtaagatgc ttttctgtga ctggtgagta ctcaaccaag   5640

tcattctgag aatagtgtat gcggcgaccg agttgctctt gcccggcgtc aatacgggat   5700

aataccgcgc cacatagcag aactttaaaa gtgctcatca ttggaaaacg ttcttcgggg   5760

cgaaaactct caaggatctt accgctgttg agatccagtt cgatgtaacc cactcgtgca   5820

cccaactgat cttcagcatc ttttactttc accagcgttt ctgggtgagc aaaaacagga   5880

aggcaaaatg ccgcaaaaaa gggaataagg gcgacacgga aatgttgaat actcatactc   5940

ttcctttttc aatattattg aagcatttat cagggttatt gtctcatgag cggatacata   6000

tttgaatgta tttagaaaaa taaacaaata ggggttccgc gcacatttcc ccgaaaagtg   6060

ccacctgacg tc                                                      6072
```

<210> SEQ ID NO 30
<211> LENGTH: 6072
<212> TYPE: DNA
<213> ORGANISM: Artificial Sequence
<220> FEATURE:
<223> OTHER INFORMATION: Plasmid containing Hs.VEGF165 R149E/R150E (6072
bp DNA circular)
<220> FEATURE:
<221> NAME/KEY: promoter
<222> LOCATION: (232)..(819)
<223> OTHER INFORMATION: /gene="pCMV"
/product="CMV promoter (-601 to +15)"
<220> FEATURE:
<221> NAME/KEY: promoter
<222> LOCATION: (863)..(882)
<223> OTHER INFORMATION: /gene="pT7"

/product="T7 promoter"
<220> FEATURE:
<221> NAME/KEY: misc_recomb
<222> LOCATION: (911)..(932)
<223> OTHER INFORMATION: /gene="attB1"
/product="attB1 recombination site"
<220> FEATURE:
<221> NAME/KEY: misc_feature
<222> LOCATION: (938)..(1513)
<223> OTHER INFORMATION: /gene="Hs.VEGF165 R149E/R150E"
<220> FEATURE:
<221> NAME/KEY: misc_recomb
<222> LOCATION: (1515)..(1536)
<223> OTHER INFORMATION: /gene="attB2"
/product="attB2 recombination site"
<220> FEATURE:
<221> NAME/KEY: misc_feature
<222> LOCATION: (1562)..(1603)
<223> OTHER INFORMATION: /gene="V5"
<220> FEATURE:
<221> NAME/KEY: polyA_site
<222> LOCATION: (1630)..(1901)
<223> OTHER INFORMATION: /gene="pA"
/product="TK polyA"
<220> FEATURE:
<221> NAME/KEY: misc_feature
<222> LOCATION: (1937)..(2365)
<223> OTHER INFORMATION: /gene="f1"
/product="f1 origin"
<220> FEATURE:
<221> NAME/KEY: promoter
<222> LOCATION: (2392)..(2700)
<223> OTHER INFORMATION: /gene="pS"
/product="SV40 promoter"
<220> FEATURE:
<221> NAME/KEY: misc_feature
<222> LOCATION: (2775)..(3569)
<223> OTHER INFORMATION: /gene="neo"
<220> FEATURE:
<221> NAME/KEY: polyA_site
<222> LOCATION: (3745)..(3875)
<223> OTHER INFORMATION: /gene="pA"
/product="SV40 polyA"
<220> FEATURE:
<221> NAME/KEY: misc_feature
<222> LOCATION: (4258)..(4931)
<223> OTHER INFORMATION: /gene="oriP"
/product="pUC origin"
<220> FEATURE:
<221> NAME/KEY: misc_feature
<222> LOCATION: (5076)..(5936)
<223> OTHER INFORMATION: /gene="bla"

<400> SEQUENCE: 30
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720

```
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagt    900
taagctatca acaagtttgt acaaaaaagt tggcaccatg aactttctgc tgagctgggt    960
gcactggtcc ctggccctgc tgctgtacct gcaccacgcc aagtggtccc aggccgctcc   1020
tatggccgag ggcggaggcc agaaccacca cgaggtggtg aaattcatgg acgtgtacca   1080
gcggagctac tgccacccca tcgagacact ggtggacatc ttccaggaat accccgacga   1140
gatcgagtac atcttcaagc ccagctgcgt gcccctgatg agatgcggcg gctgctgcaa   1200
cgacgagggc ctggaatgcg tgcccaccga ggaatccaac atcaccatgc agatcatgcg   1260
gatcaagccc caccagggcc agcatatcgg cgagatgagc ttcctgcagc acaacaagtg   1320
cgagtgccgg cccaagaagg accgggccag acaggaaaac cctgcggccc cctgcagcga   1380
ggaggaaaag cacctgttcg tgcaggaccc ccagacctgc aagtgctcct gcaagaacac   1440
cgacagccgg tgcaaggccc ggcagctgga actgaacgag cggacctgca gatgcgacaa   1500
gcccagacgg taatcaactt tcttgtacaa agtggttgat ctagagggcc cgcggttcga   1560
aggtaagcct atccctaacc ctctcctcgg tctcgattct acgcgtaccg gttagtaatg   1620
agtttaaacg gggaggcta actgaaacac ggaaggagac aataccggaa ggaacccgcg   1680
ctatgacggc aataaaaaga cagaataaaa cgcacgggtg ttgggtcgtt tgttcataaa   1740
cgcggggttc ggtcccaggg ctggcactct gtcgataccc caccgagacc ccattggggc   1800
caatacgccc gcgtttcttc cttttcccca ccccaccccc caagttcggg tgaaggccca   1860
gggctcgcag ccaacgtcgg ggcggcaggc cctgccatag cagatctgcg cagctggggc   1920
tctagggggt atccccacgc gccctgtagc ggcgcattaa gcgcggcggg tgtggtggtt   1980
acgcgcagcg tgaccgctac acttgccagc gccctagcgc ccgctccttt cgctttcttc   2040
ccttcctttc tcgccacgtt cgccggcttt ccccgtcaag ctctaaatcg ggcatccct   2100
ttagggttcc gatttagtgc tttacggcac ctcgacccca aaaaacttga ttagggtgat   2160
ggttcacgta gtgggccatc gccctgatag acggtttttc gccctttgac gttggagtcc   2220
acgttcttta atagtggact cttgttccaa actggaacaa cactcaaccc tatctcggtc   2280
tattcttttg atttataagg gattttgggg atttcggcct attggttaaa aaatgagctg   2340
atttaacaaa aatttaacgc gaattaattc tgtggaatgt gtgtcagtta gggtgtggaa   2400
agtccccagg ctccccagca ggcagaagta tgcaaagcat gcatctcaat tagtcagcaa   2460
ccaggtgtgg aaagtcccca ggctccccag caggcagaag tatgcaaagc atgcatctca   2520
attagtcagc aaccatagtc ccgcccctaa ctccgcccat cccgccccta actccgccca   2580
gttccgccca ttctccgccc catggctgac taattttttt tatttatgca gaggccgagg   2640
ccgcctctgc ctctgagcta ttccagaagt agtgaggagg cttttttgga ggcctaggct   2700
tttgcaaaaa gctcccggga gcttgtatat ccattttcgg atctgatcaa gagacaggat   2760
gaggatcgtt tcgcatgatt gaacaagatg gattgcacgc aggttctccg gccgcttggg   2820
tggagaggct attcggctat gactgggcac aacagacaat cggctgctct gatgccgccg   2880
tgttccggct gtcagcgcag gggcgcccgg ttctttttgt caagaccgac ctgtccggtg   2940
ccctgaatga actgcaggac gaggcagcgc ggctatcgtg gctggccacg acgggcgttc   3000
cttgcgcagc tgtgctcgac gttgtcactg aagcgggaag ggactggctg ctattgggcg   3060
aagtgccggg gcaggatctc ctgtcatctc accttgctcc tgccgagaaa gtatccatca   3120
```

-continued

```
tggctgatgc aatgcggcgg ctgcatacgc ttgatccggc tacctgccca ttcgaccacc   3180
aagcgaaaca tcgcatcgag cgagcacgta ctcggatgga agccggtctt gtcgatcagg   3240
atgatctgga cgaagagcat caggggctcg cgccagccga actgttcgcc aggctcaagg   3300
cgcgcatgcc cgacggcgag gatctcgtcg tgacccatgg cgatgcctgc ttgccgaata   3360
tcatggtgga aaatggccgc ttttctggat tcatcgactg tggccggctg ggtgtggcgg   3420
accgctatca ggacatagcg ttggctaccc gtgatattgc tgaagagctt ggcggcgaat   3480
gggctgaccg cttcctcgtg ctttacggta tcgccgctcc cgattcgcag cgcatcgcct   3540
tctatcgcct tcttgacgag ttcttctgag cgggactctg gggttcgcga aatgaccgac   3600
caagcgacgc ccaacctgcc atcacgagat ttcgattcca ccgccgcctt ctatgaaagg   3660
ttgggcttcg gaatcgtttt ccgggacgcc ggctggatga tcctccagcg cggggatctc   3720
atgctggagt tcttcgccca ccccaacttg tttattgcag cttataatgg ttacaaataa   3780
agcaatagca tcacaaattt cacaaataaa gcattttttt cactgcattc tagttgtggt   3840
ttgtccaaac tcatcaatgt atcttatcat gtctgtatac cgtcgacctc tagctagagc   3900
ttggcgtaat catggtcata gctgtttcct gtgtgaaatt gttatccgct cacaattcca   3960
cacaacatac gagccggaag cataaagtgt aaagcctggg gtgcctaatg agtgagctaa   4020
ctcacattaa ttgcgttgcg ctcactgccc gctttccagt cgggaaacct gtcgtgccag   4080
ctgcattaat gaatcggcca acgcgcgggg agaggcggtt tgcgtattgg gcgctcttcc   4140
gcttcctcgc tcactgactc gctgcgctcg gtcgttcggc tgcggcgagc ggtatcagct   4200
cactcaaagg cggtaatacg gttatccaca gaatcagggg ataacgcagg aaagaacatg   4260
tgagcaaaag gccagcaaaa ggccaggaac cgtaaaaagg ccgcgttgct ggcgtttttc   4320
cataggctcc gcccccctga cgagcatcac aaaaatcgac gctcaagtca gaggtggcga   4380
aacccgacag gactataaag ataccaggcg tttccccctg gaagctccct cgtgcgctct   4440
cctgttccga ccctgccgct taccggatac ctgtccgcct ttctcccttc gggaagcgtg   4500
gcgctttctc aatgctcacg ctgtaggtat ctcagttcgg tgtaggtcgt tcgctccaag   4560
ctgggctgtg tgcacgaacc ccccgttcag cccgaccgct gcgccttatc cggtaactat   4620
cgtcttgagt ccaacccggt aagacacgac ttatcgccac tggcagcagc cactggtaac   4680
aggattagca gagcgaggta tgtaggcggt gctacagagt tcttgaagtg gtggcctaac   4740
tacggctaca ctagaaggac agtatttggt atctgcgctc tgctgaagcc agttaccttc   4800
ggaaaaagag ttggtagctc ttgatccggc aaacaaacca ccgctggtag cggtggtttt   4860
tttgtttgca agcagcagat tacgcgcaga aaaaaaggat ctcaagaaga tcctttgatc   4920
ttttctacgg ggtctgacgc tcagtggaac gaaaactcac gttaagggat tttggtcatg   4980
agattatcaa aaaggatctt cacctagatc cttttaaatt aaaaatgaag ttttaaatca   5040
atctaaagta tatatgagta aacttggtct gacagttacc aatgcttaat cagtgaggca   5100
cctatctcag cgatctgtct atttcgttca tccatagttg cctgactccc cgtcgtgtag   5160
ataactacga tacgggaggg cttaccatct ggccccagtg ctgcaatgat accgcgagac   5220
ccacgctcac cggctccaga tttatcagca ataaaccagc cagccggaag ggccgagcgc   5280
agaagtggtc ctgcaacttt atccgcctcc atccagtcta ttaattgttg ccgggaagct   5340
agagtaagta gttcgccagt taatagtttg cgcaacgttg ttgccattgc tacaggcatc   5400
gtggtgtcac gctcgtcgtt tggtatggct tcattcagct ccggttccca acgatcaagg   5460
```

-continued

```
cgagttacat gatcccccat gttgtgcaaa aaagcggtta gctccttcgg tcctccgatc   5520

gttgtcagaa gtaagttggc cgcagtgtta tcactcatgg ttatggcagc actgcataat   5580

tctcttactg tcatgccatc cgtaagatgc ttttctgtga ctggtgagta ctcaaccaag   5640

tcattctgag aatagtgtat gcggcgaccg agttgctctt gcccggcgtc aatacgggat   5700

aataccgcgc cacatagcag aactttaaaa gtgctcatca ttggaaaacg ttcttcgggg   5760

cgaaaactct caaggatctt accgctgttg agatccagtt cgatgtaacc cactcgtgca   5820

cccaactgat cttcagcatc ttttactttc accagcgttt ctgggtgagc aaaaacagga   5880

aggcaaaatg ccgcaaaaaa gggaataagg gcgacacgga aatgttgaat actcatactc   5940

ttcctttttc aatattattg aagcatttat cagggttatt gtctcatgag cggatacata   6000

tttgaatgta tttagaaaaa taaacaaata ggggttccgc gcacatttcc ccgaaaagtg   6060

ccacctgacg tc                                                        6072


<210> SEQ ID NO 31
<211> LENGTH: 6072
<212> TYPE: DNA
<213> ORGANISM: Artificial Sequence
<220> FEATURE:
<223> OTHER INFORMATION: Plasmid containing Hs.VEGF165 R185E (6072 bp
      DNA circular)
<220> FEATURE:
<221> NAME/KEY: promoter
<222> LOCATION: (232)..(819)
<223> OTHER INFORMATION: /gene="pCMV"
      /product="CMV promoter (-601 to +15)"
<220> FEATURE:
<221> NAME/KEY: promoter
<222> LOCATION: (863)..(882)
<223> OTHER INFORMATION: /gene="pT7"
      /product="T7 promoter"
<220> FEATURE:
<221> NAME/KEY: misc_recomb
<222> LOCATION: (911)..(932)
<223> OTHER INFORMATION: /gene="attB1"
      /product="attB1 recombination site"
<220> FEATURE:
<221> NAME/KEY: misc_feature
<222> LOCATION: (938)..(1513)
<223> OTHER INFORMATION: /gene="Hs.VEGF165 R185E"
<220> FEATURE:
<221> NAME/KEY: misc_recomb
<222> LOCATION: (1515)..(1536)
<223> OTHER INFORMATION: /gene="attB2"
      /product="attB2 recombination site"
<220> FEATURE:
<221> NAME/KEY: misc_feature
<222> LOCATION: (1562)..(1603)
<223> OTHER INFORMATION: /gene="V5"
<220> FEATURE:
<221> NAME/KEY: polyA_site
<222> LOCATION: (1630)..(1901)
<223> OTHER INFORMATION: /gene="pA"
      /product="TK polyA"
      /SECDrawAs="Gene"
<220> FEATURE:
<221> NAME/KEY: misc_feature
<222> LOCATION: (1937)..(2365)
<223> OTHER INFORMATION: /gene="f1"
      /product="f1 origin"
<220> FEATURE:
<221> NAME/KEY: promoter
<222> LOCATION: (2392)..(2700)
<223> OTHER INFORMATION: /gene="pS"
      /product="SV40 promoter"
<220> FEATURE:
<221> NAME/KEY: misc_feature
<222> LOCATION: (2775)..(3569)
<223> OTHER INFORMATION: /gene="neo"
<220> FEATURE:
```

<221> NAME/KEY: polyA_site
<222> LOCATION: (3745)..(3875)
<223> OTHER INFORMATION: /gene="pA"
/product="SV40 polyA"
<220> FEATURE:
<221> NAME/KEY: misc_feature
<222> LOCATION: (4258)..(4931)
<223> OTHER INFORMATION: /gene="oriP"
/product="pUC origin"
<220> FEATURE:
<221> NAME/KEY: misc_feature
<222> LOCATION: (5076)..(5936)
<223> OTHER INFORMATION: /gene="bla"

<400> SEQUENCE: 31

```
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagt    900
taagctatca acaagtttgt acaaaaaagt tggcaccatg aactttctgc tgagctgggt    960
gcactggtcc ctggccctgc tgctgtacct gcaccacgcc aagtggtccc aggccgctcc   1020
tatggccgag ggcggaggcc agaaccacca cgaggtggtg aaattcatgg acgtgtacca   1080
gcggagctac tgccacccca tcgagacact ggtggacatc ttccaggaat accccgacga   1140
gatcgagtac atcttcaagc ccagctgcgt gcccctgatg agatgcggcg gctgctgcaa   1200
cgacgagggc ctggaatgcg tgcccaccga ggaatccaac atcaccatgc agatcatgcg   1260
gatcaagccc caccagggcc agcatatcgg cgagatgagc ttcctgcagc acaacaagtg   1320
cgagtgccgg cccaagaagg accgggccag acaggaaaac ccctgcggcc cctgcagcga   1380
gcggagaaag cacctgttcg tgcaggaccc ccagacctgc aagtgctcct gcaagaacac   1440
cgacagccgg tgcaaggccc ggcagctgga actgaacgag cggacctgcg aatgcgacaa   1500
gcccagacgg taatcaactt tcttgtacaa agtggttgat ctagagggcc cgcggttcga   1560
aggtaagcct atccctaacc ctctcctcgg tctcgattct acgcgtaccg gttagtaatg   1620
agtttaaacg ggggaggcta actgaaacac ggaaggagac aataccggaa ggaacccgcg   1680
ctatgacggc aataaaaaga cagaataaaa cgcacgggtg ttgggtcgtt tgttcataaa   1740
cgcggggttc ggtcccaggg ctggcactct gtcgataccc caccgagacc ccattggggc   1800
caatacgccc gcgtttcttc cttttcccca ccccaccccc caagttcggg tgaaggccca   1860
gggctcgcag ccaacgtcgg ggcggcaggc cctgccatag cagatctgcg cagctggggc   1920
```

-continued

```
tctagggggt atccccacgc gccctgtagc ggcgcattaa gcgcggcggg tgtggtggtt   1980
acgcgcagcg tgaccgctac acttgccagc gccctagcgc ccgctccttt cgctttcttc   2040
ccttcctttc tcgccacgtt cgccggcttt ccccgtcaag ctctaaatcg ggcatccct    2100
ttagggttcc gatttagtgc tttacggcac ctcgacccca aaaaacttga ttagggtgat   2160
ggttcacgta gtgggccatc gccctgatag acggtttttc gccctttgac gttggagtcc   2220
acgttcttta atagtggact cttgttccaa actggaacaa cactcaaccc tatctcggtc   2280
tattcttttg atttataagg gattttgggg atttcggcct attggttaaa aaatgagctg   2340
atttaacaaa aatttaacgc gaattaattc tgtggaatgt gtgtcagtta gggtgtggaa   2400
agtccccagg ctccccagca ggcagaagta tgcaaagcat gcatctcaat tagtcagcaa   2460
ccaggtgtgg aaagtcccca ggctccccag caggcagaag tatgcaaagc atgcatctca   2520
attagtcagc aaccatagtc ccgcccctaa ctccgcccat cccgccccta actccgccca   2580
gttccgccca ttctccgccc catggctgac taattttttt tatttatgca gaggccgagg   2640
ccgcctctgc ctctgagcta ttccagaagt agtgaggagg cttttttgga ggcctaggct   2700
tttgcaaaaa gctcccggga gcttgtatat ccattttcgg atctgatcaa gagacaggat   2760
gaggatcgtt tcgcatgatt gaacaagatg gattgcacgc aggttctccg gccgcttggg   2820
tggagaggct attcggctat gactgggcac aacagacaat cggctgctct gatgccgccg   2880
tgttccggct gtcagcgcag gggcgcccgg ttctttttgt caagaccgac ctgtccggtg   2940
ccctgaatga actgcaggac gaggcagcgc ggctatcgtg gctggccacg acgggcgttc   3000
cttgcgcagc tgtgctcgac gttgtcactg aagcgggaag ggactggctg ctattgggcg   3060
aagtgccggg gcaggatctc ctgtcatctc accttgctcc tgccgagaaa gtatccatca   3120
tggctgatgc aatgcggcgg ctgcatacgc ttgatccggc tacctgccca ttcgaccacc   3180
aagcgaaaca tcgcatcgag cgagcacgta ctcggatgga agccggtctt gtcgatcagg   3240
atgatctgga cgaagagcat caggggctcg cgccagccga actgttcgcc aggctcaagg   3300
cgcgcatgcc cgacggcgag gatctcgtcg tgacccatgg cgatgcctgc ttgccgaata   3360
tcatggtgga aaatggccgc ttttctggat tcatcgactg tggccggctg ggtgtggcgg   3420
accgctatca ggacatagcg ttggctaccc gtgatattgc tgaagagctt ggcggcgaat   3480
gggctgaccg cttcctcgtg ctttacggta tcgccgctcc cgattcgcag cgcatcgcct   3540
tctatcgcct tcttgacgag ttcttctgag cgggactctg gggttcgcga aatgaccgac   3600
caagcgacgc ccaacctgcc atcacgagat ttcgattcca ccgccgcctt ctatgaaagg   3660
ttgggcttcg gaatcgtttt ccgggacgcc ggctggatga tcctccagcg cggggatctc   3720
atgctggagt tcttcgccca ccccaacttg tttattgcag cttataatgg ttacaaataa   3780
agcaatagca tcacaaattt cacaaataaa gcattttttt cactgcattc tagttgtggt   3840
ttgtccaaac tcatcaatgt atcttatcat gtctgtatac cgtcgacctc tagctagagc   3900
ttggcgtaat catggtcata gctgtttcct gtgtgaaatt gttatccgct cacaattcca   3960
cacaacatac gagccggaag cataaagtgt aaagcctggg gtgcctaatg agtgagctaa   4020
ctcacattaa ttgcgttgcg ctcactgccc gctttccagt cgggaaacct gtcgtgccag   4080
ctgcattaat gaatcggcca acgcgcgggg agaggcggtt tgcgtattgg gcgctcttcc   4140
gcttcctcgc tcactgactc gctgcgctcg gtcgttcggc tgcggcgagc ggtatcagct   4200
cactcaaagg cggtaatacg gttatccaca gaatcagggg ataacgcagg aaagaacatg   4260
```

-continued

```
tgagcaaaag gccagcaaaa ggccaggaac cgtaaaaagg ccgcgttgct ggcgtttttc   4320

cataggctcc gcccccctga cgagcatcac aaaaatcgac gctcaagtca gaggtggcga   4380

aacccgacag gactataaag ataccaggcg tttccccctg gaagctccct cgtgcgctct   4440

cctgttccga ccctgccgct taccggatac ctgtccgcct ttctcccttc gggaagcgtg   4500

gcgctttctc aatgctcacg ctgtaggtat ctcagttcgg tgtaggtcgt tcgctccaag   4560

ctgggctgtg tgcacgaacc ccccgttcag cccgaccgct gcgccttatc cggtaactat   4620

cgtcttgagt ccaacccggt aagacacgac ttatcgccac tggcagcagc cactggtaac   4680

aggattagca gagcgaggta tgtaggcggt gctacagagt tcttgaagtg gtggcctaac   4740

tacggctaca ctagaaggac agtatttggt atctgcgctc tgctgaagcc agttaccttc   4800

ggaaaaagag ttggtagctc ttgatccggc aaacaaacca ccgctggtag cggtggtttt   4860

tttgtttgca agcagcagat tacgcgcaga aaaaaaggat ctcaagaaga tcctttgatc   4920

ttttctacgg ggtctgacgc tcagtggaac gaaaactcac gttaagggat tttggtcatg   4980

agattatcaa aaaggatctt cacctagatc cttttaaatt aaaaatgaag ttttaaatca   5040

atctaaagta tatatgagta aacttggtct gacagttacc aatgcttaat cagtgaggca   5100

cctatctcag cgatctgtct atttcgttca tccatagttg cctgactccc cgtcgtgtag   5160

ataactacga tacgggaggg cttaccatct ggccccagtg ctgcaatgat accgcgagac   5220

ccacgctcac cggctccaga tttatcagca ataaaccagc cagccggaag ggccgagcgc   5280

agaagtggtc ctgcaacttt atccgcctcc atccagtcta ttaattgttg ccgggaagct   5340

agagtaagta gttcgccagt taatagtttg cgcaacgttg ttgccattgc tacaggcatc   5400

gtggtgtcac gctcgtcgtt tggtatggct tcattcagct ccggttccca acgatcaagg   5460

cgagttacat gatcccccat gttgtgcaaa aaagcggtta gctccttcgg tcctccgatc   5520

gttgtcagaa gtaagttggc cgcagtgtta tcactcatgg ttatggcagc actgcataat   5580

tctcttactg tcatgccatc cgtaagatgc ttttctgtga ctggtgagta ctcaaccaag   5640

tcattctgag aatagtgtat gcggcgaccg agttgctctt gcccggcgtc aatacgggat   5700

aataccgcgc cacatagcag aactttaaaa gtgctcatca ttggaaaacg ttcttcgggg   5760

cgaaaactct caaggatctt accgctgttg agatccagtt cgatgtaacc cactcgtgca   5820

cccaactgat cttcagcatc ttttactttc accagcgttt ctgggtgagc aaaaacagga   5880

aggcaaaatg ccgcaaaaaa gggaataagg gcgacacgga aatgttgaat actcatactc   5940

ttcctttttc aatattattg aagcatttat cagggttatt gtctcatgag cggatacata   6000

tttgaatgta tttagaaaaa taaacaaata ggggttccgc gcacatttcc ccgaaaagtg   6060

ccacctgacg tc                                                       6072
```

<210> SEQ ID NO 32
<211> LENGTH: 6072
<212> TYPE: DNA
<213> ORGANISM: Artificial Sequence
<220> FEATURE:
<223> OTHER INFORMATION: Plasmid containing Hs.VEGF165 R150E (6072 bp DNA circular)
<220> FEATURE:
<221> NAME/KEY: promoter
<222> LOCATION: (232)..(819)
<223> OTHER INFORMATION: /gene="pCMV" /product="CMV promoter (-601 to +15)"
<220> FEATURE:
<221> NAME/KEY: promoter
<222> LOCATION: (863)..(882)
<223> OTHER INFORMATION: /gene="pT7"

/product="T7 promoter"
<220> FEATURE:
<221> NAME/KEY: misc_recomb
<222> LOCATION: (911)..(932)
<223> OTHER INFORMATION: /gene="attB1"
/product="attB1 recombination site"
<220> FEATURE:
<221> NAME/KEY: misc_feature
<222> LOCATION: (938)..(1513)
<223> OTHER INFORMATION: /gene="Hs.VEGF165 R150E"
<220> FEATURE:
<221> NAME/KEY: misc_recomb
<222> LOCATION: (1515)..(1536)
<223> OTHER INFORMATION: /gene="attB2"
/product="attB2 recombination site"
<220> FEATURE:
<221> NAME/KEY: misc_feature
<222> LOCATION: (1562)..(1603)
<223> OTHER INFORMATION: /gene="V5"
<220> FEATURE:
<221> NAME/KEY: polyA_site
<222> LOCATION: (1630)..(1901)
<223> OTHER INFORMATION: /gene="pA"
/product="TK polyA"
<220> FEATURE:
<221> NAME/KEY: misc_feature
<222> LOCATION: (1937)..(2365)
<223> OTHER INFORMATION: /gene="f1"
/product="f1 origin"
<220> FEATURE:
<221> NAME/KEY: promoter
<222> LOCATION: (2392)..(2700)
<223> OTHER INFORMATION: /gene="pS"
/product="SV40 promoter"
<220> FEATURE:
<221> NAME/KEY: misc_feature
<222> LOCATION: (2775)..(3569)
<223> OTHER INFORMATION: /gene="neo"
<220> FEATURE:
<221> NAME/KEY: polyA_site
<222> LOCATION: (3745)..(3875)
<223> OTHER INFORMATION: /gene="pA"
/product="SV40 polyA"
<220> FEATURE:
<221> NAME/KEY: misc_feature
<222> LOCATION: (4258)..(4931)
<223> OTHER INFORMATION: /gene="oriP"
/product="pUC origin"
<220> FEATURE:
<221> NAME/KEY: misc_feature
<222> LOCATION: (5076)..(5936)
<223> OTHER INFORMATION: /gene="bla"

<400> SEQUENCE: 32
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720

-continued

```
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagt    900
taagctatca acaagtttgt acaaaaaagt tggcaccatg aactttctgc tgagctgggt    960
gcactggtcc ctggccctgc tgctgtacct gcaccacgcc aagtggtccc aggccgctcc   1020
tatggccgag ggcggaggcc agaaccacca cgaggtggtg aaattcatgg acgtgtacca   1080
gcggagctac tgccacccca tcgagacact ggtggacatc ttccaggaat accccgacga   1140
gatcgagtac atcttcaagc ccagctgcgt gcccctgatg agatgcggcg gctgctgcaa   1200
cgacgagggc ctggaatgcg tgcccaccga ggaatccaac atcaccatgc agatcatgcg   1260
gatcaagccc caccagggcc agcatatcgg cgagatgagc ttcctgcagc acaacaagtg   1320
cgagtgccgg cccaagaagg accgggccag acaggaaaac ccctgcggcc cctgcagcga   1380
gcgggaaaag cacctgttcg tgcaggaccc ccagacctgc aagtgctcct gcaagaacac   1440
cgacagccgg tgcaaggccc ggcagctgga actgaacgag cggacctgca gatgcgacaa   1500
gcccagacgg taatcaactt tcttgtacaa agtggttgat ctagagggcc cgcggttcga   1560
aggtaagcct atccctaacc ctctcctcgg tctcgattct acgcgtaccg gttagtaatg   1620
agtttaaacg gggaggcta actgaaacac ggaaggagac aataccggaa ggaacccgcg   1680
ctatgacggc aataaaaaga cagaataaaa cgcacgggtg ttgggtcgtt tgttcataaa   1740
cgcggggttc ggtcccaggg ctggcactct gtcgataccc caccgagacc ccattggggc   1800
caatacgccc gcgtttcttc cttttcccca ccccaccccc caagttcggg tgaaggccca   1860
gggctcgcag ccaacgtcgg ggcggcaggc cctgccatag cagatctgcg cagctggggc   1920
tctagggggt atccccacgc gccctgtagc ggcgcattaa gcgcggcggg tgtggtggtt   1980
acgcgcagcg tgaccgctac acttgccagc gccctagcgc ccgctccttt cgctttcttc   2040
ccttcctttc tcgccacgtt cgccggcttt ccccgtcaag ctctaaatcg ggcatccct   2100
ttagggttcc gatttagtgc tttacggcac ctcgacccca aaaaacttga ttagggtgat   2160
ggttcacgta gtgggccatc gccctgatag acggtttttc gccctttgac gttggagtcc   2220
acgttcttta atagtggact cttgttccaa actggaacaa cactcaaccc tatctcggtc   2280
tattcttttg atttataagg gattttgggg atttcggcct attggttaaa aaatgagctg   2340
atttaacaaa aatttaacgc gaattaattc tgtggaatgt gtgtcagtta gggtgtggaa   2400
agtccccagg ctccccagca ggcagaagta tgcaaagcat gcatctcaat tagtcagcaa   2460
ccaggtgtgg aaagtcccca ggctccccag caggcagaag tatgcaaagc atgcatctca   2520
attagtcagc aaccatagtc ccgcccctaa ctccgcccat cccgccccta actccgccca   2580
gttccgccca ttctccgccc catggctgac taattttttt tatttatgca gaggccgagg   2640
ccgcctctgc ctctgagcta ttccagaagt agtgaggagg cttttttgga ggcctaggct   2700
tttgcaaaaa gctcccggga gcttgtatat ccattttcgg atctgatcaa gagacaggat   2760
gaggatcgtt tcgcatgatt gaacaagatg gattgcacgc aggttctccg gccgcttggg   2820
tggagaggct attcggctat gactgggcac aacagacaat cggctgctct gatgccgccg   2880
tgttccggct gtcagcgcag gggcgcccgg ttctttttgt caagaccgac ctgtccggtg   2940
ccctgaatga actgcaggac gaggcagcgc ggctatcgtg gctggccacg acgggcgttc   3000
cttgcgcagc tgtgctcgac gttgtcactg aagcgggaag ggactggctg ctattgggcg   3060
aagtgccggg gcaggatctc ctgtcatctc accttgctcc tgccgagaaa gtatccatca   3120
```

```
tggctgatgc aatgcggcgg ctgcatacgc ttgatccggc tacctgccca ttcgaccacc   3180
aagcgaaaca tcgcatcgag cgagcacgta ctcggatgga agccggtctt gtcgatcagg   3240
atgatctgga cgaagagcat caggggctcg cgccagccga actgttcgcc aggctcaagg   3300
cgcgcatgcc cgacggcgag gatctcgtcg tgacccatgg cgatgcctgc ttgccgaata   3360
tcatggtgga aaatggccgc ttttctggat tcatcgactg tggccggctg ggtgtggcgg   3420
accgctatca ggacatagcg ttggctaccc gtgatattgc tgaagagctt ggcggcgaat   3480
gggctgaccg cttcctcgtg ctttacggta tcgccgctcc cgattcgcag cgcatcgcct   3540
tctatcgcct tcttgacgag ttcttctgag cgggactctg gggttcgcga aatgaccgac   3600
caagcgacgc ccaacctgcc atcacgagat ttcgattcca ccgccgcctt ctatgaaagg   3660
ttgggcttcg gaatcgtttt ccgggacgcc ggctggatga tcctccagcg cggggatctc   3720
atgctggagt tcttcgccca ccccaacttg tttattgcag cttataatgg ttacaaataa   3780
agcaatagca tcacaaattt cacaaataaa gcattttttt cactgcattc tagttgtggt   3840
ttgtccaaac tcatcaatgt atcttatcat gtctgtatac cgtcgacctc tagctagagc   3900
ttggcgtaat catggtcata gctgtttcct gtgtgaaatt gttatccgct cacaattcca   3960
cacaacatac gagccggaag cataaagtgt aaagcctggg gtgcctaatg agtgagctaa   4020
ctcacattaa ttgcgttgcg ctcactgccc gctttccagt cgggaaacct gtcgtgccag   4080
ctgcattaat gaatcggcca acgcgcgggg agaggcggtt tgcgtattgg gcgctcttcc   4140
gcttcctcgc tcactgactc gctgcgctcg gtcgttcggc tgcggcgagc ggtatcagct   4200
cactcaaagg cggtaatacg gttatccaca gaatcagggg ataacgcagg aaagaacatg   4260
tgagcaaaag gccagcaaaa ggccaggaac cgtaaaaagg ccgcgttgct ggcgtttttc   4320
cataggctcc gcccccctga cgagcatcac aaaaatcgac gctcaagtca gaggtggcga   4380
aacccgacag gactataaag ataccaggcg tttccccctg gaagctccct cgtgcgctct   4440
cctgttccga ccctgccgct taccggatac ctgtccgcct ttctcccttc gggaagcgtg   4500
gcgctttctc aatgctcacg ctgtaggtat ctcagttcgg tgtaggtcgt tcgctccaag   4560
ctgggctgtg tgcacgaacc ccccgttcag cccgaccgct gcgccttatc cggtaactat   4620
cgtcttgagt ccaacccggt aagacacgac ttatcgccac tggcagcagc cactggtaac   4680
aggattagca gagcgaggta tgtaggcggt gctacagagt tcttgaagtg gtggcctaac   4740
tacggctaca ctagaaggac agtatttggt atctgcgctc tgctgaagcc agttaccttc   4800
ggaaaaagag ttggtagctc ttgatccggc aaacaaacca ccgctggtag cggtggtttt   4860
tttgtttgca agcagcagat tacgcgcaga aaaaaaggat ctcaagaaga tcctttgatc   4920
ttttctacgg ggtctgacgc tcagtggaac gaaaactcac gttaagggat tttggtcatg   4980
agattatcaa aaaggatctt cacctagatc cttttaaatt aaaaatgaag ttttaaatca   5040
atctaaagta tatatgagta aacttggtct gacagttacc aatgcttaat cagtgaggca   5100
cctatctcag cgatctgtct atttcgttca tccatagttg cctgactccc cgtcgtgtag   5160
ataactacga tacgggaggg cttaccatct ggccccagtg ctgcaatgat accgcgagac   5220
ccacgctcac cggctccaga tttatcagca ataaaccagc cagccggaag ggccgagcgc   5280
agaagtggtc ctgcaacttt atccgcctcc atccagtcta ttaattgttg ccgggaagct   5340
agagtaagta gttcgccagt taatagtttg cgcaacgttg ttgccattgc tacaggcatc   5400
gtggtgtcac gctcgtcgtt tggtatggct tcattcagct ccggttccca acgatcaagg   5460
```

cgagttacat gatcccccat gttgtgcaaa aaagcggtta gctccttcgg tcctccgatc 5520
gttgtcagaa gtaagttggc cgcagtgtta tcactcatgg ttatggcagc actgcataat 5580
tctcttactg tcatgccatc cgtaagatgc ttttctgtga ctggtgagta ctcaaccaag 5640
tcattctgag aatagtgtat gcggcgaccg agttgctctt gcccggcgtc aatacgggat 5700
aataccgcgc cacatagcag aactttaaaa gtgctcatca ttggaaaacg ttcttcgggg 5760
cgaaaactct caaggatctt accgctgttg agatccagtt cgatgtaacc cactcgtgca 5820
cccaactgat cttcagcatc ttttactttc accagcgttt ctgggtgagc aaaaacagga 5880
aggcaaaatg ccgcaaaaaa gggaataagg gcgacacgga aatgttgaat actcatactc 5940
ttcctttttc aatattattg aagcatttat cagggttatt gtctcatgag cggatacata 6000
tttgaatgta tttagaaaaa taaacaaata ggggttccgc gcacatttcc ccgaaaagtg 6060
ccacctgacg tc 6072

<210> SEQ ID NO 33
<211> LENGTH: 6072
<212> TYPE: DNA
<213> ORGANISM: Artificial Sequence
<220> FEATURE:
<223> OTHER INFORMATION: Plasmid containing Hs.VEGF165 R149E (6072 bp
DNA circular)
<220> FEATURE:
<221> NAME/KEY: promoter
<222> LOCATION: (232)..(819)
<223> OTHER INFORMATION: /gene="pCMV"
/product="CMV promoter (-601 to +15)"
<220> FEATURE:
<221> NAME/KEY: promoter
<222> LOCATION: (863)..(882)
<223> OTHER INFORMATION: /gene="pT7"
/product="T7 promoter"
<220> FEATURE:
<221> NAME/KEY: misc_recomb
<222> LOCATION: (911)..(932)
<223> OTHER INFORMATION: /gene="attB1"
/product="attB1 recombination site"
<220> FEATURE:
<221> NAME/KEY: misc_feature
<222> LOCATION: (938)..(1513)
<223> OTHER INFORMATION: /gene="Hs.VEGF165 R149E"
<220> FEATURE:
<221> NAME/KEY: misc_recomb
<222> LOCATION: (1515)..(1536)
<223> OTHER INFORMATION: /gene="attB2"
/product="attB2 recombination site"
<220> FEATURE:
<221> NAME/KEY: misc_feature
<222> LOCATION: (1562)..(1603)
<223> OTHER INFORMATION: /gene="V5"
<220> FEATURE:
<221> NAME/KEY: polyA_site
<222> LOCATION: (1630)..(1901)
<223> OTHER INFORMATION: /gene="pA"
/product="TK polyA"
<220> FEATURE:
<221> NAME/KEY: misc_feature
<222> LOCATION: (1937)..(2365)
<223> OTHER INFORMATION: /gene="f1"
/product="f1 origin"
<220> FEATURE:
<221> NAME/KEY: promoter
<222> LOCATION: (2392)..(2700)
<223> OTHER INFORMATION: /gene="pS"
/product="SV40 promoter"
<220> FEATURE:
<221> NAME/KEY: misc_feature
<222> LOCATION: (2775)..(3569)
<223> OTHER INFORMATION: /gene="neo"
<220> FEATURE:
<221> NAME/KEY: polyA_site

```
<222> LOCATION: (3745)..(3875)
<223> OTHER INFORMATION: /gene="pA"
      /product="SV40 polyA"
<220> FEATURE:
<221> NAME/KEY: misc_feature
<222> LOCATION: (4258)..(4931)
<223> OTHER INFORMATION: /gene="oriP"
      /product="pUC origin"
<220> FEATURE:
<221> NAME/KEY: misc_feature
<222> LOCATION: (5076)..(5936)
<223> OTHER INFORMATION: /gene="bla"

<400> SEQUENCE: 33

gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagt    900

taagctatca acaagtttgt acaaaaaagt tggcaccatg aactttctgc tgagctgggt    960

gcactggtcc ctggccctgc tgctgtacct gcaccacgcc aagtggtccc aggccgctcc   1020

tatggccgag ggcggaggcc agaaccacca cgaggtggtg aaattcatgg acgtgtacca   1080

gcggagctac tgccacccca tcgagacact ggtggacatc ttccaggaat accccgacga   1140

gatcgagtac atcttcaagc ccagctgcgt gcccctgatg agatgcggcg gctgctgcaa   1200

cgacgagggc ctggaatgcg tgcccaccga ggaatccaac atcaccatgc agatcatgcg   1260

gatcaagccc caccagggcc agcatatcgg cgagatgagc ttcctgcagc acaacaagtg   1320

cgagtgccgg cccaagaagg accgggccag acaggaaaac ccctgcggcc cctgcagcga   1380

ggagagaaag cacctgttcg tgcaggaccc ccagacctgc aagtgctcct gcaagaacac   1440

cgacagccgg tgcaaggccc ggcagctgga actgaacgag cggacctgca gatgcgacaa   1500

gcccagacgg taatcaactt tcttgtacaa agtggttgat ctagagggcc cgcggttcga   1560

aggtaagcct atccctaacc ctctcctcgg tctcgattct acgcgtaccg gttagtaatg   1620

agtttaaacg ggggaggcta actgaaacac ggaaggagac aataccggaa ggaacccgcg   1680

ctatgacggc aataaaaaga cagaataaaa cgcacgggtg ttgggtcgtt tgttcataaa   1740

cgcggggttc ggtcccaggg ctggcactct gtcgataccc caccgagacc ccattggggc   1800

caatacgccc gcgtttcttc cttttcccca ccccaccccc caagttcggg tgaaggccca   1860

gggctcgcag ccaacgtcgg ggcggcaggc cctgccatag cagatctgcg cagctggggc   1920
```

-continued

```
tctagggggt atccccacgc gccctgtagc ggcgcattaa gcgcggcggg tgtggtggtt   1980
acgcgcagcg tgaccgctac acttgccagc gccctagcgc ccgctccttt cgctttcttc   2040
ccttcctttc tcgccacgtt cgccggcttt ccccgtcaag ctctaaatcg ggcatccct    2100
ttagggttcc gatttagtgc tttacggcac ctcgacccca aaaaacttga ttagggtgat   2160
ggttcacgta gtgggccatc gccctgatag acggtttttc gccctttgac gttggagtcc   2220
acgttcttta atagtggact cttgttccaa actggaacaa cactcaaccc tatctcggtc   2280
tattcttttg atttataagg gattttgggg atttcggcct attggttaaa aaatgagctg   2340
atttaacaaa aatttaacgc gaattaattc tgtggaatgt gtgtcagtta gggtgtggaa   2400
agtccccagg ctccccagca ggcagaagta tgcaaagcat gcatctcaat tagtcagcaa   2460
ccaggtgtgg aaagtcccca ggctccccag caggcagaag tatgcaaagc atgcatctca   2520
attagtcagc aaccatagtc ccgcccctaa ctccgcccat cccgccccta actccgccca   2580
gttccgccca ttctccgccc catggctgac taattttttt tatttatgca gaggccgagg   2640
ccgcctctgc ctctgagcta ttccagaagt agtgaggagg cttttttgga ggcctaggct   2700
tttgcaaaaa gctcccggga gcttgtatat ccattttcgg atctgatcaa gagacaggat   2760
gaggatcgtt tcgcatgatt gaacaagatg gattgcacgc aggttctccg gccgcttggg   2820
tggagaggct attcggctat gactgggcac aacagacaat cggctgctct gatgccgccg   2880
tgttccggct gtcagcgcag gggcgcccgg ttctttttgt caagaccgac ctgtccggtg   2940
ccctgaatga actgcaggac gaggcagcgc ggctatcgtg gctggccacg acgggcgttc   3000
cttgcgcagc tgtgctcgac gttgtcactg aagcgggaag ggactggctg ctattgggcg   3060
aagtgccggg gcaggatctc ctgtcatctc accttgctcc tgccgagaaa gtatccatca   3120
tggctgatgc aatgcggcgg ctgcatacgc ttgatccggc tacctgccca ttcgaccacc   3180
aagcgaaaca tcgcatcgag cgagcacgta ctcggatgga agccggtctt gtcgatcagg   3240
atgatctgga cgaagagcat caggggctcg cgccagccga actgttcgcc aggctcaagg   3300
cgcgcatgcc cgacggcgag gatctcgtcg tgacccatgg cgatgcctgc ttgccgaata   3360
tcatggtgga aaatggccgc ttttctggat tcatcgactg tggccggctg ggtgtggcgg   3420
accgctatca ggacatagcg ttggctaccc gtgatattgc tgaagagctt ggcggcgaat   3480
gggctgaccg cttcctcgtg ctttacggta tcgccgctcc cgattcgcag cgcatcgcct   3540
tctatcgcct tcttgacgag ttcttctgag cgggactctg gggttcgcga aatgaccgac   3600
caagcgacgc ccaacctgcc atcacgagat ttcgattcca ccgccgcctt ctatgaaagg   3660
ttgggcttcg gaatcgtttt ccgggacgcc ggctggatga tcctccagcg cggggatctc   3720
atgctggagt tcttcgccca ccccaacttg tttattgcag cttataatgg ttacaaataa   3780
agcaatagca tcacaaattt cacaaataaa gcattttttt cactgcattc tagttgtggt   3840
ttgtccaaac tcatcaatgt atcttatcat gtctgtatac cgtcgacctc tagctagagc   3900
ttggcgtaat catggtcata gctgtttcct gtgtgaaatt gttatccgct cacaattcca   3960
cacaacatac gagccggaag cataaagtgt aaagcctggg gtgcctaatg agtgagctaa   4020
ctcacattaa ttgcgttgcg ctcactgccc gctttccagt cgggaaacct gtcgtgccag   4080
ctgcattaat gaatcggcca acgcgcgggg agaggcggtt tgcgtattgg gcgctcttcc   4140
gcttcctcgc tcactgactc gctgcgctcg gtcgttcggc tgcggcgagc ggtatcagct   4200
cactcaaagg cggtaatacg gttatccaca gaatcagggg ataacgcagg aaagaacatg   4260
tgagcaaaag gccagcaaaa ggccaggaac cgtaaaaagg ccgcgttgct ggcgtttttc   4320
```

cataggctcc gccccctga cgagcatcac aaaaatcgac gctcaagtca gaggtggcga 4380
aacccgacag gactataaag ataccaggcg tttccccctg gaagctccct cgtgcgctct 4440
cctgttccga ccctgccgct taccggatac ctgtccgcct ttctcccttc gggaagcgtg 4500
gcgctttctc aatgctcacg ctgtaggtat ctcagttcgg tgtaggtcgt tcgctccaag 4560
ctgggctgtg tgcacgaacc ccccgttcag cccgaccgct gcgccttatc cggtaactat 4620
cgtcttgagt ccaacccggt aagacacgac ttatcgccac tggcagcagc cactggtaac 4680
aggattagca gagcgaggta tgtaggcggt gctacagagt tcttgaagtg gtggcctaac 4740
tacggctaca ctagaaggac agtatttggt atctgcgctc tgctgaagcc agttaccttc 4800
ggaaaaagag ttggtagctc ttgatccggc aaacaaacca ccgctggtag cggtggtttt 4860
tttgtttgca agcagcagat tacgcgcaga aaaaaaggat ctcaagaaga tcctttgatc 4920
ttttctacgg ggtctgacgc tcagtggaac gaaaactcac gttaagggat tttggtcatg 4980
agattatcaa aaaggatctt cacctagatc cttttaaatt aaaaatgaag ttttaaatca 5040
atctaaagta tatatgagta aacttggtct gacagttacc aatgcttaat cagtgaggca 5100
cctatctcag cgatctgtct atttcgttca tccatagttg cctgactccc cgtcgtgtag 5160
ataactacga tacgggaggg cttaccatct ggccccagtg ctgcaatgat accgcgagac 5220
ccacgctcac cggctccaga tttatcagca ataaaccagc cagccggaag ggccgagcgc 5280
agaagtggtc ctgcaacttt atccgcctcc atccagtcta ttaattgttg ccgggaagct 5340
agagtaagta gttcgccagt taatagtttg cgcaacgttg ttgccattgc tacaggcatc 5400
gtggtgtcac gctcgtcgtt tggtatggct tcattcagct ccggttccca acgatcaagg 5460
cgagttacat gatcccccat gttgtgcaaa aaagcggtta gctccttcgg tcctccgatc 5520
gttgtcagaa gtaagttggc cgcagtgtta tcactcatgg ttatggcagc actgcataat 5580
tctcttactg tcatgccatc cgtaagatgc ttttctgtga ctggtgagta ctcaaccaag 5640
tcattctgag aatagtgtat gcggcgaccg agttgctctt gcccggcgtc aatacgggat 5700
aataccgcgc cacatagcag aactttaaaa gtgctcatca ttggaaaacg ttcttcgggg 5760
cgaaaactct caaggatctt accgctgttg agatccagtt cgatgtaacc cactcgtgca 5820
cccaactgat cttcagcatc ttttactttc accagcgttt ctgggtgagc aaaaacagga 5880
aggcaaaatg ccgcaaaaaa gggaataagg gcgacacgga aatgttgaat actcatactc 5940
ttcctttttc aatattattg aagcatttat cagggttatt gtctcatgag cggatacata 6000
tttgaatgta tttagaaaaa taaacaaata ggggttccgc gcacatttcc ccgaaaagtg 6060
ccacctgacg tc 6072

<210> SEQ ID NO 34
<211> LENGTH: 215
<212> TYPE: PRT
<213> ORGANISM: Homo sapiens

<400> SEQUENCE: 34

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu

```
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Glu Glu Lys His
                165                 170                 175

Leu Phe Val Gln Asp Pro Gln Thr Cys Lys Cys Ser Cys Lys Asn Thr
            180                 185                 190

Asp Ser Arg Cys Lys Ala Arg Gln Leu Glu Leu Asn Glu Arg Thr Cys
        195                 200                 205

Glu Cys Asp Lys Pro Arg Arg
    210                 215


<210> SEQ ID NO 35
<211> LENGTH: 215
<212> TYPE: PRT
<213> ORGANISM: Homo sapiens

<400> SEQUENCE: 35

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Glu Glu Lys His
                165                 170                 175

Leu Phe Val Gln Asp Pro Gln Thr Cys Lys Cys Ser Cys Lys Asn Thr
            180                 185                 190

Asp Ser Arg Cys Lys Ala Arg Gln Leu Glu Leu Asn Glu Arg Thr Cys
        195                 200                 205
```

```
Arg Cys Asp Lys Pro Arg Arg
    210                 215


<210> SEQ ID NO 36
<211> LENGTH: 215
<212> TYPE: PRT
<213> ORGANISM: Homo sapiens

<400> SEQUENCE: 36

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Arg Arg Lys His
                165                 170                 175

Leu Phe Val Gln Asp Pro Gln Thr Cys Lys Cys Ser Cys Lys Asn Thr
            180                 185                 190

Asp Ser Arg Cys Lys Ala Arg Gln Leu Glu Leu Asn Glu Arg Thr Cys
        195                 200                 205

Glu Cys Asp Lys Pro Arg Arg
    210                 215


<210> SEQ ID NO 37
<211> LENGTH: 215
<212> TYPE: PRT
<213> ORGANISM: Homo sapiens

<400> SEQUENCE: 37

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95
```

```
Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Arg Glu Lys His
                165                 170                 175

Leu Phe Val Gln Asp Pro Gln Thr Cys Lys Cys Ser Cys Lys Asn Thr
            180                 185                 190

Asp Ser Arg Cys Lys Ala Arg Gln Leu Glu Leu Asn Glu Arg Thr Cys
        195                 200                 205

Arg Cys Asp Lys Pro Arg Arg
    210                 215


<210> SEQ ID NO 38
<211> LENGTH: 215
<212> TYPE: PRT
<213> ORGANISM: Homo sapiens

<400> SEQUENCE: 38

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Glu Arg Lys His
                165                 170                 175

Leu Phe Val Gln Asp Pro Gln Thr Cys Lys Cys Ser Cys Lys Asn Thr
            180                 185                 190

Asp Ser Arg Cys Lys Ala Arg Gln Leu Glu Leu Asn Glu Arg Thr Cys
        195                 200                 205

Arg Cys Asp Lys Pro Arg Arg
    210                 215


<210> SEQ ID NO 39
<211> LENGTH: 189
<212> TYPE: PRT
<213> ORGANISM: Felis catus
```

<400> SEQUENCE: 39

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Asp Gly
            20                  25                  30

Glu His Lys Pro His Glu Val Val Lys Phe Met Asp Val Tyr Gln Arg
        35                  40                  45

Ser Tyr Cys Arg Pro Ile Glu Thr Leu Val Asp Ile Phe Gln Glu Tyr
    50                  55                  60

Pro Asp Glu Ile Glu Tyr Ile Phe Lys Pro Ser Cys Val Pro Leu Met
65                  70                  75                  80

Arg Cys Gly Gly Cys Cys Asn Asp Glu Gly Leu Glu Cys Val Pro Thr
                85                  90                  95

Glu Glu Phe Asn Ile Thr Met Gln Ile Met Arg Ile Lys Pro His Gln
            100                 105                 110

Gly Gln His Ile Gly Glu Met Ser Phe Leu Gln His Ser Lys Cys Glu
        115                 120                 125

Cys Arg Pro Lys Lys Asp Arg Ala Lys Glu Asn Pro Cys Gly Pro Cys
    130                 135                 140

Ser Glu Arg Arg Lys His Leu Phe Val Gln Asp Pro Gln Thr Cys Lys
145                 150                 155                 160

Cys Ser Cys Lys Asn Thr Asp Ser Arg Cys Lys Ala Arg Gln Leu Glu
                165                 170                 175

Leu Asn Glu Arg Thr Cys Arg Cys Asp Lys Pro Arg Arg
            180                 185

<210> SEQ ID NO 40
<211> LENGTH: 190
<212> TYPE: PRT
<213> ORGANISM: Canis familiaris

<400> SEQUENCE: 40

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Gly Gly
            20                  25                  30

Glu His Lys Pro His Glu Val Val Lys Phe Met Asp Val Tyr Gln Arg
        35                  40                  45

Ser Tyr Cys Arg Pro Ile Glu Thr Leu Val Asp Ile Phe Gln Glu Tyr
    50                  55                  60

Pro Asp Glu Ile Glu Tyr Ile Phe Lys Pro Ser Cys Val Pro Leu Met
65                  70                  75                  80

Arg Cys Gly Gly Cys Cys Asn Asp Glu Gly Leu Glu Cys Val Pro Thr
                85                  90                  95

Glu Glu Phe Asn Ile Thr Met Gln Ile Met Arg Ile Lys Pro His Gln
            100                 105                 110

Gly Gln His Ile Gly Glu Met Ser Phe Leu Gln His Ser Lys Cys Glu
        115                 120                 125

Cys Arg Pro Lys Lys Asp Arg Ala Arg Gln Glu Asn Pro Cys Gly Pro
    130                 135                 140

Cys Ser Glu Arg Arg Lys His Leu Phe Val Gln Asp Pro Gln Thr Cys
145                 150                 155                 160

Lys Cys Ser Cys Lys Asn Thr Asp Ser Arg Cys Lys Ala Arg Gln Leu
                165                 170                 175

```
Glu Leu Asn Glu Arg Thr Cys Arg Cys Asp Lys Pro Arg Arg
            180                 185                 190


<210> SEQ ID NO 41
<211> LENGTH: 190
<212> TYPE: PRT
<213> ORGANISM: Bos taurus

<400> SEQUENCE: 41

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gln Lys Pro His Glu Val Val Lys Phe Met Asp Val Tyr Gln Arg
        35                  40                  45

Ser Phe Cys Arg Pro Ile Glu Thr Leu Val Asp Ile Phe Gln Glu Tyr
    50                  55                  60

Pro Asp Glu Ile Glu Phe Ile Phe Lys Pro Ser Cys Val Pro Leu Met
65                  70                  75                  80

Arg Cys Gly Gly Cys Cys Asn Asp Glu Ser Leu Glu Cys Val Pro Thr
                85                  90                  95

Glu Glu Phe Asn Ile Thr Met Gln Ile Met Arg Ile Lys Pro His Gln
            100                 105                 110

Ser Gln His Ile Gly Glu Met Ser Phe Leu Gln His Asn Lys Cys Glu
        115                 120                 125

Cys Arg Pro Lys Lys Asp Lys Ala Arg Gln Glu Asn Pro Cys Gly Pro
    130                 135                 140

Cys Ser Glu Arg Arg Lys His Leu Phe Val Gln Asp Pro Gln Thr Cys
145                 150                 155                 160

Lys Cys Ser Cys Lys Asn Thr Asp Ser Arg Cys Lys Ala Arg Gln Leu
                165                 170                 175

Glu Leu Asn Glu Arg Thr Cys Arg Cys Asp Lys Pro Arg Arg
            180                 185                 190


<210> SEQ ID NO 42
<211> LENGTH: 190
<212> TYPE: PRT
<213> ORGANISM: Equus caballus

<400> SEQUENCE: 42

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Glu His Lys Thr His Glu Val Val Lys Phe Met Asp Val Tyr Gln Arg
        35                  40                  45

Ser Tyr Cys Arg Pro Ile Glu Thr Leu Val Asp Ile Phe Gln Glu Tyr
    50                  55                  60

Pro Asp Glu Ile Glu Tyr Ile Phe Lys Pro Ser Cys Val Pro Leu Met
65                  70                  75                  80

Arg Cys Gly Gly Cys Cys Asn Asp Glu Gly Leu Glu Cys Val Pro Thr
                85                  90                  95

Ala Glu Phe Asn Ile Thr Met Gln Ile Met Arg Ile Lys Pro His Gln
            100                 105                 110

Ser Gln His Ile Gly Glu Met Ser Phe Leu Gln His Ser Lys Cys Glu
        115                 120                 125
```

```
Cys Arg Pro Lys Lys Asp Lys Ala Arg Gln Glu Asn Pro Cys Gly Pro
    130                 135                 140

Cys Ser Glu Arg Arg Lys His Leu Phe Val Gln Asp Pro Gln Thr Cys
145                 150                 155                 160

Lys Cys Ser Cys Lys Asn Thr Asp Ser Arg Cys Lys Ala Arg Gln Leu
                165                 170                 175

Glu Leu Asn Glu Arg Thr Cys Arg Cys Asp Lys Pro Arg Arg
            180                 185                 190
```

<210> SEQ ID NO 43
<211> LENGTH: 190
<212> TYPE: PRT
<213> ORGANISM: Rattus norvegicus

<400> SEQUENCE: 43

```
Met Asn Phe Leu Leu Ser Trp Val His Trp Thr Leu Ala Leu Leu Leu
1               5                   10                  15

Tyr Leu His His Ala Lys Trp Ser Gln Ala Ala Pro Thr Thr Glu Gly
            20                  25                  30

Glu Gln Lys Ala His Glu Val Val Lys Phe Met Asp Val Tyr Gln Arg
        35                  40                  45

Ser Tyr Cys Arg Pro Ile Glu Thr Leu Val Asp Ile Phe Gln Glu Tyr
    50                  55                  60

Pro Asp Glu Ile Glu Tyr Ile Phe Lys Pro Ser Cys Val Pro Leu Met
65                  70                  75                  80

Arg Cys Ala Gly Cys Cys Asn Asp Glu Ala Leu Glu Cys Val Pro Thr
                85                  90                  95

Ser Glu Ser Asn Val Thr Met Gln Ile Met Arg Ile Lys Pro His Gln
            100                 105                 110

Ser Gln His Ile Gly Glu Met Ser Phe Leu Gln His Ser Arg Cys Glu
        115                 120                 125

Cys Arg Pro Lys Lys Asp Arg Thr Lys Pro Glu Asn His Cys Glu Pro
    130                 135                 140

Cys Ser Glu Arg Arg Lys His Leu Phe Val Gln Asp Pro Gln Thr Cys
145                 150                 155                 160

Lys Cys Ser Cys Lys Asn Thr Asp Ser Arg Cys Lys Ala Arg Gln Leu
                165                 170                 175

Glu Leu Asn Glu Arg Thr Cys Arg Cys Asp Lys Pro Arg Arg
            180                 185                 190
```

<210> SEQ ID NO 44
<211> LENGTH: 190
<212> TYPE: PRT
<213> ORGANISM: Mus musculus

<400> SEQUENCE: 44

```
Met Asn Phe Leu Leu Ser Trp Val His Trp Thr Leu Ala Leu Leu Leu
1               5                   10                  15

Tyr Leu His His Ala Lys Trp Ser Gln Ala Ala Pro Thr Thr Glu Gly
            20                  25                  30

Glu Gln Lys Ser His Glu Val Ile Lys Phe Met Asp Val Tyr Gln Arg
        35                  40                  45

Ser Tyr Cys Arg Pro Ile Glu Thr Leu Val Asp Ile Phe Gln Glu Tyr
    50                  55                  60

Pro Asp Glu Ile Glu Tyr Ile Phe Lys Pro Ser Cys Val Pro Leu Met
65                  70                  75                  80
```

-continued

Arg Cys Ala Gly Cys Cys Asn Asp Glu Ala Leu Glu Cys Val Pro Thr
85 90 95

Ser Glu Ser Asn Ile Thr Met Gln Ile Met Arg Ile Lys Pro His Gln
100 105 110

Ser Gln His Ile Gly Glu Met Ser Phe Leu Gln His Ser Arg Cys Glu
115 120 125

Cys Arg Pro Lys Lys Asp Arg Thr Lys Pro Glu Asn His Cys Glu Pro
130 135 140

Cys Ser Glu Arg Arg Lys His Leu Phe Val Gln Asp Pro Gln Thr Cys
145 150 155 160

Lys Cys Ser Cys Lys Asn Thr Asp Ser Arg Cys Lys Ala Arg Gln Leu
165 170 175

Glu Leu Asn Glu Arg Thr Cys Arg Cys Asp Lys Pro Arg Arg
180 185 190

<210> SEQ ID NO 45
<211> LENGTH: 192
<212> TYPE: PRT
<213> ORGANISM: Gallus gallus

<400> SEQUENCE: 45

Met Asn Phe Leu Leu Thr Trp Ile His Trp Gly Leu Ala Ala Leu Leu
1 5 10 15

Tyr Leu Gln Ser Ala Glu Leu Ser Lys Ala Ala Pro Ala Leu Gly Asp
20 25 30

Gly Glu Arg Lys Pro Asn Glu Val Ile Lys Phe Leu Glu Val Tyr Glu
35 40 45

Arg Ser Phe Cys Arg Thr Ile Glu Thr Leu Val Asp Ile Phe Gln Glu
50 55 60

Tyr Pro Asp Glu Val Glu Tyr Ile Phe Arg Pro Ser Cys Val Pro Leu
65 70 75 80

Met Arg Cys Ala Gly Cys Cys Gly Asp Glu Gly Leu Glu Cys Val Pro
85 90 95

Val Asp Val Tyr Asn Val Thr Met Glu Ile Ala Arg Ile Lys Pro His
100 105 110

Gln Ser Gln His Ile Ala His Met Ser Phe Leu Gln His Ser Lys Cys
115 120 125

Asp Cys Arg Pro Lys Lys Asp Val Lys Asn Lys Gln Glu Asn His Cys
130 135 140

Glu Pro Cys Ser Glu Arg Arg Lys His Leu Phe Val Gln Asp Pro Gln
145 150 155 160

Thr Cys Lys Cys Ser Cys Lys Phe Thr Asp Ser Arg Cys Lys Ser Arg
165 170 175

Gln Leu Glu Leu Asn Glu Arg Thr Cys Arg Cys Glu Lys Pro Arg Arg
180 185 190

<210> SEQ ID NO 46
<211> LENGTH: 194
<212> TYPE: PRT
<213> ORGANISM: Xenopus laevis

<400> SEQUENCE: 46

Met Asn Phe Leu Pro Ser Trp Ile His Trp Gly Leu Ala Val Leu Leu
1 5 10 15

Tyr Ile Pro Leu Ala Gln Leu Ser Gly Ala Ala Pro Met Pro Gly Glu
20 25 30

```
Gly Asp His Lys Pro Thr Glu Val Val Lys Phe Leu Lys Val Tyr Glu
        35                  40                  45

Arg Ser Met Cys Gln Val Arg Glu Ile Leu Val Asp Ile Phe Gln Glu
    50                  55                  60

Tyr Pro Glu Glu Val Glu Tyr Ile Phe Lys Pro Ser Cys Val Pro Leu
65                  70                  75                  80

Met Arg Cys Ala Gly Cys Cys Asn Asp Glu Ser Leu Glu Cys Val Ser
                85                  90                  95

Thr Glu Ser Tyr Asn Ile Thr Met Gln Ile Met Lys Ile Lys Pro His
            100                 105                 110

Ile Ser Gln His Ile Met Asp Met Ser Phe Gln Gln His Ser His Cys
        115                 120                 125

Glu Cys Arg Pro Lys Lys Glu Val Lys Ile Lys Gln Glu Asn His Cys
    130                 135                 140

Glu Pro Cys Thr Glu Lys Ser Gln Arg Lys His Leu Phe Val Gln Asp
145                 150                 155                 160

Pro Gln Thr Cys Lys Cys Ser Cys Lys Asn Thr Asp Ser Arg Cys Lys
                165                 170                 175

Thr Arg Gln Leu Glu Leu Asn Glu Arg Thr Cys Arg Cys Glu Lys Pro
            180                 185                 190

Arg Arg


<210> SEQ ID NO 47
<211> LENGTH: 191
<212> TYPE: PRT
<213> ORGANISM: Homo sapiens

<400> SEQUENCE: 47

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Ser Leu Thr Arg Lys Asp
            180                 185                 190


<210> SEQ ID NO 48
```

<211> LENGTH: 191
<212> TYPE: PRT
<213> ORGANISM: Homo sapiens

<400> SEQUENCE: 48

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190
```

<210> SEQ ID NO 49
<211> LENGTH: 209
<212> TYPE: PRT
<213> ORGANISM: Homo sapiens

<400> SEQUENCE: 49

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Pro
145                 150                 155                 160
```

```
Cys Gly Pro Cys Ser Glu Arg Arg Lys His Leu Phe Val Gln Asp Pro
                165                 170                 175

Gln Thr Cys Lys Cys Ser Cys Lys Asn Thr Asp Ser Arg Cys Lys Ala
            180                 185                 190

Arg Gln Leu Glu Leu Asn Glu Arg Thr Cys Arg Cys Asp Lys Pro Arg
        195                 200                 205

Arg
```

<210> SEQ ID NO 50
<211> LENGTH: 215
<212> TYPE: PRT
<213> ORGANISM: Homo sapiens

<400> SEQUENCE: 50

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Arg Arg Lys His
                165                 170                 175

Leu Phe Val Gln Asp Pro Gln Thr Cys Lys Cys Ser Cys Lys Asn Thr
            180                 185                 190

Asp Ser Arg Cys Lys Ala Arg Gln Leu Glu Leu Asn Glu Arg Thr Cys
        195                 200                 205

Arg Cys Asp Lys Pro Arg Arg
    210                 215
```

<210> SEQ ID NO 51
<211> LENGTH: 232
<212> TYPE: PRT
<213> ORGANISM: Homo sapiens

<400> SEQUENCE: 51

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45
```

```
Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230


<210> SEQ ID NO 52
<211> LENGTH: 371
<212> TYPE: PRT
<213> ORGANISM: Homo sapiens

<400> SEQUENCE: 52

Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ala Ser Arg Gly Gln
            20                  25                  30

Gly Pro Glu Pro Ala Pro Gly Gly Gly Val Glu Gly Val Gly Ala Arg
        35                  40                  45

Gly Val Ala Leu Lys Leu Phe Val Gln Leu Leu Gly Cys Ser Arg Phe
    50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
    130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190
```

Ala Leu Leu Leu Tyr Leu His His Ala Lys Trp Ser Gln Ala Ala Pro
195 200 205

Met Ala Glu Gly Gly Gly Gln Asn His His Glu Val Val Lys Phe Met
210 215 220

Asp Val Tyr Gln Arg Ser Tyr Cys His Pro Ile Glu Thr Leu Val Asp
225 230 235 240

Ile Phe Gln Glu Tyr Pro Asp Glu Ile Glu Tyr Ile Phe Lys Pro Ser
245 250 255

Cys Val Pro Leu Met Arg Cys Gly Gly Cys Cys Asn Asp Glu Gly Leu
260 265 270

Glu Cys Val Pro Thr Glu Glu Ser Asn Ile Thr Met Gln Ile Met Arg
275 280 285

Ile Lys Pro His Gln Gly Gln His Ile Gly Glu Met Ser Phe Leu Gln
290 295 300

His Asn Lys Cys Glu Cys Arg Pro Lys Lys Asp Arg Ala Arg Gln Glu
305 310 315 320

Asn Pro Cys Gly Pro Cys Ser Glu Arg Arg Lys His Leu Phe Val Gln
325 330 335

Asp Pro Gln Thr Cys Lys Cys Ser Cys Lys Asn Thr Asp Ser Arg Cys
340 345 350

Lys Ala Arg Gln Leu Glu Leu Asn Glu Arg Thr Cys Arg Ser Leu Thr
355 360 365

Arg Lys Asp
370

<210> SEQ ID NO 53
<211> LENGTH: 371
<212> TYPE: PRT
<213> ORGANISM: Homo sapiens

<400> SEQUENCE: 53

Met Thr Asp Arg Gln Thr Asp Thr Ala Pro Ser Pro Ser Tyr His Leu
1 5 10 15

Leu Pro Gly Arg Arg Arg Thr Val Asp Ala Ala Ala Ser Arg Gly Gln
20 25 30

Gly Pro Glu Pro Ala Pro Gly Gly Gly Val Glu Gly Val Gly Ala Arg
35 40 45

Gly Val Ala Leu Lys Leu Phe Val Gln Leu Leu Gly Cys Ser Arg Phe
50 55 60

Gly Gly Ala Val Val Arg Ala Gly Glu Ala Glu Pro Ser Gly Ala Ala
65 70 75 80

Arg Ser Ala Ser Ser Gly Arg Glu Glu Pro Gln Pro Glu Glu Gly Glu
85 90 95

Glu Glu Glu Glu Lys Glu Glu Glu Arg Gly Pro Gln Trp Arg Leu Gly
100 105 110

Ala Arg Lys Pro Gly Ser Trp Thr Gly Glu Ala Ala Val Cys Ala Asp
115 120 125

Ser Ala Pro Ala Ala Arg Ala Pro Gln Ala Leu Ala Arg Ala Ser Gly
130 135 140

Arg Gly Gly Arg Val Ala Arg Arg Gly Ala Glu Glu Ser Gly Pro Pro
145 150 155 160

His Ser Pro Ser Arg Arg Gly Ser Ala Ser Arg Ala Gly Pro Gly Arg
165 170 175

Ala Ser Glu Thr Met Asn Phe Leu Leu Ser Trp Val His Trp Ser Leu 180 185 190

Ala Leu Leu Leu Tyr Leu His His Ala Lys Trp Ser Gln Ala Ala Pro
195 200 205

Met Ala Glu Gly Gly Gly Gln Asn His His Glu Val Val Lys Phe Met
210 215 220

Asp Val Tyr Gln Arg Ser Tyr Cys His Pro Ile Glu Thr Leu Val Asp
225 230 235 240

Ile Phe Gln Glu Tyr Pro Asp Glu Ile Glu Tyr Ile Phe Lys Pro Ser
245 250 255

Cys Val Pro Leu Met Arg Cys Gly Gly Cys Cys Asn Asp Glu Gly Leu
260 265 270

Glu Cys Val Pro Thr Glu Glu Ser Asn Ile Thr Met Gln Ile Met Arg
275 280 285

Ile Lys Pro His Gln Gly Gln His Ile Gly Glu Met Ser Phe Leu Gln
290 295 300

His Asn Lys Cys Glu Cys Arg Pro Lys Lys Asp Arg Ala Arg Gln Glu
305 310 315 320

Asn Pro Cys Gly Pro Cys Ser Glu Arg Arg Lys His Leu Phe Val Gln
325 330 335

Asp Pro Gln Thr Cys Lys Cys Ser Cys Lys Asn Thr Asp Ser Arg Cys
340 345 350

Lys Ala Arg Gln Leu Glu Leu Asn Glu Arg Thr Cys Arg Cys Asp Lys
355 360 365

Pro Arg Arg
370

<210> SEQ ID NO 54
<211> LENGTH: 389
<212> TYPE: PRT
<213> ORGANISM: Homo sapiens

<400> SEQUENCE: 54

Met Thr Asp Arg Gln Thr Asp Thr Ala Pro Ser Pro Ser Tyr His Leu
1 5 10 15

Leu Pro Gly Arg Arg Arg Thr Val Asp Ala Ala Ala Ser Arg Gly Gln
20 25 30

Gly Pro Glu Pro Ala Pro Gly Gly Gly Val Glu Gly Val Gly Ala Arg
35 40 45

Gly Val Ala Leu Lys Leu Phe Val Gln Leu Leu Gly Cys Ser Arg Phe
50 55 60

Gly Gly Ala Val Val Arg Ala Gly Glu Ala Glu Pro Ser Gly Ala Ala
65 70 75 80

Arg Ser Ala Ser Ser Gly Arg Glu Glu Pro Gln Pro Glu Glu Gly Glu
85 90 95

Glu Glu Glu Glu Lys Glu Glu Glu Arg Gly Pro Gln Trp Arg Leu Gly
100 105 110

Ala Arg Lys Pro Gly Ser Trp Thr Gly Glu Ala Ala Val Cys Ala Asp
115 120 125

Ser Ala Pro Ala Ala Arg Ala Pro Gln Ala Leu Ala Arg Ala Ser Gly
130 135 140

Arg Gly Gly Arg Val Ala Arg Arg Gly Ala Glu Glu Ser Gly Pro Pro
145 150 155 160

His Ser Pro Ser Arg Arg Gly Ser Ala Ser Arg Ala Gly Pro Gly Arg
165 170 175

```
Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
    290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Pro Cys Gly Pro Cys Ser Glu Arg Arg Lys His Leu Phe
            340                 345                 350

Val Gln Asp Pro Gln Thr Cys Lys Cys Ser Cys Lys Asn Thr Asp Ser
        355                 360                 365

Arg Cys Lys Ala Arg Gln Leu Glu Leu Asn Glu Arg Thr Cys Arg Cys
    370                 375                 380

Asp Lys Pro Arg Arg
385


<210> SEQ ID NO 55
<211> LENGTH: 395
<212> TYPE: PRT
<213> ORGANISM: Homo sapiens

<400> SEQUENCE: 55

Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ala Ser Arg Gly Gln
            20                  25                  30

Gly Pro Glu Pro Ala Pro Gly Gly Gly Val Glu Gly Val Gly Ala Arg
        35                  40                  45

Gly Val Ala Leu Lys Leu Phe Val Gln Leu Leu Gly Cys Ser Arg Phe
    50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
    130                 135                 140

Arg Gly Gly Arg Val Ala Arg Arg Gly Ala Glu Glu Ser Gly Pro Pro
145                 150                 155                 160
```

His Ser Pro Ser Arg Arg Gly Ser Ala Ser Arg Ala Gly Pro Gly Arg
165 170 175

Ala Ser Glu Thr Met Asn Phe Leu Leu Ser Trp Val His Trp Ser Leu
180 185 190

Ala Leu Leu Leu Tyr Leu His His Ala Lys Trp Ser Gln Ala Ala Pro
195 200 205

Met Ala Glu Gly Gly Gly Gln Asn His His Glu Val Val Lys Phe Met
210 215 220

Asp Val Tyr Gln Arg Ser Tyr Cys His Pro Ile Glu Thr Leu Val Asp
225 230 235 240

Ile Phe Gln Glu Tyr Pro Asp Glu Ile Glu Tyr Ile Phe Lys Pro Ser
245 250 255

Cys Val Pro Leu Met Arg Cys Gly Gly Cys Cys Asn Asp Glu Gly Leu
260 265 270

Glu Cys Val Pro Thr Glu Glu Ser Asn Ile Thr Met Gln Ile Met Arg
275 280 285

Ile Lys Pro His Gln Gly Gln His Ile Gly Glu Met Ser Phe Leu Gln
290 295 300

His Asn Lys Cys Glu Cys Arg Pro Lys Lys Asp Arg Ala Arg Gln Glu
305 310 315 320

Lys Lys Ser Val Arg Gly Lys Gly Lys Gly Gln Lys Arg Lys Arg Lys
325 330 335

Lys Ser Arg Tyr Lys Ser Trp Ser Val Pro Cys Gly Pro Cys Ser Glu
340 345 350

Arg Arg Lys His Leu Phe Val Gln Asp Pro Gln Thr Cys Lys Cys Ser
355 360 365

Cys Lys Asn Thr Asp Ser Arg Cys Lys Ala Arg Gln Leu Glu Leu Asn
370 375 380

Glu Arg Thr Cys Arg Cys Asp Lys Pro Arg Arg
385 390 395

<210> SEQ ID NO 56
<211> LENGTH: 412
<212> TYPE: PRT
<213> ORGANISM: Homo sapiens

<400> SEQUENCE: 56

Met Thr Asp Arg Gln Thr Asp Thr Ala Pro Ser Pro Ser Tyr His Leu
1 5 10 15

Leu Pro Gly Arg Arg Arg Thr Val Asp Ala Ala Ala Ser Arg Gly Gln
20 25 30

Gly Pro Glu Pro Ala Pro Gly Gly Gly Val Glu Gly Val Gly Ala Arg
35 40 45

Gly Val Ala Leu Lys Leu Phe Val Gln Leu Leu Gly Cys Ser Arg Phe
50 55 60

Gly Gly Ala Val Val Arg Ala Gly Glu Ala Glu Pro Ser Gly Ala Ala
65 70 75 80

Arg Ser Ala Ser Ser Gly Arg Glu Glu Pro Gln Pro Glu Glu Gly Glu
85 90 95

Glu Glu Glu Glu Lys Glu Glu Glu Arg Gly Pro Gln Trp Arg Leu Gly
100 105 110

Ala Arg Lys Pro Gly Ser Trp Thr Gly Glu Ala Ala Val Cys Ala Asp
115 120 125

Ser Ala Pro Ala Ala Arg Ala Pro Gln Ala Leu Ala Arg Ala Ser Gly

```
    130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
    290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Tyr Val Gly Ala Arg Cys Cys
            340                 345                 350

Leu Met Pro Trp Ser Leu Pro Gly Pro His Pro Cys Gly Pro Cys Ser
        355                 360                 365

Glu Arg Arg Lys His Leu Phe Val Gln Asp Pro Gln Thr Cys Lys Cys
    370                 375                 380

Ser Cys Lys Asn Thr Asp Ser Arg Cys Lys Ala Arg Gln Leu Glu Leu
385                 390                 395                 400

Asn Glu Arg Thr Cys Arg Cys Asp Lys Pro Arg Arg
                405                 410


<210> SEQ ID NO 57
<211> LENGTH: 191
<212> TYPE: PRT
<213> ORGANISM: Homo sapiens

<400> SEQUENCE: 57

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95
```

```
Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190


<210> SEQ ID NO 58
<211> LENGTH: 191
<212> TYPE: PRT
<213> ORGANISM: Homo sapiens

<400> SEQUENCE: 58

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190


<210> SEQ ID NO 59
<211> LENGTH: 232
<212> TYPE: PRT
<213> ORGANISM: Homo sapiens

<400> SEQUENCE: 59

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45
```

-continued

```
Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230


<210> SEQ ID NO 60
<211> LENGTH: 19
<212> TYPE: PRT
<213> ORGANISM: Homo sapiens

<400> SEQUENCE: 60

Lys Lys Ser Val Arg Gly Lys Gly Lys Gly Gln Lys Arg Lys Arg Lys
1               5                   10                  15

Lys Ser Arg


<210> SEQ ID NO 61
<211> LENGTH: 25
<212> TYPE: PRT
<213> ORGANISM: Homo sapiens

<400> SEQUENCE: 61

Lys Lys Ser Val Arg Gly Lys Gly Lys Gly Gln Lys Arg Lys Arg Lys
1               5                   10                  15

Lys Ser Arg Tyr Lys Ser Trp Ser Val
            20                  25


<210> SEQ ID NO 62
<211> LENGTH: 40
<212> TYPE: PRT
<213> ORGANISM: Homo sapiens

<400> SEQUENCE: 62

Lys Lys Ser Val Arg Gly Lys Gly Lys Gly Gln Lys Arg Lys Arg Lys
1               5                   10                  15

Lys Ser Arg Tyr Lys Ser Trp Ser Val Tyr Val Gly Ala Arg Cys Cys
            20                  25                  30

Leu Met Pro Trp Ser Leu Pro Gly
        35                  40
```

<210> SEQ ID NO 63
<211> LENGTH: 42
<212> TYPE: PRT
<213> ORGANISM: Homo sapiens

<400> SEQUENCE: 63

Lys Lys Ser Val Arg Gly Lys Gly Lys Gly Gln Lys Arg Lys Arg Lys
1 5 10 15

Lys Ser Arg Tyr Lys Ser Trp Ser Val Tyr Val Gly Ala Arg Cys Cys
20 25 30

Leu Met Pro Trp Ser Leu Pro Gly Pro His
35 40

<210> SEQ ID NO 64
<211> LENGTH: 74
<212> TYPE: PRT
<213> ORGANISM: Homo sapiens

<400> SEQUENCE: 64

Ala Arg Gln Glu Lys Lys Lys Ser Val Arg Gly Lys Gly Lys Gly Gln
1 5 10 15

Lys Arg Lys Arg Lys Lys Ser Arg Pro Cys Gly Pro Cys Ser Glu Arg
20 25 30

Arg Lys His Leu Phe Val Gln Asp Pro Gln Thr Cys Lys Cys Ser Cys
35 40 45

Lys Asn Thr Asp Ser Arg Cys Lys Ala Arg Gln Leu Glu Leu Asn Glu
50 55 60

Arg Thr Cys Arg Cys Asp Lys Pro Arg Arg
65 70

<210> SEQ ID NO 65
<211> LENGTH: 80
<212> TYPE: PRT
<213> ORGANISM: Homo sapiens

<400> SEQUENCE: 65

Ala Arg Gln Glu Lys Lys Lys Ser Val Arg Gly Lys Gly Lys Gly Gln
1 5 10 15

Lys Arg Lys Arg Lys Lys Ser Arg Tyr Lys Ser Trp Ser Val Pro Cys
20 25 30

Gly Pro Cys Ser Glu Arg Arg Lys His Leu Phe Val Gln Asp Pro Gln
35 40 45

Thr Cys Lys Cys Ser Cys Lys Asn Thr Asp Ser Arg Cys Lys Ala Arg
50 55 60

Gln Leu Glu Leu Asn Glu Arg Thr Cys Arg Cys Asp Lys Pro Arg Arg
65 70 75 80

<210> SEQ ID NO 66
<211> LENGTH: 95
<212> TYPE: PRT
<213> ORGANISM: Homo sapiens

<400> SEQUENCE: 66

Ala Arg Gln Glu Lys Lys Lys Ser Val Arg Gly Lys Gly Lys Gly Gln
1 5 10 15

Lys Arg Lys Arg Lys Lys Ser Arg Tyr Lys Ser Trp Ser Val Tyr Val
20 25 30

Gly Ala Arg Cys Cys Leu Met Pro Trp Ser Leu Pro Gly Pro Cys Gly 35 40 45

Pro Cys Ser Glu Arg Arg Lys His Leu Phe Val Gln Asp Pro Gln Thr
50 55 60

Cys Lys Cys Ser Cys Lys Asn Thr Asp Ser Arg Cys Lys Ala Arg Gln
65 70 75 80

Leu Glu Leu Asn Glu Arg Thr Cys Arg Cys Asp Lys Pro Arg Arg
85 90 95

<210> SEQ ID NO 67
<211> LENGTH: 97
<212> TYPE: PRT
<213> ORGANISM: Homo sapiens

<400> SEQUENCE: 67

Ala Arg Gln Glu Lys Lys Lys Ser Val Arg Gly Lys Gly Lys Gly Gln
1 5 10 15

Lys Arg Lys Arg Lys Lys Ser Arg Tyr Lys Ser Trp Ser Val Tyr Val
20 25 30

Gly Ala Arg Cys Cys Leu Met Pro Trp Ser Leu Pro Gly Pro His Pro
35 40 45

Cys Gly Pro Cys Ser Glu Arg Arg Lys His Leu Phe Val Gln Asp Pro
50 55 60

Gln Thr Cys Lys Cys Ser Cys Lys Asn Thr Asp Ser Arg Cys Lys Ala
65 70 75 80

Arg Gln Leu Glu Leu Asn Glu Arg Thr Cys Arg Cys Asp Lys Pro Arg
85 90 95

Arg

<210> SEQ ID NO 68
<211> LENGTH: 55
<212> TYPE: PRT
<213> ORGANISM: Homo sapiens

<400> SEQUENCE: 68

Ala Arg Gln Glu Asn Pro Cys Gly Pro Cys Ser Glu Arg Arg Lys His
1 5 10 15

Leu Phe Val Gln Asp Pro Gln Thr Cys Lys Cys Ser Cys Lys Asn Thr
20 25 30

Asp Ser Arg Cys Lys Ala Arg Gln Leu Glu Leu Asn Glu Arg Thr Cys
35 40 45

Arg Ser Leu Thr Arg Lys Asp
50 55

<210> SEQ ID NO 69
<211> LENGTH: 6
<212> TYPE: PRT
<213> ORGANISM: Homo sapiens

<400> SEQUENCE: 69

Ser Leu Thr Arg Lys Asp
1 5

METHODS FOR USE OF VASCULAR ENDOTHELIAL GROWTH FACTOR ANTAGONISTS

CROSS-REFERENCE TO RELATED APPLICATION

This application is a 35 U.S.C. §371 national phase application of PCT/US2013/038506 (WO2013/163606), filed on Apr. 26, 2013, entitled "VASCULAR ENDOTHELIAL GROWTH FACTOR ANTAGONISTS AND METHODS FOR THEIR USE", which application claims priority to and the benefit of U.S. Provisional Application No. 61/639,230, filed Apr. 27, 2012, entitled "VASCULAR ENDOTHELIAL GROWTH FACTOR ANTAGONISTS AND METHODS FOR THEIR USE", the disclosures of which are incorporated herein by reference in their entirety.

STATEMENT REGARDING GOVERNMENT RIGHTS

The instant application and the invention(s) described herein are the property of the United States Government. The work related to this patent application was funded, at least in part by, the National Institutes of Health, as part of project 1ZIABC011124.

SEQUENCE LISTING

The Sequence Listing text file attached hereto, created Apr. 22, 2013, size 156 kilobytes, and filed herewith as file name "6137NCI31PCT_SEQ_20120427_ST25. txt" is incorporated herein by reference in its entirety.

BACKGROUND

Vascular endothelial growth factor-A (VEGF-A) is an essential regulator of angiogenesis during embryogenesis and adulthood, and mediates pathological angiogenesis in many diseases, including cancer. VEGF-A signals through the receptor tyrosine kinases VEGFR1 and VEGFR2; the VEGFA gene encodes multiple VEGF-A isoforms, all of which bind VEGFR1 and VEGFR2, but differ in their capacity to bind to heparan sulfate proteoglycans (HSP) also present on target cells. HSP binding plays a critical role of VEGF-A signaling; mice engineered to express only a non-HSP binding isoform display defective microvessel branching and frequently die shortly after birth.

Vascular endothelial growth factor is a member of the PDGF family that is characterized by the presence of eight conserved cysteine residues and a cystine knot structure. Humans express alternately spliced isoforms of 121, 145, 165, 183, 189, and 206 amino acids in length. VEGF165 appears to be the most abundant and potent isoform, followed by VEGF121 and VEGF189. Isoforms other than VEGF121 contain basic heparin binding regions and are not freely diffusible.

Human VEGF165 shares 88% amino acid sequence identity with corresponding regions of mouse and rat, 96% with porcine, 95% with canine, and 93% with feline, equine and bovine VEGF, respectively. VEGF binds the type I transmembrane receptor tyrosine kinases VEGF R1 (also called Flt1) and VEGF R2 (Flk1/KDR) on endothelial cells. Although VEGF affinity is highest for binding to VEGF R1, VEGF R2 appears to be the primary mediator of VEGF angiogenic activity.

Within the carboxyl terminal domain of the VEGF165 isoform, amino acids R123, R124, and R159 are reportedly critical for HSP binding. However, it is noted that replacement of these amino acids with alanine causes reduced binding of VEGF 165 to VEGFR1 but does not affect binding of VEGF 165 to VEGFR2. Importantly, in an in vitro assay which assesses angiogenic activity, alanine substitution mutants of native VEGF showed the same ability to enhance angiogenesis as native VEGF. Alanine substituted mutants also showed reduced affinity for heparin, heparan sulfate proteoglycans, and for the VEGFR2 coreceptor, NRP1. VEGFR2 has been identified as the key signaling receptor that mediates the proliferative and migratory effects of VEGF. Alanine mutants were found to possess an angiogenic activity as potent as that of native VEGF154 (mouse), indicating that VEGF carboxyl-terminal domain is not directly involved in VEGFR2 binding.

The critical role of VEGF signaling in many human cancers, particularly as a driver of tumor growth and metastasis, for example, has made VEGF and its receptors important anti-cancer drug targets. VEGF signaling blockade has been achieved using VEGFR ATP binding site antagonists and VEGF neutralizing antibodies; each of these approaches has features as well as limitations. Neutralizing antibodies are highly selective for their intended target, e.g. VEGF, and have few, if any, off-target effects. ATP binding antagonists, in contrast, are often cheaper to manufacture than antibodies, but are less selective for their intended target and off-target toxicities are frequently associated with their use. Biological antagonists derived from the native protein ligand, e.g. VEGF, can be more cost-effective to produce than larger antibody molecules, yet possess a comparable level of target selectivity. A receptor antagonist would be desirable because a receptor antagonist would bind to the receptor, and would be likely to exert inhibitor action even where receptor activation is independent of VEGF binding. Bevacizumab (Avastin) is the major biological VEGF antagonist anti-cancer therapeutic approved so far by the US FDA. Bevacizumab is expensive to produce because it requires mammalian expression for manufacture, the most expensive recombinant expression system used in protein production. Aflibercept, a VEGFR fusion protein has US FDA approval for the treatment of colorectal cancer and wet macular degeneration. Among existing VEGF antagonists, Aflibercept has a unique target spectrum, although it too is manufactured using a mammalian cell expression system. It would be desirable to manufacture such an antagonist in a less expensive system, for example, via *P. pastoris.*

SUMMARY

In one embodiment, the present invention includes a method for treating a disease characterized by pathological angiogenesis. This method includes administering to a patient in need thereof a pharmaceutically effective amount of a vascular endothelial cell growth factor (VEGF) polypeptide comprising a variant C-terminal heparin binding domain and a native receptor tyrosine kinase binding domain. In one embodiment the polypeptide comprises a variant C-terminal heparin domain. This variant polypeptide has one or more amino acid alternations from a native VEGF polypeptide designed to occupy the receptor and repel and/or reduce binding affinity to heparin, rather than bind heparin and/or heparan sulfate containing proteoglycans with high affinity, as does native VEGF. In one embodiment, the affinity of the variant polypeptide for both VEGFR-1

(FLT-1) and VEGFR-2 (KDR/FLK-1) is substantially maintained in comparison to said native VEGF.

In another embodiment, the variant polypeptide antagonizes KDR signal activation. In one embodiment, the native VEGF polypeptide can be one of the following: SEQ ID NO:1, SEQ ID NO:2, SEQ ID NO:3, or SEQ ID NO:4.

The present invention includes variant VEGF polypeptides. A vascular endothelial cell growth factor (VEGF) variant polypeptide includes polypeptides comprising a variant C-terminal heparin binding domain, and a native receptor tyrosine kinase binding domain, wherein said variant polypeptide has one or more amino acid alternations from a native VEGF polypeptide, wherein said variant polypeptide binds heparin at a lower affinity than and/or repels heparin as compared to said native VEGF, and wherein the affinity of the variant polypeptide for both VEGFR-1 (FLT-1) and VEGFR-2 (KDR/FLK-1) is substantially maintained in comparison to said native VEGF, and wherein said variant polypeptide antagonizes KDR signal activation. In one embodiment the polypeptide comprises a variant C-terminal heparin domain.

A variant polypeptide of the invention can be any of the following: a polypeptide which includes SEQ ID NO:25 wherein the amino acid of at least one of positions 149, 150, and 185 of SEQ ID NO:25 is an acidic amino acid, a polypeptide comprising SEQ ID NO:26 wherein the amino acid of at least one of positions 123, 124, and 159 of SEQ ID NO:26 is an acidic amino acid, or a polypeptide comprising SEQ ID NO:27 wherein the amino acid of at least one of positions 13, 14, and 49 of SEQ ID NO:27 is an acidic amino acid; or a polypeptide having at least 95% identity to any of the above polypeptides and having the ability to antagonize KDR signal activation. In one embodiment, the acidic amino acid is E. In another embodiment, the variant polypeptide can be any of the following: a polypeptide comprising SEQ ID NO:25 wherein the amino acid at positions 149, 150, and 185 of SEQ ID NO:25 is an acidic amino acid, a polypeptide comprising SEQ ID NO:26 wherein the amino acid at positions 123, 124, and 159 of SEQ ID NO:26 is an acidic amino acid, or a polypeptide comprising SEQ ID NO:27 wherein the amino acid at positions 13, 14, and 49 of SEQ ID NO:27 is an acidic amino acid; or a polypeptide having at least 95% identity to any of the preceding polypeptides and having the ability to antagonize KDR signal activation. In one embodiment, the acidic amino acid is E.

In another embodiment, the variant polypeptide of the invention can be any of the following: a polypeptide including SEQ ID NO:6, SEQ ID NO:7, SEQ ID NO:8, SEQ ID NO:10, SEQ ID NO:11, SEQ ID NO:12, SEQ ID NO:14, SEQ ID NO:15, SEQ ID NO:16, SEQ ID NO:18, SEQ ID NO:19, SEQ ID NO:20, SEQ ID NO:22, SEQ ID NO:23, or SEQ ID NO:24; and a polypeptide having at least 95% identity to a preceding polypeptide and having the ability to antagonize KDR signal activation.

The disease characterized by pathological angiogenesis may be cancer or ocular disease. The ocular disease may be, macular degeneration, or diabetic retinopathy. The cancer may be a metastatic cancer. Other diseases characterized by pathological angiogenesis are also contemplated and described elsewhere in this patent specification.

In another embodiment, the present invention includes a method for creating a polypeptide capable of inhibiting angiogenesis which comprises the steps of providing a native VEGF comprising a variant C-terminal heparin binding domain and a native receptor tyrosine kinase binding domain and modifying said native VEGF to form a variant VEGF polypeptide. The variant VEGF polypeptide includes (1) SEQ ID NO: 25, SEQ ID NO: 26 or SEQ ID NO:27 where Xaa is an acidic amino acid; and (2) a polypeptide having at least 95% identity to a polypeptide of (1) and having the ability to antagonize KDR signal activation. In one embodiment the polypeptide comprises a variant C-terminal heparin domain.

The present invention also includes polynucleotides. In one embodiment, the polynucleotides of the present invention include a polynucleotide that encodes a vascular endothelial cell growth factor (VEGF) variant polypeptide comprising a C-terminal heparin binding domain, wherein said variant polypeptide has one or more amino acid alternations from a native VEGF polypeptide, wherein said variant polypeptide binds heparin at a lower affinity than and/or repels heparin as compared to said native VEGF, and wherein the affinity of the variant polypeptide for both VEGFR-1 (FLT-1) and VEGFR-2 (KDR/FLK-1) is substantially maintained in comparison to said native VEGF, and wherein said variant polypeptide antagonizes KDR signal activation.

In one embodiment, the polynucleotide can include the following polynucleotides: a polynucleotide which encodes at least one of the following polypeptides: SEQ ID NO:6, SEQ ID NO:7, SEQ ID NO:8, SEQ ID NO:10, SEQ ID NO:11, SEQ ID NO:12, SEQ ID NO:14, SEQ ID NO:15, SEQ ID NO:16, SEQ ID NO:18, SEQ ID NO:19, SEQ ID NO:20, SEQ ID NO:22, SEQ ID NO:23, SEQ ID NO:24, SEQ ID NO:25, SEQ ID NO:26, and SEQ ID NO:27; and a polynucleotide having at least 95% identity to a preceding polypeptide and encoding a polypeptide having the ability to antagonize KDR signal activation. In another embodiment, the polynucleotide can be any of the following: a polynucleotide comprising, SEQ ID NO:5, SEQ ID NO:9, SEQ ID NO:13, SEQ ID NO:17, SEQ ID NO:21, SEQ ID NO:29, SEQ ID NO:30, SEQ ID NO:31, SEQ ID NO:32, and SEQ ID NO:33; and a polynucleotide having at least 95% identity any of the preceding polynucleotides and encoding a polypeptide having the ability to antagonize KDR signal activation. Other embodiments include those where the coding sequence found in SEQ ID NO: 29, SEQ ID NO: 30, SEQ ID NO: 31, SEQ ID NO: 32 or SEQ ID NO: 33 (base pairs 938-1513 in each SEQ ID) is replaced with base pairs 1016-1513 of any of these SEQ ID's which correspond to the mature VEGF isoform or base pairs 1346-1513 of any of these SEQ IDs which correspond to the heparin binding domain. Embodiments having at least 95% sequence identity with these polynucleotides are also contemplated.

BRIEF DESCRIPTION OF THE DRAWINGS

FIGS. 1A-1C. Conservation of primary HS binding residues in VEGF165 HS binding domain.

FIG. 1A Amino acid sequences, in single letter code, of VEGF165 protein precursors from the vertebrate species and GenBank accession files indicated at right. The multiple alignment was created using the BLAST MULTIALIGN tool (Altschul et al., 1990). Note that all GenBank sequence files of VEGF-A precursors include the signal peptide sequence as residues 1-26, indicated by the box. Proteolytic cleavage removes the signal peptide from mature VEGF-A proteins, yielding an amino-terminus indicated by the arrow. The names of various VEGF-A isoforms, such as VEGF165, VEGF189, etc., are derived from the number of amino acid residues in the mature protein, after cleavage of the signal peptide. Thus the VEGF165 precursor contains 191 residues, but the mature VEGF165 protein contains precursor residues 27-191, or 165. The GenBank numbering scheme is not frequently used in the VEGF literature; instead, residue 27 of the precursor is most often referred to as residue 1. The heparin binding domain (HBD) sequence is indicated by the box. Positions highlighted in the HBD indicate primary HS binding sites as determined previously (Krilleke et al., 2007).

FIG. 1B. Schematic diagram of Group 1 of mature VEGF165 protein isoforms, which contain an amino-terminal VEGR receptor tyrosine kinase (RTK) binding region and a carboxy-terminal heparin binding domain (HBD). Numbering of amino acid residues in the mature VEGF165 proteins of Group 1 is shown above the schematic; the amino acid sequence and critical HS binding residues in the HBD are identified below, numbered relative to their position in the HBD alone. For the group of VEGFA isoforms depicted in this Figure, identifying the critical HS binding residues as R13, R14 and R49 of the HBD provides an unambiguous and uniform means of identification in all VEGF-A heparin binding isoforms, independent of total protein length or HBD position.

FIG. 1C. FIG. 1C shows an alignment between heparin binding domains of a second group, Group 2, which contains heparin binding domains with insertions. As can be seen from both the alignment and the schematics, the HBD insertions in Group 2 change the numbering of the critical HS binding residues (13,14,49 in Group 1) to 31,32,67 in Group 2a; 37,38,73 in Group 2b; and 54,55,90 in Group 2c.

FIG. 2. VEGF165 HS binding domain structure. Models depicting the high resolution three dimensional structure of the VEGF165 HS binding domain determined previously by NMR spectrometry (Fairbrother et al., 1998; Zhou et al., 1998) (Protein Data Bank codes 2HGF and 1KMX). Models were created using PyMOL (The PyMOL Molecular Graphics System, Version 1.3, Schrödinger, LLC); the peptide backbone folding pattern (top and middle panels) show amino terminal residues, carboxyl terminal residues, and the positions (top panel) and side chains (middle panel) of primary HS binding residues. Numbering of the critical HS binding residues is in the context of the HBD alone, as detailed in FIG. 1B. The space fill model (lower panel) show the positive surface charge distribution of primary HS binding residues in.

A. Mean VEGF165 protein content (ng/mg total cell protein+/−SD; n=3) in 24 h conditioned media (clear bars) or low-volume detergent extracts (gray bars) prepared from 293/KDR cells transfected with plasmids encoding empty vector (empty), VEGF165 WT (WT), or VEGF165 3S (3S).

B. VEGF165 3S protein (3S; left) in 24 h conditioned media prepared from VEGF165 3S transfected 293/KDR cells visualized after SDS-PAGE and immunoblotting. Three amounts (ng) of purified VEGF165 WT were loaded on the right for reference (arrow).

C. Saturation binding of KDR ectodomain-IgG fusion protein to VEGF165 WT (squares) or VEGF165 3S proteins (circles) in vitro. Values are mean KDR bound (ng/ml)+/−SD (n=3).

D. Mean phospho-KDR level (signal intensity+/−SD; n=3) in 293/KDR cells stably transfected with plasmids encoding empty vector (empty; unfilled bar), VEGF165 WT (WT; light gray bar), VEGF165 3S (3S; dark gray bar), or empty vector cells treated with purified VEGF165 WT protein (2.5 nM) for 20 min (+VEGF; black bar).

E. Growth rate (mean cell number+/−SD, n=3) of cultured 293/KDR cells stably transfected with plasmids encoding empty vector (circles), VEGF165 WT (squares), or VEGF165 3S (triangles).

F. Soft agar colony formation by 239/KDR cells stably transfected with empty vector, (left), VEGF 3S expression plasmid (middle), or VEGF WT expression plasmid (right).

Figure 5:
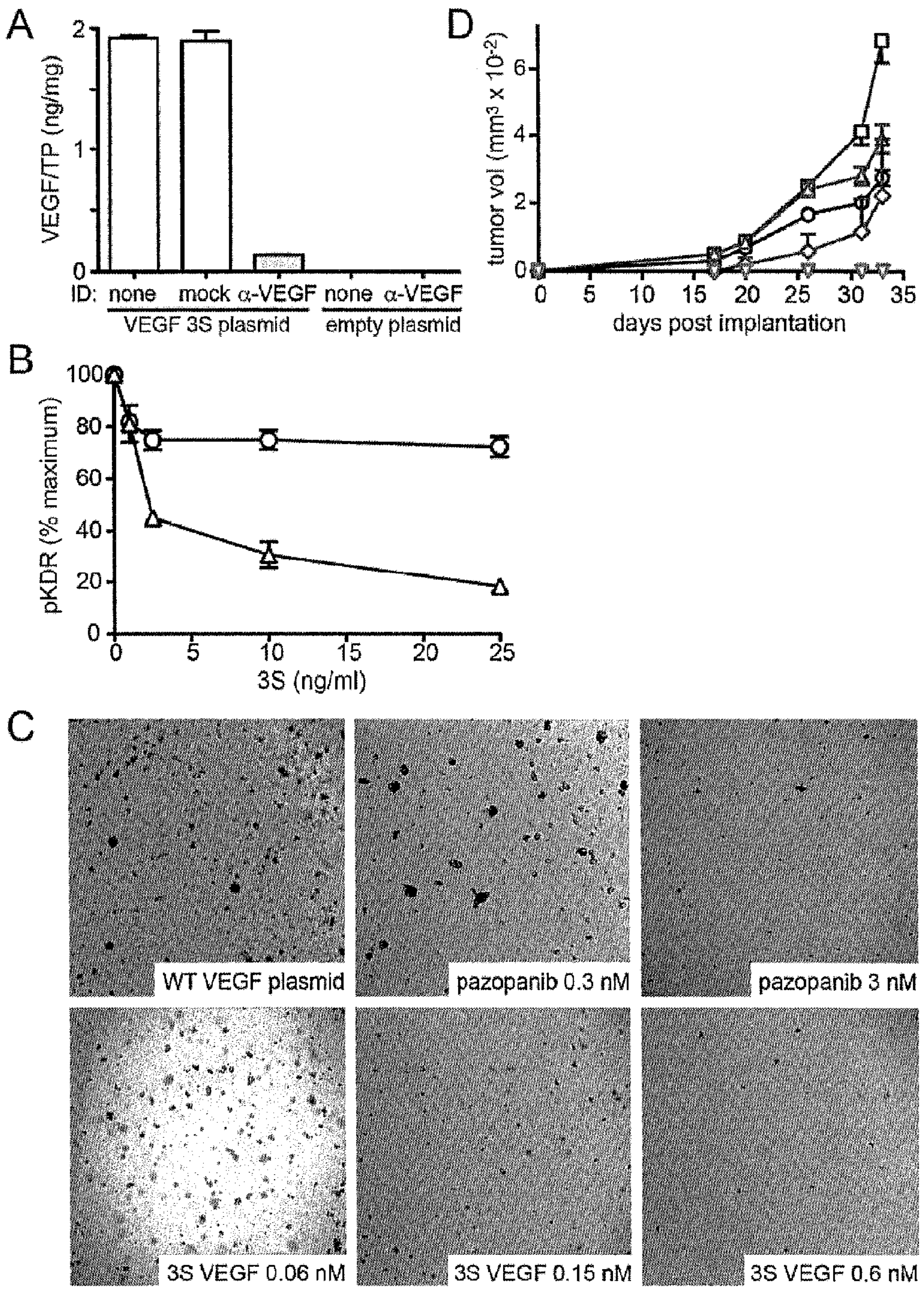

FIG. 5. Competitive antagonism of VEGFR activation and VEGFR-driven anchorage independent cell growth and tumorigenesis by VEGF165 3S protein.

A. VEGF protein content in media conditioned by 293/KDR cells transfected with VEGF165 3S plasmid (left) or empty plasmid (right), before ("none") or after immunodepletion (ID) using anti-VEGF-A ("−VEGF") or an unrelated control antibody ("mock"), expressed as mean ng/mg total protein+/−SD (n=3).

B. Phospho-KDR levels (% maximum, +/−SD, n=3) in serum-deprived 293/KDR cells treated with VEGF165 WT protein (10 ng/ml) in the presence of concentrated conditioned media from 293/KDR VEGF 3S transfectants that had been immunodepleted using a non-specific control antibody (triangles) or anti-VEGF (circles). The x-axis indicates the concentration of VEGF165 3S protein (ng/ml) in the conditioned media prior to immunodepletion.

C. Soft agar colony formation by untreated 239/KDR cells stably transfected with an expression plasmid for VEGF165 WT (upper left panel), cells treated with the indicated concentrations of the VEGR inhibitor pazopanib (upper middle and right panels), or cells treated with conditioned medium containing the indicated concentrations of VEGF165 3S protein (lower panels).

D. Mean tumor volume (mm3+/−SD) in mice (n=5/group) implanted with 293/KDR cells ($3\times10^6$ cells per animal) stably expressing VEGF165 3S (inverted triangles), VEGF165 WT (squares), or empty vector (circles), measured at the indicated times post-implantation. Other groups were implanted with a mixture of empty vector cells and VEGF165 WT transfectants at $1.5\times10^6$ cells each (triangles), or a mixture of VEGF165 WT and VEGF165 3S transfectants at $1.5\times10^6$ cells each (diamonds).

FIG. 6. Nucleotide alignments of thirteen human VEGF alpha sequences' HBD. The 6 most abundant in nature are Group 1. 7 rarer transcripts contain HBDs with insertions, and are called Group 2.

Figure 7:
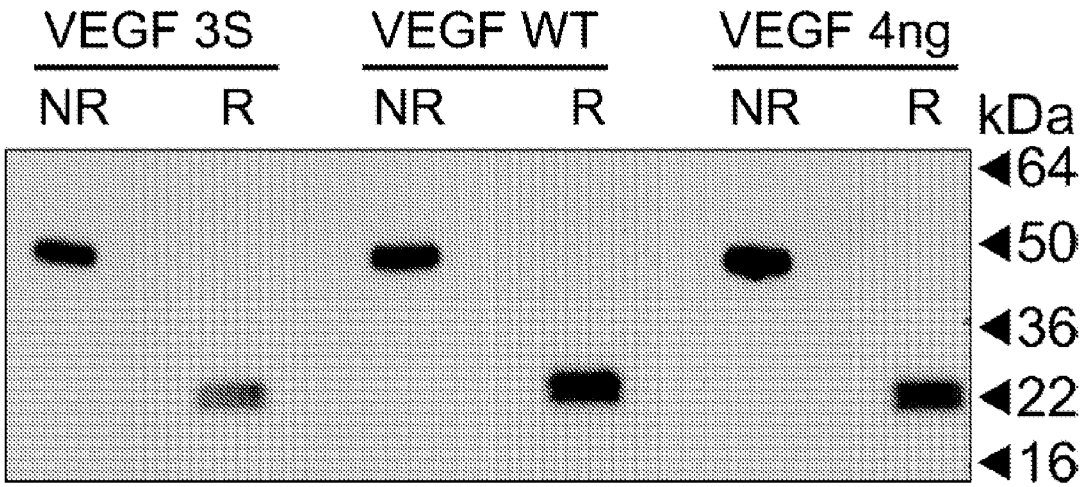

FIG. 7. VEGF165 3S and WT both form disulfide-linked protein dimers of the anticipated molecular mass.

Figure 8:
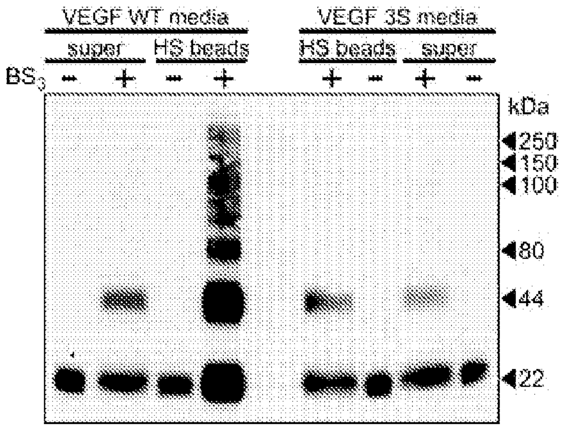

FIG. 8. VEGF165 3S is not oligomerized by heparin sulfate.

Figure 9:
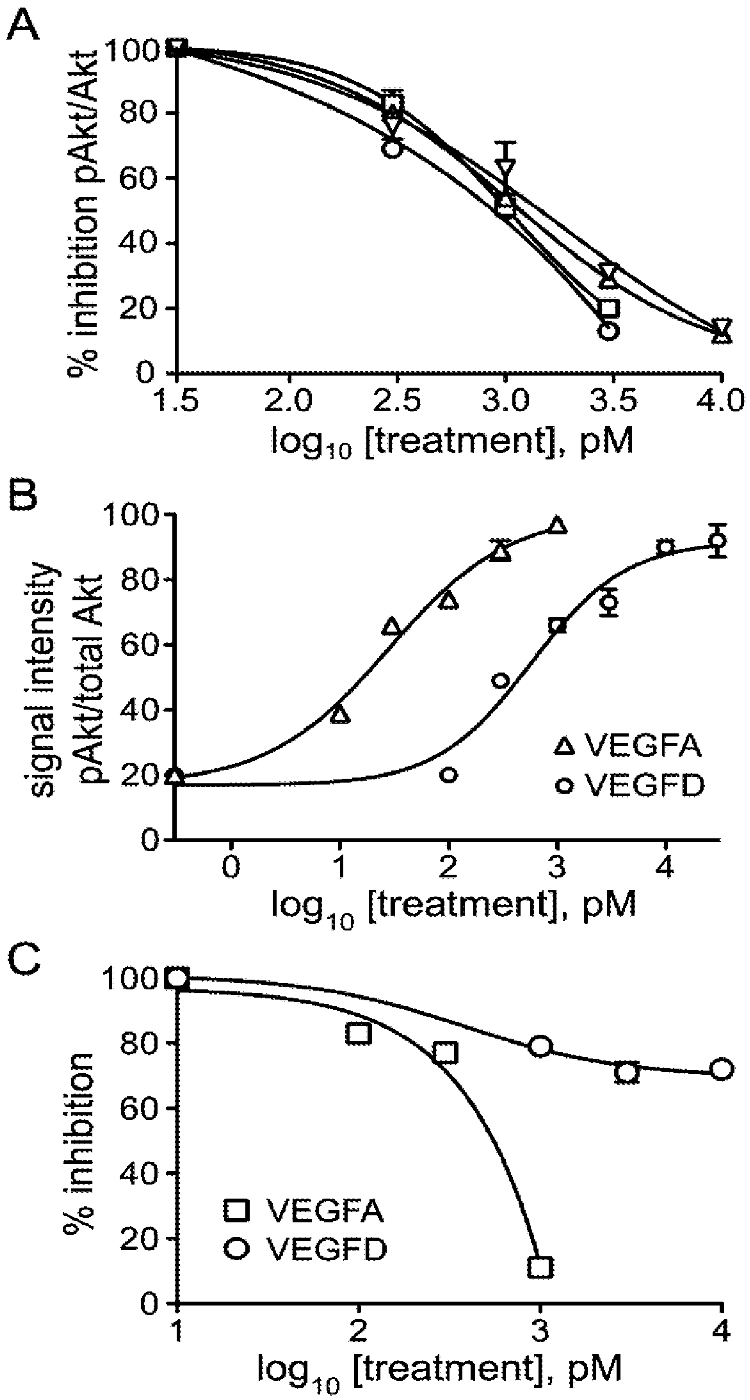

FIG. 9A-C. VEGF165 3S antagonism follows the pattern of VEGFA/VEGFR binding interaction.

Figure 10A:
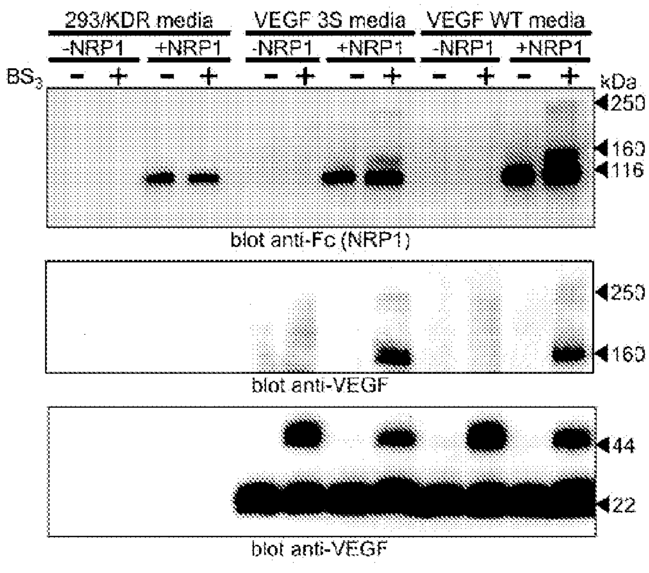
Figure 10B:
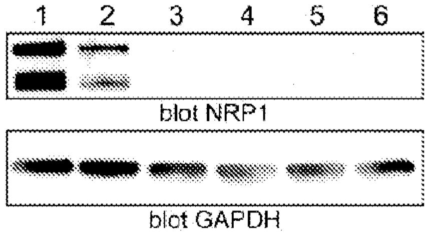

FIG. 10A-B. VEGF165 3S antagonism is independent of NRP1 interaction.

DETAILED DESCRIPTION

In the present invention, the inventors found that when HSP binding to residues R123, R124, and R159 of VEGF 165 was disrupted using combined opposite charge substitutions, unexpectedly and surprisingly the resultant polypeptide was a competitive antagonist of VEGF signaling and angiogenesis. The inventors' results suggest that receptor occupancy combined with charge-based repulsion of HSP from the ligand/receptor complex constitutes an effective general strategy for antagonizing VEGF signaling.

Figure 1B:
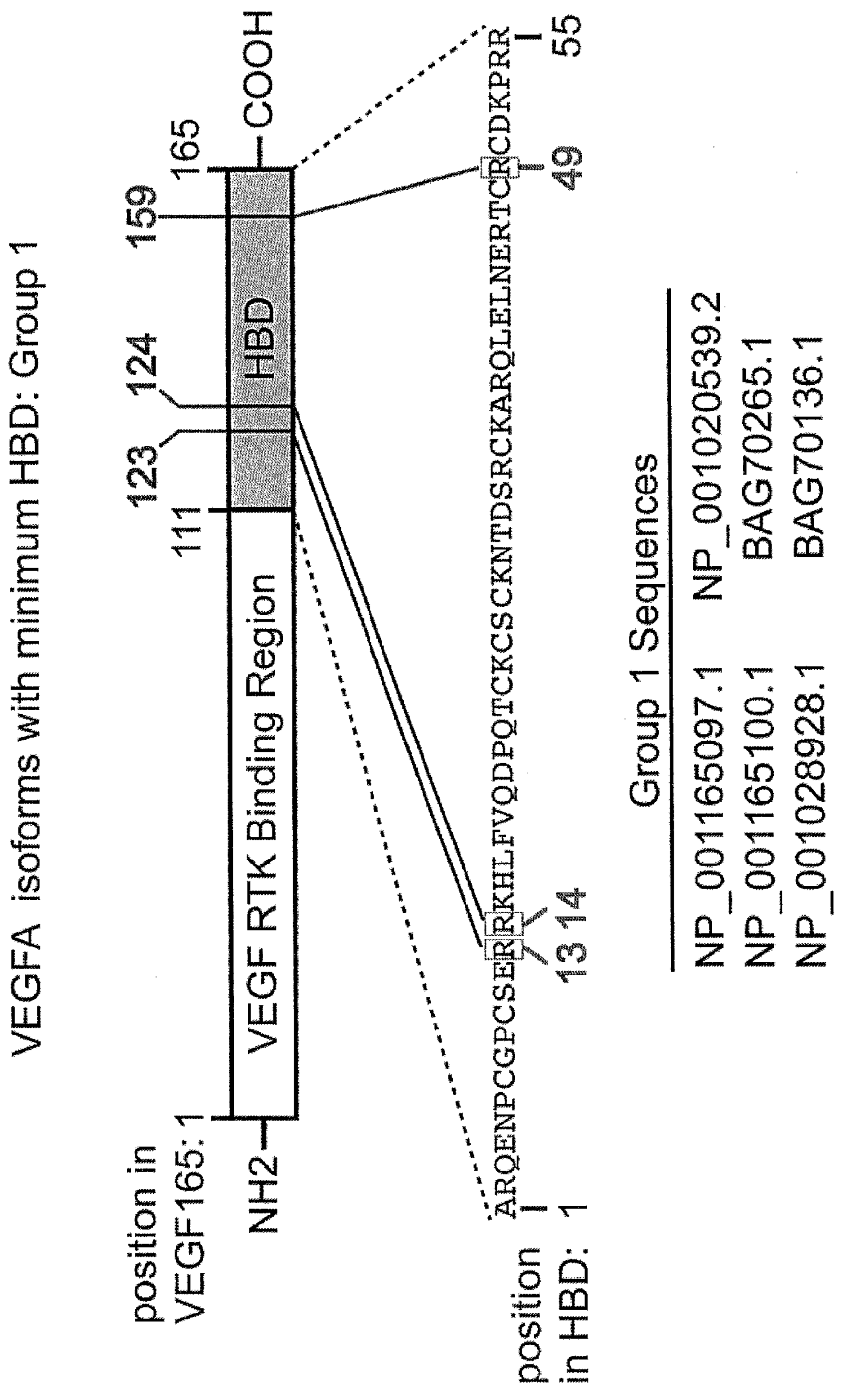
Figure 1C:
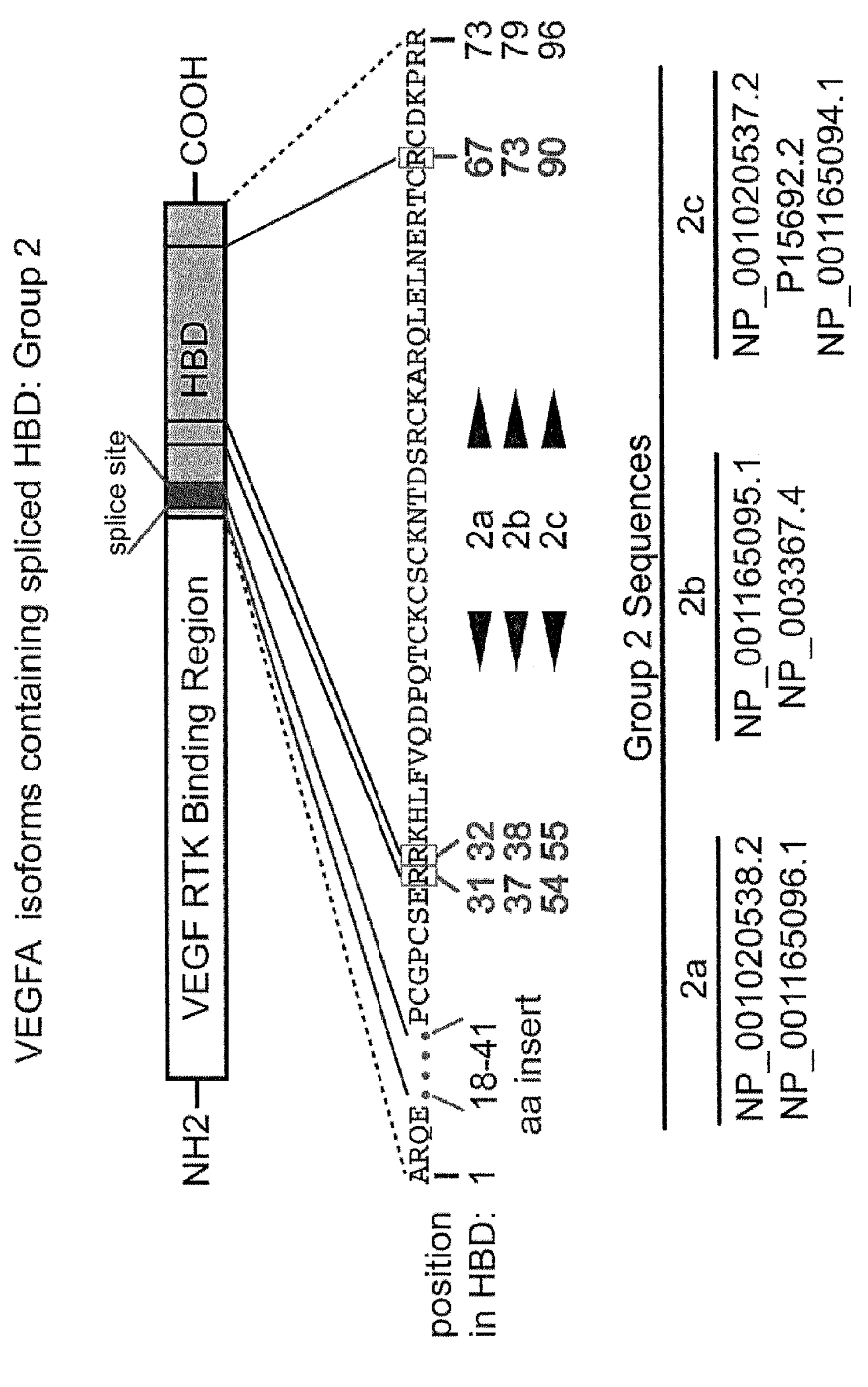
Figure 2:
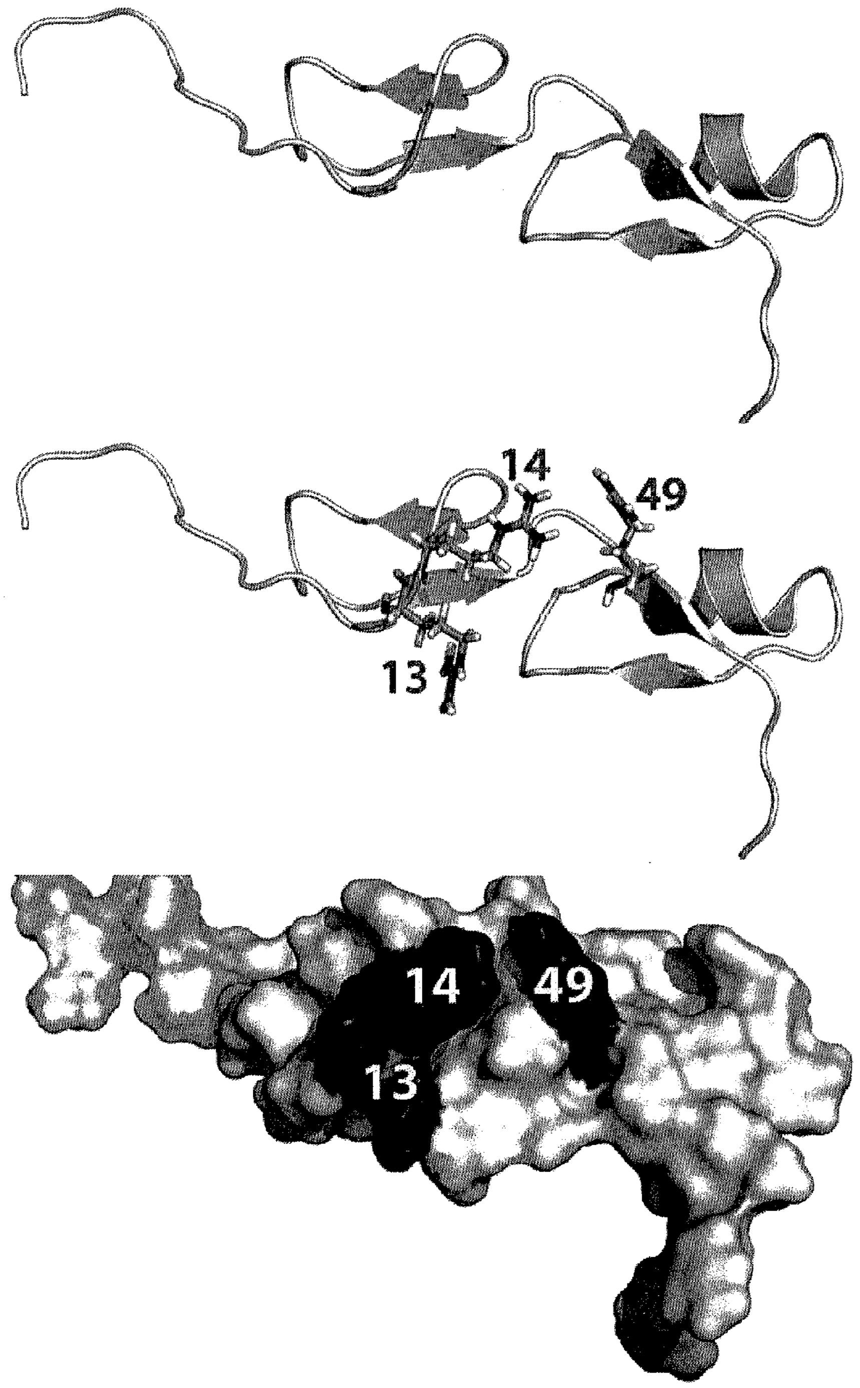
Figure 3:
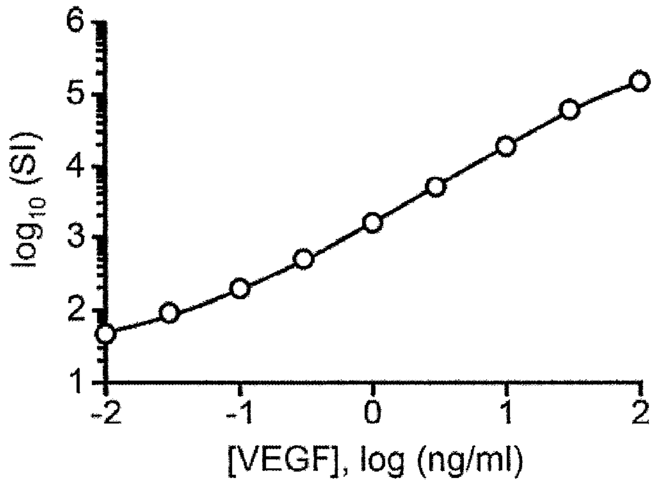
FIG. 3. Human VEGF-A protein assay. Standard curve for the electrochemiluminescent two-site immunoassay for VEGF-A: signal intensity (SI) vs. VEGF protein concentration.
Figure 4:
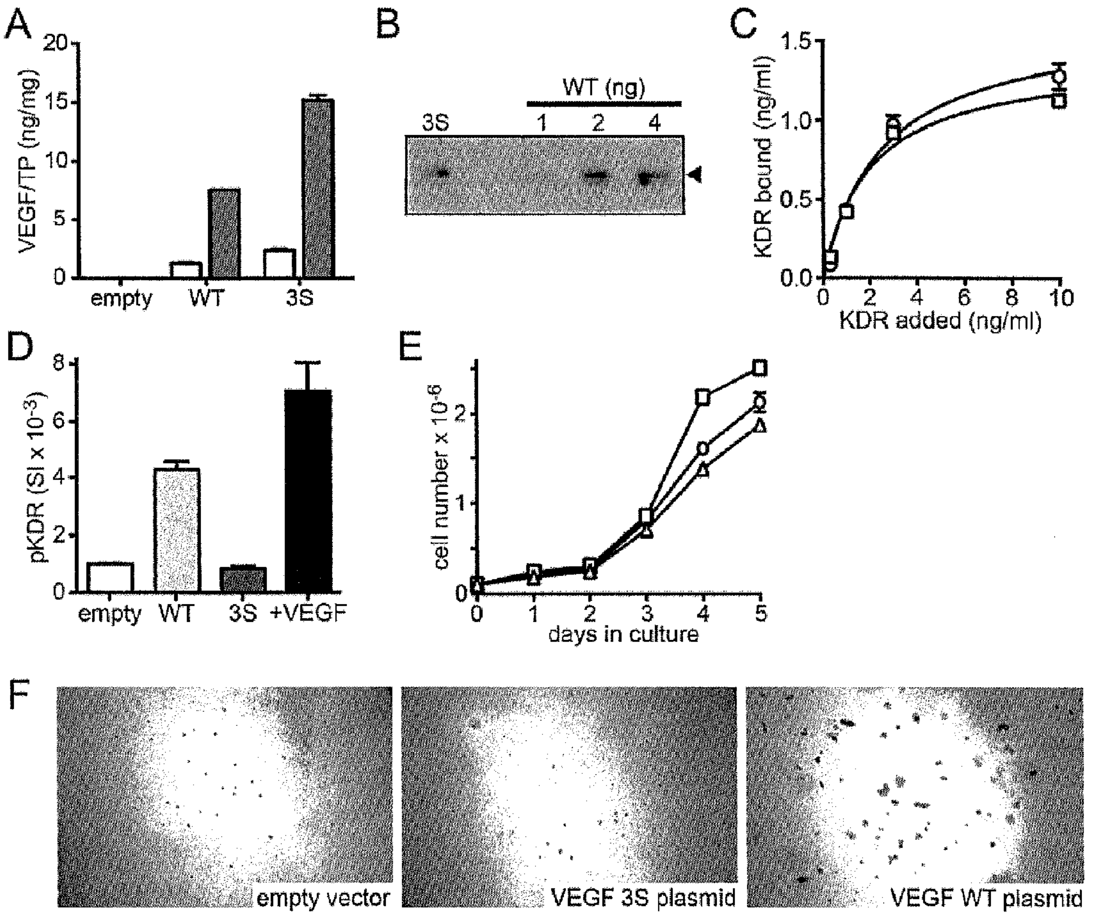
FIG. 4. VEGF165 3S protein retains normal mass, immunoreactivity and KDR binding but not signaling activity.

The inventors generated a cDNA to encode opposite charge substitutions at three critical HS binding residues in human VEGF165, positions R123E/R124E/R159E in the mature VEGF165 protein, numbered from the site of signal peptide cleavage (designated VEGF165 3S; FIGS. 1A and B). For convenience in identifying these residues in the context of other VEGF-A isoforms that also contain the heparin binding domain (HBD; the HBD sequence is identical in for some VEGF-A isoforms, but the HBD for other isoforms have insertions/deletions; see the list of VEGF-A isoform sequences discussed elsewhere in the Specification, shown at FIG. 1B, 1C, and FIG. 6). In the group of HBD referred to as Group 1, the positions of these residues relative to the heparin binding domain alone may be referred to as R13E, R14E and R49E, as depicted in FIG. 1B. These are depicted in the three dimensional NMR structure of the VEGF165 heparin binding domain in FIG. 2. FIG. 1C shows that there are also HBDs that have insertions/deletions in the HBD that change the relative numbering of the positions of these residues in the HBD domain, as depicted in the figure and in FIG. 6. Expression plasmids encoding vector alone, VEGF165 WT, or VEGF165 3S were stably transfected into HEK293 cells that had been engineered previously to express $2.5\times10^6$ VEGFR2 per cell (293/KDR; Backer et al., 2005). The inventors had anticipated that VEGF165 WT expression in these cells would result in autocrine KDR activation and cell transformation. The inventors had expected VEGF165 3S to lack KDR activating ability and thus to have no effect on phenotype. Ectopic VEGF protein production by transfectants was measured using a two-site immunoassay with a detection limit of 37.5 attomoles/25 ul (1.5 pM) VEGF (FIG. 3). Among marker selected mass cultures, WT transfectants produced ~1.0 ng/ml/24 h VEGF165 protein in conditioned media, 3S transfectants produced ~2.5 ng/ml/24 h, and VEGF protein was undetectable in the empty vector control media (FIG. 4A, white bars). The VEGF content in low volume detergent extracts from the same cells was proportionally higher, as expected (FIG. 4A, gray bars). Molecular mass and antibody recognition of VEGF165 3S protein in conditioned media were indistinguishable from WT (FIG. 4B). Saturation binding of VEGF165 3S to KDR in vitro (FIG. 4C, squares; KD ~19 pM) was also equivalent to VEGF165 WT binding (FIG. 4C, circles; KD ~23 pM) and consistent with published steady-state binding affinity values (Ferrara, 2004).

Thus, the inventors found that while VEGF165 3S binds KDR like VEGF165 WT protein, the mutant failed to induce KDR kinase activity and antagonized VEGF165 WT binding and signaling in vitro and in vivo. These results show a critical role for HS in receptor activation and show that targeted disruption of critical HS binding sites is a feasible antagonist development strategy for VEGF. This work shows that that charge based repulsion of HSP from the ligand/receptor complex is an effective general strategy for antagonizing signaling by VEGF.

These results are surprising in view of previous work where these residues on VEGF165, mutated from arginine to alanine, resulted in a mutant that retained full activity as an agonist in stimulating angiogenesis.

Without being bound by theory, the inventors' understanding of KDR activation by VEGF165 and HS suggests a mechanistic basis for signaling antagonism by the targeted disruption of HS-ligand binding. The VEGF binding site in KDR encompasses IgG-like domains (D) 1-3: D2 contains primary contacts and D1 and D3 contribute to overall binding affinity and specificity. HS was found to be required for high affinity binding of VEGF165 to KDR ectopically expressed in HS-negative CHO pgsA 745 cells. Similar to Met and fibroblast growth factor receptors, KDR also interacts directly with HS, through at least one site located between D6 and D7. Recent structural studies of the KIT, PDGF and VEGF receptor families highlight the importance of homotypic receptor-receptor interaction domains in stabilizing receptor dimerization and kinase transactivation: direct contacts between D4 domains for KIT and D7 domains for KDR are enabled by ligand-induced conformational changes in the receptor ectodomain. In these models, sequential binding events promote and incrementally stabilize HS-ligand-receptor aggregates capable of signaling. Without being bound by theory, the inventors hypothesize that VEGF165 first binds KDR D2; the weaker VEGF165-D1 and -D3 interactions may be stabilized by HS-VEGF interaction and by HS-VEGF-KDR bridging at D6/D7. VEGF-HS also may also induce conformational changes that enable the apposition of KDR D7 domains and in turn, homotypic interaction and kinase transactivation. Our observations underscore the importance of specific HS interactions in facilitating events after ligand binding that are required for KDR activation, and expose their susceptibility to targeted disruption.

HS binding growth factors promote tumor growth, angiogenesis and metastasis in a variety of human cancers. In addition to the strategy described here, oligosaccharide HS mimetics and modified heparin fragments can act as HS binding antagonists. However, the complexity of HS glycosaminoglycans (GAGs) challenges the development of potent and selective agents, and frequent alterations in HS GAG composition in tumors may render such agents less competitive for ligand binding. In contrast, opposite substitutions to critical HS binding residues in an otherwise wild type protein ligand are simple to introduce, unaffected by tumor HS GAG composition, and inherently pathway selective. These features suggest that the inventors' approach is an expedient and practical route for the development of antagonists of HS binding growth factors, in particular, VEGF165.

In one aspect, the present invention provides novel VEGF variants. In particular, the invention relates to variants of vascular endothelial growth factor-A (VEGF-A). VEGF-A is an essential regulator of normal angiogenesis during embryogenesis and adulthood, and participates in pathological angiogenesis in many diseases, including many prevalent forms of cancer. As is known in the art, VEGF-A signaling is mediated through the cell surface receptor tyrosine kinases VEGFR1 (Flt-1) and VEGFR2 (Flk-1, KDR). Differential splicing of VEGF-A pre-mRNA results in the expression of multiple VEGF-A isoforms, the most abundant of which in humans are VEGF121, VEGF 165 and VEGF 189. All isoforms contain the same binding sites for VEGFR1 and VEGFR2, but differ in their capacity to bind to heparan sulfate proteoglycans (HSPs) ubiquitously present in the extracellular matrix and on target cell surfaces, due to the presence or absence of two basic heparin-binding domains (HBDs) encoded by exons 6 and 7. VEGF 121 lacks a HBD and is freely diffusible in the extracellular space, whereas VEGF 165 (SEQ ID NO:3) and VEGF 189 display moderate and high affinity HSP binding, respectively, limiting the mobility of these isoforms in HSP-rich compartments. The exon 7-encoded peptide also contains residues that enable VEGF 165 to bind to the VEGF co-receptor NRP1.

In one embodiment, the present invention relates to variants of VEGF 165. SEQ ID NO:2 shows vascular endothelial growth factor A isoform 1 precursor from *Homo sapiens*. This form is 191 amino acids in length. A signal sequence is cleaved off to form the mature vascular endothelial growth factor A isoform 1 *Homo sapiens* SEQ ID NO:3. SEQ ID NO:3 may be referred to as "VEGF 165" and is 165 amino acids in length. VEGF 165 is also referred to herein and elsewhere as native VEGF 165, mature VEGF 165, and the like. SEQ ID NO:4 is the carboxyl terminal region of SEQ ID NO:2 and SEQ ID NO:3, and corresponds to residues 111-165 of SEQ ID NO:3 and is defined by a plasmin cleavage site. Together, SEQ ID NO:2-4 can be referred to herein as VEGF 165 sequences; they may also be referred to as "native VEGF amino acid sequences" or "native VEGF" or "native VEGF polypeptides". They may also be referred to as "native VEGF 165 amino acid sequences" or "native VEGF 165" or "native VEGF 165 polypeptides".

The VEGF variants described herein represent VEGF 165 sequences that have been modified in accordance with the invention. These variants comprise at least one polypeptide having a modified heparin binding domain. These polypeptides may be referred to as VEGF variant polypeptides, a VEGF variant amino acid sequence, VEGF 165 variants, VEGF 165 variant amino acid sequences, VEGF 165 variant polypeptides, and the like. The VEGF variants described herein may also be referred to as "polypeptides of the present invention" or "VEGF variants of the present invention," "VEGF sequences of the present invention," and the like.

A "native sequence" protein comprises the amino acid sequence of a protein as found in nature, e.g. in a human. The native sequence protein can be made by recombinant or other synthetic means, or may be isolated from a native source.

The terms "amino acid" and "amino acids" refer to all naturally occurring L-α-amino acids. This definition is meant to include norleucine, ornithine, and homocysteine. The amino acids are identified by either the single-letter or three-letter designations, as follows: Asp (D) aspartic acid Thr (T) threonine Ser (S) serine Glu (E) glutamic acid Pro (P) proline Gly (G) glycine Ala (A) alanine Cys (C) cysteine Val (V) valine Met (M) methionine Ile (I) isoleucine Leu (L) leucine Tyr (Y) tyrosine Phe (F) phenylalanine His (H) histidine Lys (K) lysine Arg (R) arginine Trp (W) tryptophan Gln (Q) glutamine Asn (N) asparagine.

The present invention, in part, relates to VEGF variants having one or more substitutions on the heparin binding domain of negatively charged (e.g., acidic) amino acid residues for amino acid residue arginine at certain specified positions on a VEGF polypeptide, as disclosed herein. Appropriate VEGF polypeptides with which to create variants are discussed herein and including human alternately spliced VEGF isoforms of 121, 145, 165, 183, 189, and 206 amino acids in length, and species orthologs of VEGF. Specific arginine residues to substitute with an acidic amino acid, for a specific VEGF polypeptide, are disclosed herein. An acidic amino acid is defined herein as an amino acid residue having a negative charge at physiological pH. In one embodiment, an acidic amino acid is aspartic acid (Asp, D) or glutamic acid (Glu, E). In one embodiment, an acidic amino acid is glutamic acid. Heparin sulfate (HS) binding is a charge-based interaction wherein sulfate moieties in HS bind to basic residues (R or K) in the VEGF HS binding domain. Changing the basic R residues or K residues to either D residues or E residues has the same impact-repulsion of the HS sulfate moieties from the VEGF-VEGFR complex, and signaling antagonism.

In one embodiment, the heparin binding domain of a native VEGF 165 sequence of the present invention is modified by substituting negatively charged (e.g., acidic) amino acid residues for amino acid residue arginine at certain specified positions on a VEGF polypeptide. VEGF variant polypeptides of the invention include SEQ ID NO:25, SEQ ID NO:26, or SEQ ID NO:27. SEQ ID NO:25 is the same as SEQ ID NO:2, except that one or more of positions 149, 150, and 185 of SEQ ID NO:25 can contain an acidic amino acid residue in place of the arginine at corresponding positions of SEQ ID NO:2. SEQ ID NO:26 is the same as SEQ ID NO:3, except that one or more of positions 123, 124, and 159 of SEQ ID NO:26 can contain an acidic amino acid in place of the arginine at corresponding positions of SEQ ID NO:3. SEQ ID NO:27 is the same as SEQ ID NO:4, except that one or more of positions 13, 14, and 49 of SEQ ID NO:27 can contain an acidic amino acid in place of arginine at corresponding positions of SEQ ID NO:4.

In another embodiment, the heparin binding domain is modified by substituting negatively charged (e.g., acidic) amino acid residues for amino acid residue arginine at certain specified positions on a VEGF polypeptide. VEGF variant polypeptides of the invention include SEQ ID NO:6, SEQ ID NO:7, or SEQ ID NO:8. SEQ ID NO:6 is the same as SEQ ID NO:2, except that positions 149, 150, and 185 of SEQ ID NO:6 contain a glutamic acid in place of the arginine at corresponding positions of SEQ ID NO:2. SEQ ID NO:7 is the same as SEQ ID NO:3, except that at positions 123, 124, and 159 of SEQ ID NO:7 contain a glutamic acid in place of the arginine at corresponding positions of SEQ ID NO:3. SEQ ID NO:7 is also referred to herein as "3S VEGF 165." SEQ ID NO:8 is the same as SEQ ID NO:4, except that at positions 13, 14, and 49 of SEQ ID NO:8 contain a glutamic acid in place of arginine at corresponding positions of SEQ ID NO:4.

Other VEGF variant polypeptides of the invention include SEQ ID NO:10, SEQ ID NO:11, or SEQ ID NO:12. SEQ ID NO: 10 is the same as SEQ ID NO:2, except that positions 149 and 150 of SEQ ID NO:10 contain a glutamic acid in place of the arginine at corresponding positions of SEQ ID NO:2. SEQ ID NO:11 is the same as SEQ ID NO:3 except that positions 123 and 124 of SEQ ID NO:11 contain a glutamic acid in place of the arginine at corresponding positions of SEQ ID NO:3. SEQ ID NO:12 is the same as SEQ ID NO:4, except that positions 13 and 14 of SEQ ID NO:12 contain a glutamic acid in place of arginine at corresponding positions of SEQ ID NO:4.

Other VEGF variant polypeptides of the invention include SEQ ID NO:14, SEQ ID NO:15, or SEQ ID NO:16. SEQ ID NO: 14 is the same as SEQ ID NO:2, except that position 185 of SEQ ID NO:14 contains a glutamic acid in place of the arginine at the corresponding position of SEQ ID NO:2. SEQ ID NO:15 is the same as SEQ ID NO:3 except that position 159 of SEQ ID NO:15 contains a glutamic acid in place of the arginine at the corresponding position of SEQ ID NO:3. SEQ ID NO:16 is the same as SEQ ID NO:4, except that position 49 of SEQ ID NO:16 contains a glutamic acid in place of arginine at the corresponding position of SEQ ID NO:4.

Other VEGF variant polypeptides of the invention include SEQ ID NO:18, SEQ ID NO:19, or SEQ ID NO:20. SEQ ID NO: 18 is the same as SEQ ID NO:2, except that position 150 of SEQ ID NO:14 contains a glutamic acid in place of the arginine at the corresponding position of SEQ ID NO:2.

SEQ ID NO:19 is the same as SEQ ID NO:3 except that position 124 of SEQ ID NO:19 contains a glutamic acid in place of the arginine at the corresponding position of SEQ ID NO:3. SEQ ID NO:20 is the same as SEQ ID NO:4, except that at position 14 of SEQ ID NO:20 contains a glutamic acid in place of arginine at the corresponding position of SEQ ID NO:4.

Other VEGF variant polypeptides of the invention include SEQ ID NO:22, SEQ ID NO:23, or SEQ ID NO:24. SEQ ID NO: 22 is the same as SEQ ID NO:2, except that position 149 of SEQ ID NO:22 contains a glutamic acid in place of the arginine at the corresponding position of SEQ ID NO:2. SEQ ID NO:23 is the same as SEQ ID NO:3 except that position 123 of SEQ ID NO:23 contains a glutamic acid in place of the arginine at the corresponding position of SEQ ID NO:3. SEQ ID NO:24 is the same as SEQ ID NO:4, except that at position 13 of SEQ ID NO:24 contains a glutamic acid in place of arginine at the corresponding position of SEQ ID NO:4.

In one embodiment, the variant vascular endothelial cell growth factor (VEGF) variant polypeptide comprises a variant C-terminal heparin binding domain and a native receptor tyrosine kinase binding domain, wherein said variant polypeptide has one or more amino acid alternations from a native VEGF polypeptide, wherein said variant polypeptide binds heparin at a lower affinity than and/or repels heparin as compared to said native VEGF, and wherein the affinity of the variant polypeptide for both VEGFR-1 (FLT-1) and VEGFR-2 (KDR/FLK-1) is substantially maintained in comparison to said native VEGF amino acid sequence, and wherein said variant polypeptide antagonizes KDR signal activation. In one embodiment the polypeptide comprises a variant C-terminal heparin domain.

In one embodiment, a native VEGF polypeptide refers to one or more of the polypeptides comprising SEQ ID NO:2, SEQ ID NO:3, or SEQ ID NO:4.

In one embodiment, a variant VEGF polypeptide comprises a polypeptide which comprises SEQ ID NO:25 wherein the amino acid of at least one of positions 149, 150, and 185 of SEQ ID NO:25 is an acidic amino acid. An acidic amino acid is defined herein as an amino acid residue having a negative charge at physiological pH. In one embodiment, an acidic amino acid is aspartic acid (Asp, D) or glutamic acid (Glu, E). In another embodiment, a variant VEGF polypeptide comprises a polypeptide which comprises SEQ ID NO:26 wherein the amino acid of at least one of positions 123, 124, and 159 of SEQ ID NO:26 is an acidic amino acid. In another embodiment, a variant VEGF polypeptide comprises a polypeptide which comprises SEQ ID NO:27 wherein the amino acid of at least one of positions 13, 14, and 49 of SEQ ID NO:27 is an acidic amino acid.

In another embodiment, the present invention includes VEGF189 variant polypeptides and polynucleotides. VEGF189 variant polypeptides and polynucleotides are differential splicing isoforms from VEGF165. VEGF189 variant polypeptides of the invention include VEGF189 which have acidic amino acid changes at one or more of the equivalent (conserved) sites as the ones described for VEGF165. On the mature form of VEGF189, these are R147, 148, and 183. VEGF 189 display moderate and high affinity HSP binding, respectively, limiting the mobility of these isoforms in HSP-rich compartments. VEGF189 variant polypeptides of the invention include the following polypeptides: VEGF 189 precursor of 215 amino acids having E at positions 173, 174, and 209 (SEQ ID NO:34), VEGF 189 precursor of 215 amino acids having E at positions 173, 174 (SEQ ID NO:35), VEGF 189 precursor of 215 amino acids having E at position 209 (SEQ ID NO:36), VEGF 189 precursor of 215 amino acids having E at position 174 (SEQ ID NO:37), and VEGF 189 precursor of 215 amino acids having E at position 173 (SEQ ID NO:38). In SEQ ID NOs: 34 through 38 the alternations to obtain the variant VEGF189 are found at one or more of AA 173, 174 and 209. The invention includes the mature forms of the foregoing amino acids of SEQ ID NO:34, 35, 36, 37, and 38. The invention also includes polynucleotides that include polynucleotides that encode any of the VEGF189 variant polypeptides of the invention.

Thus, the present invention includes polypeptides wherein the variant polypeptide includes the following: a polypeptide comprising the mature form of a polypeptide which include the following: SEQ ID NO:34, SEQ ID NO:35, SEQ ID NO:36, SEQ ID NO:37, and SEQ ID NO:38; and a polypeptide having at least 95% identity to a polypeptide described above, and having the ability to antagonize KDR signal activation.

Other variant VEGF polypeptides of the present invention include other VEGF-A isoforms comprising a C-terminal domain containing a heparin binding domain comprising the amino acid substitutions of the present invention. Such GenBank Files containing VEGF-A isoforms that contain the heparin binding domain which can be modified in accordance with the present invention. e.g., having a C terminal domain containing a heparin binding domain comprising the amino acid substitutions described herein. These include vascular endothelial growth factor A isoform o precursor (*Homo sapiens*) which have modifications at equivalent positions on the amino acid sequence as the other variant sequences claimed herein. As discussed herein at FIG. 1B, Group 1 sequences for the isoforms disclosed in FIG. 1B have modifications in the HBD of 13, 14, and 49 positions to an acidic amino acid, wherein in one embodiment, the acidic amino acid is E. Group 1 sequences include NP_001165097.1; NP_001165100.1; NP_0010289928.1, NP_001020539, BAG70265.1, BAG70136.1. NP_001165100.1 GI:284172471; vascular endothelial growth factor A isoform 1 precursor (*Homo sapiens*) is represented herein as SEQ ID NO:47, with a C terminal domain (HBD) of SEQ ID NO:68. NP_001165097.1, GI:284172465; is SEQ ID NO:48, with a C terminal domain (HBD) of SEQ ID NO:4. Vascular endothelial growth factor A isoform k precursor (*Homo sapiens*), a 209 aa protein, NP_001165096.1, GI:284172463; is represented herein as represented herein as SEQ ID NO:49, with a C terminal domain (HBD) of SEQ ID NO:64. Vascular endothelial growth factor A isoform j precursor (*Homo sapiens*), a 215 aa protein, NP_001165095.1, GI:284172461 is represented herein as SEQ ID NO:50, with a C terminal domain (HBD) of SEQ ID NO:65. Vascular endothelial growth factor A isoform i precursor (*Homo sapiens*), a 232 aa protein, NP_001165094.1GI:284172459 is represented herein as SEQ ID NO:51,with a C terminal domain (HBD) of SEQ ID NO:67. Vascular endothelial growth factor A isoform g (*Homo sapiens*), a 371 aa protein, NP_001028928.1GI: 76781487 is represented herein as SEQ ID NO:52, with a C terminal domain (HBD) of SEQ ID NO:68. Vascular endothelial growth factor A isoform d (*Homo sapiens*), a 371 aa protein, NP_001020539.2, GI:76781483; is represented herein as SEQ ID NO:53, with a C terminal domain (HBD) of SEQ ID NO:4. Vascular endothelial growth factor A isoform c (*Homo sapiens*) a 389 aa protein, NP_001020538.2, GI:76781482, is represented herein as SEQ ID NO:54, with a C terminal domain (HBD) of SEQ ID NO:64. Vascular endothelial growth factor A isoform b (*Homo sapiens*) a 395 aa protein, NP_003367.4, GI:76781481 is represented herein as SEQ ID NO:55, with a C terminal domain (HBD) of SEQ ID NO:65. Vascular endothelial growth factor A isoform a (*Homo sapiens*), a 412 aa protein, NP_001020537.2, GI:76781480, is represented herein as SEQ ID NO:56, with a C terminal domain (HBD) of SEQ ID NO:67. Vascular endothelial growth factor isoform VEGF165 (*Homo sapiens*), a 191 aa protein, BAG70265.1, GI:197692603, is represented herein as SEQ ID NO:57, with a C terminal domain (HBD) of SEQ ID NO:4. Vascular endothelial growth factor isoform VEGF165 (*Homo sapiens*), a 191 aa protein, BAG70136.1GI: 197692345 , is represented herein as SEQ ID NO:58, with a C terminal domain (HBD) of SEQ ID NO:4. Vascular permeability factor, a 232 aa protein P15692.2, GI:17380528, is represented herein as SEQ ID NO:59, with a C terminal domain (HBD) of SEQ ID NO:67. See FIG. 6, showing an alignment of thirteen human VEGF alpha sequences (isoforms) heparin binding domains. The six most abundant isoforms in nature are grouped as Group 1 (see FIG. 1B). FIG. 1C shows an alignment between heparin binding domains of a second group, Group 2, which contains heparin binding domains with insertions. As can be seen from both the alignment and the schematics, the HBD insertions in Group 2 change the numbering of the critical HS binding residues (13,14,49 in Group 1) to 31,32,67 in Group 2a; 37,38,73 in Group 2b; and 54,55,90 in Group 2c.

Thus, variant polypeptides of the invention include polypeptides comprising a polypeptide which include the following: SEQ ID NO:4, wherein the amino acid of at least one of positions 13, 14, and 49 of the sequence of SEQ ID NO:4 is an acidic amino acid; SEQ ID NO:64, wherein the amino acid of at least one of positions 31, 32, and 67 of the sequence of SEQ ID NO:64 is an acidic amino acid; SEQ ID NO:65, wherein the amino acid of at least one of positions 37, 38, and 73 of the sequence of SEQ ID NO:65 is an acidic amino acid, SEQ ID NO:67, wherein the amino acid of at least one of positions 54, 55, and 90 of the sequence of SEQ ID NO:67 is an acidic amino acid, and SEQ ID NO:68, wherein the amino acid of at least one of positions 13, 14, and 49 of the sequence of SEQ ID NO:68 is an acidic amino acid; as well as polypeptides having at least 95% identity to a polypeptide described above, and having the ability to antagonize KDR signal activation.

Variant polypeptides of the invention also include a polypeptide comprising a polypeptide which include the following: SEQ ID NO:47, wherein the amino acid of at least one of positions 149, 150 and 185 of SEQ ID NO:47 is an acidic amino acid, SEQ ID NO:48, wherein the amino acid of at least one of positions 149, 150, and 185 of SEQ ID NO:48 is an acidic amino acid, SEQ ID NO:49, wherein the amino acid of at least one of positions 167, 168 and 203 of SEQ ID NO:49 is an acidic amino acid, SEQ ID NO:50, wherein the amino acid of at least one of positions 173, 174, and 209 of SEQ ID NO:50 is an acidic amino acid, SEQ ID NO:51, wherein the amino acid of at least one of positions 190, 191, and 226 of SEQ ID NO:51 is an acidic amino acid, SEQ ID NO:52, wherein the amino acid of at least one of positions 329, 330, and 365 of SEQ ID NO:52 is an acidic amino acid, SEQ ID NO:53, wherein the amino acid of at least one of positions 329, 330, and 365 of SEQ ID NO:53 is an acidic amino acid, SEQ ID NO:54, wherein the amino acid of at least one of positions 347, 348, and 383 of SEQ ID NO:54 is an acidic amino acid, SEQ ID NO:55, wherein the amino acid of at least one of positions 353, 354, and 389 of SEQ ID NO:55 is an acidic amino acid, SEQ ID NO:56, wherein the amino acid of at least one of positions 370, 371 and 406 of SEQ ID NO:56 is an acidic amino acid, SEQ ID NO:57, wherein the amino acid of at least one of positions 149, 150 and 185 of SEQ ID NO:57 is an acidic amino acid, SEQ ID NO:58, wherein the amino acid of at least one of positions 149, 150 and 185 of SEQ ID NO:58 is an acidic amino acid, and SEQ ID NO:59, wherein the amino acid of at least one of positions 190, 191, and 226 of SEQ ID NO:59 is an acidic amino acid; as well as polypeptides having at least 95% identity to a polypeptide described above, and having the ability to antagonize KDR signal activation.

The present invention, then, also includes a vascular endothelial cell growth factor (VEGF) variant polypeptide comprising a C-terminal heparin binding domain, wherein said variant polypeptide has one or more amino acid alternations from a native VEGF polypeptide, where the variant includes a heparin sulfate binding domain (HBD) wherein HBD can comprise a HBD as described in FIG. 1B or FIG. 1C or FIG. 6. For example, the HBD can contain a splice site as shown in FIG. 1C and FIG. 6 with additional sequences spliced in, thus adjusting the position of the variant residues based on a numbering position from position 1 in the HBD, as seen in FIG. 1C. For example, the HBD can comprise the sequence as shown in, SEQ ID NO:64, SEQ ID NO:65, SEQ ID NO:66, SEQ ID NO:67, and/or SEQ ID NO:68, which have an insertion between residues 4 (E) and 6 (P) of between 18-41 amino acid residues replacing residue 5(N) as shown in FIG. 6, wherein at least one of equivalent of positions 13, 14, and 49 as shown in SEQ ID NO:4 is substituted with an acidic amino acid, such as E or D. For example, for SEQ ID NO:64, the substitutions may occur at positions 31, 32, and 67. For example, for SEQ ID NO:65, the substitutions may occur at positions 37, 38 and 73. For example, for SEQ ID NO:67, the substitutions may occur at positions 54, 55, and 90. For SEQ ID NO:68, the variant positions are the same, but the C terminus has a variant ending as shown in the FIG. 6. Specifically, the inserts can include KKSVRGKGKGQKRKRKKSR (SEQ ID NO:60), see full length C terminal domain SEQ ID NO:64; KKSVRGKGKGQKRKRKKSRYKSWSV (SEQ ID NO:61), see full length C terminal domain SEQ ID NO:65, KKSVRGKGKGQKRKRKKSRYKSWSVYVGARCCLMPWSLPG (SEQ ID NO:62), see full length C terminal domain SEQ ID NO:66, and KKSVRGKGKGQKRKRKKSRYKSWSVYVGARCCLMPWSLPGPH (SEQ ID NO:63), see full length C terminal domain SEQ ID NO:67. The C terminus of the HBD may vary with a SLTRKD (SEQ ID NO:69), see full length C terminal domain SEQ ID NO:68.

For convenience these sequences may be called Group 2 sequences and the positioning of the variant residues may be at residue 31, 31 and/or 67 of the HBD for NP_001020538.2 (SEQ ID NO:64) and NP_001165096.1 (SEQ ID NO:64), at residues 37, 38 and/or 73 of the HBD for NP_001165095.1 (SEQ ID NO:65) and NP_003367.4 (SEQ ID NO:65), and at residues 54, 55 and 90 of HBD for NP_001020537.2 (SEQ ID NO:67), p15692.2(SEQ ID NO:67), and NP_001165094.1(SEQ ID NO:67). The VEGF variants of the present invention show at least about 75%, at least about 80%, at least about 85%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, amino acid sequence identity with a polypeptide of the present invention, and optionally having the ability to antagonize KDR signal activation.

Alternative embodiments within the scope of the invention include those where the vascular endothelial cell growth factor (VEGF) variant polypeptide may include amino acid residues as shown in FIG. 1A, 1B, 1C, and/or FIG. 6, among others, and include therefore isoforms of VEGF which contain an insertion in the heparin binding domain (HBD) at amino acids 18-41 (see FIG. 1C and FIG. 6) as well as those naturally occurring VEGF isoforms which each contain the variants in the heparin binding domain at the locations noted (see FIG. 1B). The VEGF variant polypeptide has, in the case of molecules described in FIG. 1B, at least one of the arginines at amino acids 13, 14 and/or 49 substituted with a negatively charged (e.g., acidic) amino acid residue, in some embodiments glutamic acid, or in the case of molecules described in FIG. 1C, at least one of the arginines at amino acid 31, 32 and/or 67; 37, 38 and/or 73; or 54, 55 and/or 90 substituted with a negatively charged (e.g., acidic) amino acid residue, in some embodiments glutamic acid.

The present invention also includes methods for treating a disease characterized by pathological angiogenesis, comprising administering to a patient in need thereof a pharmaceutically effective amount of a vascular endothelial cell growth factor (VEGF) variant polypeptide comprising a variant C-terminal heparin binding domain, and a native receptor tyrosine kinase binding domain, wherein said variant polypeptide has one or more amino acid alternations from a native VEGF polypeptide, wherein said variant polypeptide binds heparin at a lower affinity than and/or repels heparin as compared to said native VEGF. In one embodiment the polypeptide comprises a variant C-terminal heparin domain.

As used herein, an "effective amount" or a "pharmaceutically effective amount" is an amount sufficient to effect beneficial or desired clinical results. An effective amount can be administered in one or more administrations. For purposes of this invention, an effective amount of a VEGF variant is an amount that is sufficient to palliate, ameliorate, stabilize, reverse, slow or delay the progression of the disease state. In a preferred embodiment of the invention, the "effective amount" is defined as an amount capable of reducing the growth and/or remodeling of collateral blood vessels.

As used herein, "treatment" or "treating" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

In one embodiment, the affinity of the variant polypeptide for both VEGFR-1 (FLT-1) and VEGFR-2 (KDR/FLK-1) is substantially maintained in comparison to said native VEGF. In another embodiment, the variant polypeptide antagonizes KDR signal activation.

"Angiogenesis" is defined the promotion of the growth of new blood capillary vessels from existing endothelium. The contribution of elevated VEGF expression and its signaling pathway has been associated to pathological angiogenesis in virtually all carcinomas studied as well as neovascular ophthalmic diseases such as age-related macular degeneration and retinopathy. Polypeptides of the invention may be used to treat these disorders.

A disease characterized by pathological angiogenesis includes any disease or pathological process that is characterized by undesirable growth of new blood vessels in the body. Thus the polypeptides of the present invention may be used to treat pathological conditions such as tumor growth and in non-neoplastic diseases involving abnormal neovascularization. Accordingly examples of disorders characterized by pathological angiogenesis that are treatable by the present invention include, but are not limited to, neoplastic diseases, including but not limited to solid tumors, and excessive angiogenesis, involving, for example, vascularization and/or inflammation, such as atherosclerosis, rheumatoid arthritis (RA), neovascular glaucoma, proliferative retinopathy including proliferative diabetic retinopathy, macular degeneration, age-related macular degeneration, wet macular degeneration, hemangiomas, angiofibromas, and psoriasis. Other non-limiting examples of non-neoplastic angiogenic disease are retinopathy of prematurity (retrolental fibroplastic), corneal graft rejection, insulin-dependent diabetes mellitus, multiple sclerosis, myasthenia gravis, Crohn's disease, autoimmune nephritis, primary biliary cirrhosis, acute pancreatitis, allograph rejection, allergic inflammation, contact dermatitis and delayed hypersensitivity reactions, inflammatory bowel disease, septic shock, osteoporosis, osteoarthritis, cognition defects induced by neuronal inflammation, Osler-Weber syndrome, restinosis, and fungal, parasitic and viral infections, including cytomegaloviral infections. Conditions or diseases to which persistent or uncontrolled angiogenesis contribute have been termed angiogenic dependent or angiogenic associated diseases.

Neoplastic diseases to treat include cancer and/or metastatic cancer. A partial list of cancers to treat with polypeptides of the present invention include solid tumors, such as carcinomas, derived from epithelial cells, including breast, prostate, lung, pancreas, and colon; sarcomas, arising from connective tissue, such as bone cancer; lymphoma and leukemias, which arise from hematopoietic cells; germ cell tumors such as testicular cancer and ovarian cancer, and blastomas, derived from precursor or embryonic tissue. Such tumors include benign or malignant tumors (e.g. renal, liver, kidney, bladder, breast, gastric, ovarian, colorectal, prostate, pancreatic, lung, vulval, thyroid, hepatic carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic and immunologic disorders.

The identification of such disease is well within the ability and knowledge of one skilled in the art. For example, human individuals who are either suffering from a clinically significant neoplastic or angiogenic disease or who are at risk of developing clinically significant symptoms are suitable for administration of the present VEGF receptor antibodies. A clinician skilled in the art can readily determine, for example, by the use of clinical tests, physical examination and medical/family history, if an individual is a candidate for such treatment.

Compositions of the present invention may also be useful as molecular imaging agents for VEGFR. Compositions of the present invention may be used to bind to the target molecule (VEGFR, for example) and labeled with a moiety that renders it visible to a particular imaging modality. Labels in common use include radionuclides, fluorescent molecules, and paramagnetic ions, as well as nanoparticles, liposomes and microbubbles, all of which are known in the art. For example, molecular imaging agents including compositions of the present invention may be useful in diagnosing and/or evaluating a disease characterized by pathological angiogenesis as described herein.

Variant polypeptides of the present invention useful in the methods of the present invention include the following polypeptides: a polypeptide comprising SEQ ID NO:25 wherein the amino acid of at least one of positions 149, 150, and 185 of SEQ ID NO:25 is an acidic amino acid, a polypeptide comprising SEQ ID NO:26 wherein the amino acid of at least one of positions 123, 124, and 159 of SEQ ID NO:26 is an acidic amino acid, and a polypeptide comprising SEQ ID NO:27 wherein the amino acid of at least one of positions 13, 14, and 49 of SEQ ID NO:27 is an acidic amino acid.

Variant polypeptides of the present invention useful in the methods of the present invention also include: a polypeptide comprising SEQ ID NO:25 wherein the amino acid at positions 149, 150, and 185 of SEQ ID NO:25 is an acidic amino acid, a polypeptide comprising SEQ ID NO:26 wherein the amino acid at positions 123, 124, and 159 of SEQ ID NO:26 is an acidic amino acid, and a polypeptide comprising SEQ ID NO:27 wherein the amino acid at positions 13, 14, and 49 of SEQ ID NO:27 is an acidic amino acid.

Variant polypeptides of the present invention useful in the methods of the present invention also include: a polypeptide comprising SEQ ID NO:6, a polypeptide comprising SEQ ID NO:7, a polypeptide comprising SEQ ID NO:8, a polypeptide comprising SEQ ID NO:10, a polypeptide comprising SEQ ID NO:11, a polypeptide comprising SEQ ID NO:12, a polypeptide comprising SEQ ID NO:14, a polypeptide comprising SEQ ID NO:15, a polypeptide comprising SEQ ID NO:16, a polypeptide comprising SEQ ID NO:18, a polypeptide comprising SEQ ID NO:19, a polypeptide comprising SEQ ID NO:20, a polypeptide comprising SEQ ID NO:22, a polypeptide comprising SEQ ID NO:23, or a polypeptide comprising SEQ ID NO:24.

In addition to the alterations at amino acid positions as described herein, the VEGF variants of the present invention may contain further amino acid alterations, including substitutions and/or insertions and/or deletions in any other region of the VEGF molecule, including the N- and C-terminal regions. Preferably, these substitutions will be "conservative" substitutions and do not alter the structure or function of the resultant polypeptides based on either the native VEGF 165 polypeptides of the present invention or the variant VEGF 165 polypeptides of the present invention. The VEGF variants of the present invention show at least about 75%, at least about 80%, at least about 85%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, amino acid sequence identity with a polypeptide of the present invention. Such polypeptides include SEQ ID NO:2, SEQ ID NO:3, SEQ ID NO:4, SEQ ID NO:25, SEQ ID NO:26, SEQ ID NO:27, SEQ ID NO:6, SEQ ID NO:7, SEQ ID NO:8, SEQ ID NO:10, SEQ ID NO:11, SEQ ID NO:12, SEQ ID NO:14, SEQ ID NO:15, SEQ ID NO:16, SEQ ID NO:18, SEQ ID NO:19, SEQ ID NO:20, SEQ ID NO:22, SEQ ID NO:23, or SEQ ID NO:24. Such polypeptides also include VEGF189 variant polypeptides of the present invention and VEGF isoform variant polypeptides which show at least about 75%, at least about 80%, at least about 85%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, amino acid sequence identity with a polypeptide comprising SEQ ID NO:34, SEQ ID NO:35, SEQ ID NO:36, SEQ ID NO:37, SEQ ID NO:38, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68 and/or SEQ ID NO:69, and/or variants of each as described herein.

An example of VEGF variants of the present invention which may contain further amino acid alterations, including substitutions and/or insertions and/or deletions in any other region of the VEGF molecule, including the N- and C-terminal region can be seen in FIG. 1A. FIG. 1A, shows orthologs of human VEGF165 which correspond to SEQ ID NO: 39 through SEQ ID NO: 46. SEQ ID NO: 39 through SEQ ID NO: 46 are the native amino acid sequence of orthologs of human VEGF165. These orthologs of human VEGF165 also contain the critical basic amino acid, arginine (Arg/R) residues which may be substituted with an acidic amino acid, for example glutamic acid (Glu/E) to obtain the variants of the present invention. In particular, FIG. 1A shows orthologs of human VEGF165 to *F. catus* (cat), where substitutions of an acidic amino acid in SEQ ID NO:39 could occur in at least one of R147, R148 and R183 of SEQ ID NO: 39 which correspond to R121, R122, and R157 when considering only the part of SEQ ID NO:39 which reflects the amino acid sequence of the mature VEGF molecule; *C. familiaris* (dog), where substitutions of an acidic amino acid in SEQ ID NO:40 could occur in at least one of R148, R149 and R184 of SEQ ID NO: 40 which correspond to R122, R123, and R158 when considering only the part of SEQ ID NO:40 which reflects the amino acid sequence of the mature VEGF molecule; *B. Taurus* (bovine), where substitutions of an acidic amino acid in SEQ ID NO:41 could occur in at least one of R148, R149 and R184 of SEQ ID NO: 41 which correspond to R122, R123, and R158 when considering only the part of SEQ ID NO:41 which reflects the amino acid sequence of the mature VEGF molecule; *E. caballus* (horse), *R. norvegicus* (rat), where substitutions of an acidic amino acid in SEQ ID NO:42 or SEQ ID NO:43 could occur in at least one of R148, R149 and R184 of SEQ ID NO: 42 or SEQ ID NO: 43 which correspond to R122, R123, and R158 when considering only the part of of SEQ ID NO:42 or SEQ ID NO:43 which reflects the amino acid sequence of the mature VEGF molecule; *M. musculus* (mouse), where substitutions of an acidic amino acid in SEQ ID NO:44 could occur in at least one of R148, R149 and R184 of SEQ ID NO: 44 which correspond to R122, R123, and R158 when considering only the part of SEQ ID NO:44 which reflects the amino acid sequence of the mature VEGF molecule; *G. gallus* (chicken), where substitutions of an acidic amino acid in SEQ ID NO:45 could occur in at least one of R150, R151 and R186 of SEQ ID NO: 45 which correspond to R124, R125, and R160 when considering only the part of SEQ ID NO:45 which reflects the amino acid sequence of the mature VEGF molecule; and *X. laevis* (frog), where substitutions of an acidic amino acid in SEQ ID NO:46 could occur in at least one of K150, R153 and R188 of SEQ ID NO: 46 which correspond to K124, R127, and R162 when considering only the part of SEQ ID NO:46 which reflects the amino acid sequence of the mature VEGF molecule. Examples of 3S variants of these VEGF orthologs would be R121E/R122E/R157E (*F. Catus*), R122E/R123E/R159E (*C. familiaris, B. Taurus, E. caballus, R. Norvegicus, M. Musculus*, R124E/R125E/R160E (*G. gallus*) and K124E/R127E/R162E (*X. laevis*). These orthologs have high sequence identity with human VEGF variants of the present invention and should be considered to be an example of VEGF variants of the present invention.

Variant polypeptides of the present invention include polypeptides which show at least about 75%, at least about 80%, at least about 85%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, amino acid sequence identity with a polypeptide comprising SEQ ID NO:39, SEQ ID NO:40, SEQ ID NO:41, SEQ ID NO:42, SEQ ID NO:43, SEQ ID NO:44, SEQ ID NO:45, and/or SEQ ID NO:46, and/or variants of each as described herein.

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

In one embodiment, the present invention includes a polynucleotide that encodes a variant polypeptide of the present invention. In one embodiment, the present invention includes a polynucleotide that encodes a polypeptide comprising SEQ ID NO:25 wherein the amino acid of at least one of positions 149, 150, and 185 of SEQ ID NO:25 is an acidic amino acid. The present invention also includes a polynucleotide that encodes a polypeptide comprising SEQ ID NO:26 wherein the amino acid of at least one of positions 123, 124, and 159 of SEQ ID NO:26 is an acidic amino acid. The present invention also includes a polynucleotide that encodes a polypeptide comprising SEQ ID NO:27 wherein the amino acid of at least one of positions 13, 14, and 49 of SEQ ID NO:27 is an acidic amino acid.

In other embodiments of the present invention includes a polynucleotide that encodes a polypeptide comprising SEQ ID NO:6, a polynucleotide that encodes a polypeptide comprising SEQ ID NO:7, a polynucleotide that encodes a polypeptide comprising SEQ ID NO:8, a polynucleotide that encodes a polypeptide comprising SEQ ID NO:10, a polynucleotide that encodes a polypeptide comprising SEQ ID NO:11, a polynucleotide that encodes a polypeptide comprising SEQ ID NO:12, a polynucleotide that encodes a polypeptide comprising SEQ ID NO:14, a polynucleotide that encodes a polypeptide comprising SEQ ID NO:15, a polynucleotide that encodes a polypeptide comprising SEQ ID NO:16, a polynucleotide that encodes a polypeptide comprising SEQ ID NO:18, a polynucleotide that encodes a polypeptide comprising SEQ ID NO:19, a polynucleotide that encodes a polypeptide comprising SEQ ID NO:20, a polynucleotide that encodes a polypeptide comprising SEQ ID NO:22, a polynucleotide that encodes a polypeptide comprising SEQ ID NO:23, or a polynucleotide that encodes a polypeptide comprising SEQ ID NO:24.

In another embodiment, the polynucleotide includes a polynucleotide comprising SEQ ID NO:5, SEQ ID NO:9, SEQ ID NO:13, SEQ ID NO:17, or SEQ ID NO:21. In another embodiment, the polynucleotide includes a polynucleotide comprising SEQ ID NO:28, SEQ ID NO:29, SEQ ID NO:30, SEQ ID NO:31, SEQ ID NO:32, or SEQ ID NO:33.

The polynucleotides that encode VEGF variants of the present invention may contain further nucleotide alterations, including substitutions and/or insertions and/or deletions in any other region of the VEGF molecule, including the N- and C-terminal coding regions. Preferably, these substitutions will be "conservative" substitutions and do not alter the amino acid residues of the resultant polypeptides. In some embodiments, an amino acid residue may be altered, but the change is a change to another amino acid that is similar to the one replaced and the structure and/or function of the resultant polypeptides will remain, based on either the native VEGF 165 polypeptides of the present invention or the variant VEGF 165 polypeptides of the present invention. The polynucleotides of the present invention which encode VEGF variants of the present invention show at least about 75%, at least about 80%, at least about 85%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity with a polynucleotide which can be any of the following: a polynucleotide that encodes a polypeptide comprising SEQ ID NO:6, a polynucleotide that encodes a polypeptide comprising SEQ ID NO:7, a polynucleotide that encodes a polypeptide comprising SEQ ID NO:8, a polynucleotide that encodes a polypeptide comprising SEQ ID NO:10, a polynucleotide that encodes a polypeptide comprising SEQ ID NO:11, a polynucleotide that encodes a polypeptide comprising SEQ ID NO:12, a polynucleotide that encodes a polypeptide comprising SEQ ID NO:14, a polynucleotide that encodes a polypeptide comprising SEQ ID NO:15, a polynucleotide that encodes a polypeptide comprising SEQ ID NO:16, a polynucleotide that encodes a polypeptide comprising SEQ ID NO:18, a polynucleotide that encodes a polypeptide comprising SEQ ID NO:19, a polynucleotide that encodes a polypeptide comprising SEQ ID NO:20, a polynucleotide that encodes a polypeptide comprising SEQ ID NO:22, a polynucleotide that encodes a polypeptide comprising SEQ ID NO:23, or a polynucleotide that encodes a polypeptide comprising SEQ ID NO:14; in another embodiment the polynucleotide includes a polynucleotide that includes SEQ ID NO:1, SEQ ID NO:5, SEQ ID NO:9, SEQ ID NO:13, SEQ ID NO:17, or SEQ ID NO:21; in another embodiment, the polynucleotide includes a polynucleotide comprising SEQ ID NO:28, SEQ ID NO:29, SEQ ID NO:30, SEQ ID NO:31, SEQ ID NO:32, or SEQ ID NO:33.

In another embodiment, the polynucleotides of the present invention which encode VEGF189 variants of the present invention show at least about 75%, at least about 80%, at least about 85%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity with a polynucleotide a polynucleotide that encodes a polypeptide comprising SEQ ID NO:34, a polynucleotide that encodes a polypeptide comprising SEQ ID NO:35, a polynucleotide that encodes a polypeptide comprising SEQ ID NO:36, a polynucleotide that encodes a polypeptide comprising SEQ ID NO:37, or a polynucleotide that encodes a polypeptide comprising SEQ ID NO:38.

In another embodiment, the polynucleotides of the present invention which encode other VEGF variants of the present invention show at least about 75%, at least about 80%, at least about 85%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity with a polynucleotide a polynucleotide that encodes a polypeptide comprising SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68 and/or SEQ ID NO:69, and/or variants of each as described herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

VEGF variants with more than one amino acid substitution may be generated in one of several ways. If the amino acids are located close together in the polypeptide chain, they may be mutated simultaneously, using one oligonucleotide that codes for all of the desired amino acid substitutions. If, however, the amino acids are located some distance from one another (e.g. separated by more than ten amino acids), it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant.

Amino acid sequence variants of the polypeptides of this invention (referred to in herein as the target polypeptide) are prepared by introducing appropriate nucleotide changes into the DNA encoding the target polypeptide, or by in vitro synthesis of the desired target polypeptide. Any combination of deletion, insertion, and substitution can be made to arrive at the final construct, provided that the final construct possesses the desired characteristics. The amino acid changes also may alter post-translational processes of the target polypeptide, such as changing the number or position of glycosylation sites, altering any membrane anchoring characteristics, and/or altering the intra-cellular location of the target polypeptide by inserting, deleting, or otherwise affecting any leader sequence of the native target polypeptide.

There are two principal variables in the construction of amino acid sequence variants: the location of the mutation site and the nature of the mutation. In general, the location and nature of the mutation chosen will depend upon the target polypeptide characteristic to be modified.

Amino acid sequence deletions of VEGF polypeptides of the present invention are generally not preferred, as maintaining the generally configuration of a polypeptide is believed to be desirable for its activity. Any deletions will be selected so as to preserve the structure.

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within the target polypeptide sequence) may range generally from about 1 to 10 residues, more preferably 1 to 5, most preferably 1 to 3. Examples of terminal insertions include the target polypeptide with an N-terminal methionyl residue, an artifact of the direct expression of target polypeptide in bacterial recombinant cell culture, and fusion of a heterologous N-terminal signal sequence to the N-terminus of the target polypeptide molecule to facilitate the secretion of the mature target polypeptide from recombinant host cells. Such signal sequences generally will be obtained from, and thus homologous to, the intended host cell species. Suitable sequences include STH or Ipp for *E. coli*, alpha factor for yeast, and viral signals such as herpes gD for mammalian cells. Other insertional variants of the target polypeptide include the fusion to the N- or C-terminus of the target polypeptide of immunogenic polypeptides, e.g., bacterial polypeptides such as beta-lactamase or an enzyme encoded by the *E. coli* trp locus, or yeast protein, and C-terminal fusions with proteins having a long half-life such as immunoglobulin constant regions (or other immunoglobulin regions), albumin, or ferritin.

DNA encoding amino acid sequence variants of the VEGF variants of the present invention is prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the target polypeptide. These techniques may utilize polypeptide nucleic acid (DNA or RNA), or nucleic acid complementary to the target polypeptide nucleic acid.

Oligonucleotide-mediated mutagenesis is one method for preparing substitution, deletion, and insertion variants of target polypeptide DNA. This technique is well known in the art as described by Adelman et al., DNA, 2: 183 (1983). Briefly, the target polypeptide DNA is altered by hybridizing an oligonucleotide encoding the desired mutation to a DNA template, where the template is the single-stranded form of a plasmid or bacteriophage containing the unaltered or native DNA sequence of the target polypeptide. After hybridization, a DNA polymerase is used to synthesize an entire second complementary strand of the template that will thus incorporate the oligonucleotide primer, and will code for the selected alteration in the target polypeptide DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (Proc. Natl. Acad. Sci. USA, 75: 5765 (1978)). Single-stranded DNA template may also be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase 1, is then added to synthesize the complementary strand of the template using the oligonucleotide as a primer for synthesis. A heteroduplex molecule is thus formed such that one strand of DNA encodes the mutated form of the target polypeptide, and the other strand (the original template) encodes the native, unaltered sequence of the target polypeptide. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

DNA encoding target polypeptide variants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for the template, an oligonucleotide encoding the first desired amino acid substitutions) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of target polypeptide. While the following discussion refers to DNA, it is understood that the technique also finds application with RNA. The PCR technique generally refers to the following procedure (see Erlich, supra, the chapter by R. Higuchi, p. 61-70): When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 μg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GENEAMP kits (obtained from Perkin-Elmer Cetus, Norwalk, Conn. and Emeryville, Calif.), and 25 pmole of each oligonucleotide primer, to a final volume of 50 μl. The reaction mixture is overlayed with 35 μl mineral oil. The reaction is denatured for 5 minutes at 100° C., placed briefly on ice, and then 1 μl *Thermus aquaticus* (Taq) DNA polymerase (5 units/μl, purchased from Perkin-Elmer Cetus, Norwalk, Conn. and Emeryville, Calif.) is added below the mineral oil layer. The reaction mixture is then inserted into a DNA Thermal Cycler (purchased from Perkin-Elmer Cetus) programmed as follows: 2 min at 55° C., then 30 sec. at 72° C., then 19 cycles of the following: 30 sec. at 94° C., 30 sec. at 55° C., and 30 sec. at 72° C. At the end of the program, the reaction vial is removed from the thermal cycler and the aqueous phase transferred to a new vial, extracted with phenol/chloroform (50:50:vol), and ethanol precipitated, and the DNA is recovered by standard procedures. This material is subsequently subjected to the appropriate treatments for insertion into a vector.

Another method for preparing variants, cassette mutagenesis, is based on the technique described by Wells et al. (Gene, 34: 315 (1985)). The starting material is the plasmid (or other vector) comprising the target polypeptide DNA to be mutated. The codon(s) in the target polypeptide DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the target polypeptide DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated target polypeptide DNA sequence.

In general, the signal sequence may be a component of the vector, or it may be a part of the target polypeptide DNA that is inserted into the vector.

The polypeptides of this invention may be expressed not only directly, but also as a fusion with a heterologous polypeptide, preferably a signal sequence or other polypeptide having a specific cleavage site at the N-terminus of the mature protein or polypeptide. In general, the signal sequence may be a component of the vector, or it may be a part of the target polypeptide DNA that is inserted into the vector. Included within the scope of this invention are target polypeptides with any native signal sequence deleted and replaced with a heterologous signal sequence. The heterologous signal sequence selected should be one that is recognized and processed (i.e. cleaved by a signal peptidase) by the host cell. For prokaryotic host cells that do not recognize and process the native target polypeptide signal sequence, the signal sequence is substituted by a prokaryotic signal sequence selected, for example, from the group of the alkaline phosphatase, penicillinase, Ipp, or heat-stable enterotoxin II leaders. For yeast secretion, the native target polypeptide signal sequence may be substituted by the yeast invertase, alpha factor, or acid phosphatase leaders. In mammalian cell expression the native signal sequence is satisfactory, although other mammalian signal sequences may be suitable.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

The present invention also relates to vectors comprising the polynucleotide molecules of the invention, as well as host cells transformed with such vectors. Any of the polynucleotide molecules of the invention may be joined to a vector, which generally includes a selectable marker and an origin of replication, for propagation in a host. Host cells are genetically engineered to express the polypeptides of the present invention. The vectors include DNA encoding any of the polypeptides described above or below, operably linked to suitable transcriptional or translational regulatory sequences, such as those derived from a mammalian, microbial, viral, or insect gene. Examples of regulatory sequences include transcriptional promoters, operators, or enhancers, mRNA ribosomal binding sites, and appropriate sequences which control transcription and translation. Nucleotide sequences are operably linked when the regulatory sequence functionally relates to the DNA encoding the target protein. Thus, a promoter nucleotide sequences is operably linked to polynucleotide of the present invention if the promoter nucleotide sequence directs the transcription of the polynucleotide of the present invention.

Selection of suitable vectors to be used for the cloning of polynucleotide molecules of the present invention will depend on the host cell in which the vector will be transformed, and, where applicable, the host cell from which the target polypeptide is to be expressed. Examples of vectors useful in the methods of the present invention include, but are not limited to, plasmids, bacteriophages, cosmids, retroviruses, and artificial chromosomes. Suitable host cells for expression of the polypeptides of the invention include prokaryotes, yeast, and higher eukaryotic cells.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of the target polypeptide DNA. However, the recovery of genomic DNA encoding the target polypeptide is more complex than that of an exogenously replicated vector because restriction enzyme digestion is required to excise the target polypeptide DNA.

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media, e.g. the gene encoding D-alanine racemase for Bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al., J. Molec. Appl. Genet., 1: 327 (1982)), mycophenolic acid (Mulligan et al., Science, 209: 1422 (1980)) or hygromycin (Sugden et al., Mol. Cell. Biol., 5: 410-413 (1985)). The three examples given above employ bacterial genes under eukaryotic control to convey resistance to the appropriate drug G418 or neomycin (geneticin), xgpt (mycophenolic acid), or hygromycin, respectively. Another example of suitable selectable markers for mammalian cells are those that enable the identification of cells competent to take up the target polypeptide nucleic acid, such as dihydrofolate reductase (DHFR) or thymidine kinase. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the target polypeptide. Amplification is the process by which genes in greater demand for the production of a protein critical for growth are reiterated in tandem within the chromosomes of successive generations of recombinant cells. Increased quantities of the target polypeptide are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, Proc. Natl. Acad. Sci. USA, 77: 4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the target polypeptide. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells (particularly wild-type hosts that contain endogenous DHFR) transformed or co-transformed with DNA sequences encoding the target polypeptide, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282: 39 (1979); Kingsman et al., Gene, 7: 141 (1979); or Tschemper et al., Gene, 10: 157 (1980)). The trp1 gene provides a selection marker for a mutant strain of yeast lacking the ability to grow in tryptophan, for example, ATCC No. 44076 or PEP4-1 (Jones, Genetics, 85: 12 (1977)). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

Expression and cloning vectors usually contain a promoter that is recognized by the host organism and is operably linked to the target polypeptide nucleic acid. Promoters are untranslated sequences located upstream (5') to the start codon of a structural gene (generally within about 100 to 1000 bp) that control the transcription and translation of a particular nucleic acid sequence, such as that encoding the target polypeptide, to which they are operably linked. Such promoters typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DNA encoding the target polypeptide by removing the promoter from the source DNA by restriction enzyme digestion and inserting the isolated promoter sequence into the vector. Both the native target polypeptide promoter sequence and many heterologous promoters may be used to direct amplification and/or expression of the target polypeptide DNA. However, heterologous promoters are preferred, as they generally permit greater transcription and higher yields of expressed target polypeptide as compared to the native target polypeptide promoter. Promoters suitable for use with prokaryotic hosts include the β-lactamase and lactose promoter systems (Chang et al., Nature, 275: 615 (1978); and Goeddel et al., Nature, 281: 544 (1979)), alkaline phosphatase, a tryptophan (trp) promoter system (Goeddel, Nucleic Acids Res., 8: 4057 (1980) and EP 36,776) and hybrid promoters such as the tac promoter (deBoer et al., Proc. Natl. Acad. Sci. USA, 80: 21-25 (1983)). However, other known bacterial promoters are suitable. Their nucleotide sequences have been published, thereby enabling a skilled worker operably to ligate them to DNA encoding the target polypeptide (Siebenlist et al., Cell, 20: 269 (1980)) using linkers or adaptors to supply any required restriction sites. Promoters for use in bacterial systems also generally will contain a Shine-Dalgarno (S.D.) sequence operably linked to the DNA encoding the target polypeptide.

Suitable promoting sequences for use with yeast hosts include the promoters for 3-phosphoglycerate kinase (Hitzeman et al., J. Biol. Chem., 255: 2073 (1980)) or other glycolytic enzymes (Hess et al., J. Adv. Enzyme Reg., 7: 149 (1968); and Holland, Biochemistry, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

Target polypeptide transcription from vectors in mammalian host cells is controlled by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat-shock promoters, and from the promoter normally associated with the target polypeptide sequence, provided such promoters are compatible with the host cell systems.

The early and late promoters of the SV40 virus are conveniently obtained as an SV40 restriction fragment that also contains the SV40 viral origin of replication. Fiers et al., Nature, 273:113 (1978); Mulligan and Berg, Science, 209: 1422-1427 (1980); Pavlakis et al., Proc. Natl. Acad. Sci. USA, 78: 7398-7402 (1981). The immediate early promoter of the human cytomegalovirus is conveniently obtained as a HindIII E restriction fragment. Greenaway et al., Gene, 18: 355-360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., Nature, 295: 503-508 (1982) on expressing cDNA encoding immune interferon in monkey cells; Reyes et al., Nature, 297: 598-601 (1982) on expression of human .beta.-interferon cDNA in mouse cells under the control of a thymidine kinase promoter from herpes simplex virus, Canaani and Berg, Proc. Natl. Acad. Sci. USA, 79: 5166-5170 (1982) on expression of the human interferon .beta.1 gene in cultured mouse and rabbit cells, and Gorman et al., Proc. Natl. Acad. Sci. USA, 79: 6777-6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

Transcription of DNA encoding the target polypeptide of this invention by higher eukaryotes is often increased by inserting an enhancer sequence into the vector. Enhancers are cis-acting elements of DNA, usually about from 10-300 bp, that act on a promoter to increase its transcription. Enhancers are relatively orientation and position independent having been found 5' (Laimins et al., Proc. Natl. Acad. Sci. USA, 78: 993 (1981)) and 3' (Lusky et al., Mol. Cell Bio., 3: 1108 (1983)) to the transcription unit, within an intron (Banerji et al., Cell, 33: 729 (1983)) as well as within the coding sequence itself (Osborne et al., Mol. Cell Bio., 4:1293 (1984)). Many enhancer sequences are now known from mammalian genes (globin, elastase, albumin, .alpha.-fetoprotein and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature, 297: 17-18 (1982) on enhancing elements for activation of eukaryotic promoters. The enhancer may be spliced into the vector at a position 5' or 3' to the target polypeptide DNA, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding the target polypeptide. The 3' untranslated regions also include transcription termination sites.

Construction of suitable vectors containing one or more of the above listed components the desired coding and control sequences employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., Nucleic Acids Res., 9: 309 (1981) or by the method of Maxam et al., Methods in Enzymology, 65: 499 (1980).

Particularly useful in the practice of this invention are expression vectors that provide for the transient expression in mammalian cells of DNA encoding the target polypeptide. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of the target polypeptide that have target polypeptide-like activity.

Other methods, vectors, and host cells suitable for adaptation to the synthesis of the target polypeptide in recombinant vertebrate cell culture are described in Gething et al., Nature, 293: 620-625 (1981); Mantei et al., Nature, 281: 40-46 (1979); Levinson et al.; EP 117,060; and EP 117,058. A particularly useful plasmid for mammalian cell culture expression of the target polypeptide is pRK5 (EP pub. no. 307,247) or pSVI6B.

Suitable host cells for cloning or expressing the vectors herein are the prokaryote, yeast, or higher eukaryote cells described above. Suitable prokaryotes include eubacteria, such as Gram-negative or Gram-positive organisms, for example, *E. coli,* Bacilli such as *B. subtilis, Pseudomonas* species such as *P. aeruginosa, Salmonella typhimurium*, or *Serratia marcescans*. One preferred *E. coli* cloning host is *E. coli* 294 (ATCC 31,446), although other strains such as *E. coli* B, *E. coli* 1776 (ATCC 31,537), and *E. coli* W3110 (ATCC 27,325) are suitable. These examples are illustrative rather than limiting. Preferably the host cell should secrete minimal amounts of proteolytic enzymes. Alternatively, in vitro methods of cloning, e.g. PCR or other nucleic acid polymerase reactions, are suitable.

In addition to prokaryotes, eukaryotic microbes such as filamentous fungi or yeast are suitable hosts for target polypeptide-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* (Beach and Nurse, Nature, 290: 140 (1981); EP 139,383 published May 2, 1985), *Kluyveromyces* hosts (U.S. Pat. No. 4,943,529) such as, e.g., *K. lactis* (Louvencourt et al., J. Bacteriol., 737 (1983)), *K. fragilis, K. bulgaricus, K. thermotolerans*, and *K. marxianus, yarrowia* (EP 402,226), *Pichia pastoris* (EP 183,070; Sreekrishna et al., J. Basic Microbiol., 28: 265-278 (1988)), *Candida, Trichoderma reesia* (EP 244,234), *Neurospora crassa* (Case et al., Proc. Natl. Acad. Sci. USA, 76: 5259-5263 (1979)), and filamentous fungi such as, e.g, *Neurospora, Penicillium, Tolypocladium* (WO 91/00357 published Jan. 10, 1991), and *Aspergillus* hosts such as *A. nidulans* (Ballance et al., Biochem. Biophys. Res. Commun., 112: 284-289 (1983); Tilburn et al., Gene, 26: 205-221 (1983); Yelton et al., Proc. Natl. Acad. Sci. USA, 81: 1470-1474 (1984)) and *A. niger* (Kelly and Hynes, EMBO J. 4: 475-479 (1985)).

Suitable host cells for the expression of target polypeptide are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified. See, e.g., Luckow et al., Bio/Technology 6: 47-55 (1988); Miller et al., in Genetic Engineering, Setlow, J. K. et al., eds., Vol. 8 (Plenum Publishing, 1986), pp. 277-279; and Maeda et al., Nature, 315: 592-594 (1985). A variety of such viral strains are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the target polypeptide DNA. During incubation of the plant cell culture with *A. tumefaciens*, the DNA encoding target polypeptide is transferred to the plant cell host such that it is transfected, and will, under appropriate conditions, express the target polypeptide DNA. In addition, regulatory and signal sequences compatible with plant cells are available, such as the nopaline synthase promoter and polyadenylation signal sequences. Depicker et al., J. Mol. Appl. Gen., 1: 561 (1982). In addition, DNA segments isolated from the upstream region of the T-DNA 780 gene are capable of activating or increasing transcription levels of plant-expressible genes in recombinant DNA-containing plant tissue. See EP 321,196 published Jun. 21, 1989.

However, interest has been greatest in vertebrate cells, and propagation of vertebrate cells in culture (tissue culture) has become a routine procedure in recent years (Tissue Culture, Academic Press, Kruse and Patterson, editors (1973)). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol., 36: 59 (1977)); baby hamster kidney cells (BHK, ATCC CCL 10); Chinese hamster ovary cells/-DHFR (CHO, Urlaub and Chasin, Proc. Natl. Acad. Sci. USA, 77: 4216 (1980)); mouse sertoli cells (TM4, Mather, Biol. Reprod., 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383: 44-68 (1982)); MRC 5 cells; FS4 cells; and a human hepatoma cell line (Hep G2). Preferred host cells are human embryonic kidney 293 and Chinese hamster ovary cells.

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, CaPO-.sub.4 and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium tumefaciens* is used for transformation of certain plant cells, as described by Shaw et al., Gene, 23: 315 (1983) and WO 89/05859 published Jun. 29, 1989. For mammalian cells without such cell walls, the calcium phosphate precipitation method described in sections 16.30-16.37 of Sambrook et al, supra, is preferred. General aspects of mammalian cell host system transformations have been described by Axel in U.S. Pat. No. 4,399,216 issued Aug. 16, 1983. Transformations into yeast are typically carried out according to the method of Van Solingen et al., J. Bact., 130: 946 (1977) and Hsiao et al., Proc. Natl. Acad. Sci. (USA), 76: 3829 (1979). However, other methods for introducing DNA into cells such as by nuclear injection, electroporation, or protoplast fusion may also be used.

Prokaryotic cells used to produce the target polypeptide of this invention are cultured in suitable media as described generally in Sambrook et al., supra.

The mammalian host cells used to produce the target polypeptide of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham and Wallace, Meth. Enz., 58: 44 (1979), Barnes and Sato, Anal. Biochem., 102: 255 (1980), U.S. Pat. Nos. 4,767,704; 4,657,866; 4,927,762; or 4,560,655; WO 90/03430; WO 87/00195; U.S. Pat. No. Re. 30,985, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

It is further envisioned that the target polypeptides of this invention may be produced by homologous recombination, or with recombinant production methods utilizing control elements introduced into cells already containing DNA encoding the target polypeptide currently in use in the field. For example, a powerful promoter/enhancer element, a suppressor, or an exogenous transcription modulatory element is inserted in the genome of the intended host cell in proximity and orientation sufficient to influence the transcription of DNA encoding the desired target polypeptide. The control element does not encode the target polypeptide of this invention, but the DNA is present in the host cell genome. One next screens for cells making the target polypeptide of this invention, or increased or decreased levels of expression, as desired.

Gene amplification and/or expression may be measured in a sample directly, for example, by conventional Southern blotting, northern blotting to quantitate the transcription of mRNA (Thomas, Proc. Natl. Acad. Sci. USA, 77: 5201-5205 (1980)), dot blotting (DNA analysis), or in situ hybridization, using an appropriately labeled probe, based on the sequences provided herein. Various labels may be employed, most commonly radioisotopes, particularly .sup.32 P. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., Am. J. Clin. Path., 75: 734-738 (1980).

Antibodies useful for immunohistochemical staining and/or assay of sample fluids may be either monoclonal or polyclonal, and may be prepared in any mammal. Conveniently, the antibodies may be prepared against a native target polypeptide or against a synthetic peptide based on the DNA sequences provided herein as described further in Section 4 below.

The target polypeptide preferably is recovered from the culture medium as a secreted polypeptide, although it also may be recovered from host cell lysates when directly expressed without a secretory signal.

When the target polypeptide is expressed in a recombinant cell other than one of human origin, the target polypeptide is completely free of proteins or polypeptides of human origin. However, it is necessary to purify the target polypeptide from recombinant cell proteins or polypeptides to obtain preparations that are substantially homogeneous as to the target polypeptide. As a first step, the culture medium or lysate is centrifuged to remove particulate cell debris. The membrane and soluble protein fractions are then separated. The target polypeptide may then be purified from the soluble protein fraction and from the membrane fraction of the culture lysate, depending on whether the target polypeptide is membrane bound. The following procedures are exemplary of suitable purification procedures: fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; and protein A Sepharose columns to remove contaminants such as IgG.

Target polypeptide variants in which residues have been deleted, inserted or substituted are recovered in the same fashion, taking account of any substantial changes in properties occasioned by the variation. For example, preparation of a target polypeptide fusion with another protein or polypeptide, e.g. a bacterial or viral antigen, facilitates purification; an immunoaffinity column containing antibody to the antigen (or containing antigen, where the target polypeptide is an antibody) can be used to adsorb the fusion. Immunoaffinity columns such as a rabbit polyclonal anti-target polypeptide column can be employed to absorb the target polypeptide variant by binding it to at least one remaining immune epitope. A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native target polypeptide may require modification to account for changes in the character of the target polypeptide or its variants upon expression in recombinant cell culture.

The VEGF variants of the present invention can be administered for therapeutic treatments to a patient suffering from a tumor or angiogenesis associated pathologic condition in an amount sufficient to prevent, inhibit, or reduce the progression of the tumor or pathologic condition. Progression includes, e.g, the growth, invasiveness, metastases and/or recurrence of the tumor or pathologic condition. An amount adequate to accomplish this is defined as a therapeutically effective dose. Amounts effective for this use will depend upon the severity of the disease and the general state of the patient's own immune system. Dosing schedules will also vary with the disease state and status of the patient, and will typically range from a single bolus dosage or continuous infusion to multiple administrations per day (e.g., every 4-6 hours), or as indicated by the treating physician and the patient's condition. It should be noted, however, that the present invention is not limited to any particular dose.

In an embodiment of the invention, VEGF variants of the present invention can be administered in combination with one or more other antineoplastic agents. Any suitable antineoplastic agent can be used, such as a chemotherapeutic agent or radiation. When the antineoplastic agent is radiation, the source of the radiation can be either external (external beam radiation therapy—EBRT) or internal (brachytherapy—BT) to the patient being treated. VEGF variant polypeptides of the present invention can be administered together with a antineoplastic agent which includes a chemotherapeutic agent. A "chemotherapeutic agent" is a chemical compound useful in the treatment of cancer. Examples of chemotherapeutic agents include alkylating agents such as thiotepa and cyclosphosphamide, alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nirnustine, ranimustine; antibiotics such as the enediyne antibiotics (e.g. calicheamicin, especially calicheamicin, dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimeterxate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifene, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In one embodiment, the combination therapy can include combinations with VEGF variants of the present invention and, such as, for example, IFL (5-fluorouracil, leucovorin and irinotecan), FOLFOX (5-fluorouracil, leukovorin and oxaliplatin); XELOX (capecitabine and oxaliplatin), paclitaxel, docetaxel, (capecitabine, taxane, and antracycline), (carboplatin and paclitaxel), (cisplatin and gemcitabine), erlotinib, interferon-2α, (carboplatin and paclitaxel), sunitinib, sorafenib, pazopanib, (vandefanib and paclitaxel), cetuximab, (oxaliplatin- or irinotecan-based chemotherapy and panitumumab), capecitabine, (capecitine or 5-fluorouracil and cisplatin), gemcitabine, (gemcitabine and erlotinib), (docetaxel and prednisone), prednisone, pemetrexed, (5-fluorouracil, leukovorin and irinotecan), (leukovorin and 5-fluorouracil), lomustine, bevacizumab, aflibercept, sunitinib, sorafenib, PTK787, semaxanib, axitinib, vandetanib, cediranib.

The dose of antineoplastic agent administered depends on numerous factors, including, for example, the type of agent, the type and severity tumor being treated and the route of administration of the agent. It should be emphasized, however, that the present invention is not limited to any particular dose.

Further, VEGF variants of the present invention may be administered with antibodies that neutralize other receptors involved in tumor growth or angiogenesis. One such receptor is EGFR. In an embodiment of the present invention, a VEGF variant of the present invention is used in combination with an EGFR antagonist. An EGFR antagonist can be an antibody that binds to EGFR or a ligand of EGFR and inhibits binding of EGFR to its ligand. Examples of EGFR antagonists that bind EGFR include, without limitation, biological molecules, such as antibodies (and functional equivalents thereof) specific for EGFR, and small molecules, such as synthetic kinase inhibitors that act directly on the cytoplasmic domain of EGFR. Other examples of growth factor receptors involved in tumorigenesis are the receptors for platelet-derived growth factor (PDGFR), insulin-like growth factor (IGFR), nerve growth factor (NGFR), and fibroblast growth factor (FGFR).

In an additional alternative embodiment, the VEGF variants of the present invention can be administered in combination with one or more suitable adjuvants, such as, for example, cytokines (IL-10 and IL-13, for example) or other immune stimulators. See, e.g., Larrivee et al., supra. It should be appreciated, however, that administration of only an anti-KDR antibody is sufficient to prevent, inhibit, or reduce the progression of the tumor in a therapeutically effective manner.

In a combination therapy, a VEGF variant of the present invention is administered before, during, or after commencing therapy with another agent, as well as any combination thereof, i.e., before and during, before and after, during and after, or before, during and after commencing the antineoplastic agent therapy. For example, a VEGF variant of the present invention may be administered between 1 and 30 days, preferably 3 and 20 days, more preferably between 5 and 12 days before commencing radiation therapy.

It is noted that VEGF variants of the present invention can be administered as a conjugate, which binds specifically to the receptor and delivers a toxic, lethal payload following ligand-toxin internalization.

The present invention also includes kits for inhibiting tumor growth and/or angiogenesis comprising a therapeutically effective amount of one or more of a VEGF variant of the present invention. The kits can further contain any suitable antagonist of, for example, another growth factor receptor involved in tumorigenesis or angiogenesis (e.g., EGFR, PDGFR, IGFR, NGFR, FGFR, etc, as described above). Alternatively, or in addition, the kits of the present invention can further comprise an antineoplastic agent. Examples of suitable antineoplastic agents in the context of the present invention have been described herein. The kits of the present invention can further comprise an adjuvant, examples have also been described above.

It is understood that VEGF variants of the present invention, where used in a mammal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the binding proteins. The compositions of the injection may, as is well known in the art, be formulated so as to provide quick, sustained or delayed release of the active ingredient after administration to the mammal.

Pharmaceutical compositions of the present invention can comprise a polynucleotide encoding a VEGF variant herein, or, alternatively, pharmaceutical compositions can comprise the VEGF variant itself.

Suitable forms, in part, depend upon the use or the route of entry, for example oral, transdermal, inhalation, or by injection. For example, pharmacological agents or compositions injected into the blood stream should be soluble. Other factors are known in the art, and include considerations such as toxicity and forms that prevent the agent or composition from exerting its effect.

Compositions comprising a VEGF variant or a polynucleotide encoding a VEGF variant can also be formulated as pharmaceutically acceptable salts (e.g., acid addition salts) and/or complexes thereof. Pharmaceutically acceptable salts are non-toxic at the concentration at which they are administered. Pharmaceutically acceptable salts include acid addition salts such as those containing sulfate, hydrochloride, phosphate, sulfonate, sulfamate, sulfate, acetate, citrate, lactate, tartrate, methanesulfonate, ethanesulfonate, benzenesulfonate, p-toluenesulfonate, cyclohexylsulfonyl, cyclohexylsulfamate and quinate. Pharmaceutically acceptable salts can be obtained from acids such as hydrochloric acid, sulfuric acid, phosphoric acid, sulfonic acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including, but not limited to, intravenous, intra-arterial, intraperitoneal, intrapericardial, intracoronary, subcutaneous, and intramuscular, oral, topical, or transmucosal.

The desired isotonicity of the compositions can be accomplished using sodium chloride or other pharmaceutically acceptable agents such as dextrose, boric acid, sodium tartrate, propylene glycol, polyols (such as mannitol and sorbitol), or other inorganic or organic solutes.

Pharmaceutical compositions comprising a VEGF variant or a polynucleotide encoding a VEGF variant can be formulated for a variety of modes of administration, including systemic and topical or localized administration. Techniques and formulations generally may be found in Remington's Pharmaceutical Sciences, 18th Edition, Mack Publishing Co., Easton, Pa. 1990. See, also, Wang and Hanson "Parenteral Formulations of Proteins and Peptides: Stability and Stabilizers", Journal of Parenteral Science and Technology, Technical Report No. 10, Supp. 42-2S (1988). A suitable administration format can best be determined by a medical practitioner for each patient individually.

For systemic administration, injection is preferred, e.g., intramuscular, intravenous, intra-arterial, intracoronary, intrapericardial, intraperitoneal, subcutaneous, intrathecal, or intracerebrovascular. For injection, the compounds of the invention are formulated in liquid solutions, preferably in physiologically compatible buffers such as Hank's solution or Ringer's solution. Alternatively, the compounds of the invention are formulated in one or more excipients (e.g., propylene glycol) that are generally accepted as safe as defined by USP standards. They can, for example, be suspended in an inert oil, suitably a vegetable oil such as sesame, peanut, olive oil, or other acceptable carrier. Preferably, they are suspended in an aqueous carrier, for example, in an isotonic buffer solution at pH of about 5.6 to 7.4. These compositions can be sterilized by conventional sterilization techniques, or can be sterile filtered. The compositions can contain pharmaceutically acceptable auxiliary substances as required to approximate physiological conditions, such as pH buffering agents. Useful buffers include for example, sodium acetate/acetic acid buffers. A form of repository or "depot" slow release preparation can be used so that therapeutically effective amounts of the preparation are delivered into the bloodstream over many hours or days following transdermal injection or delivery. In addition, the compounds can be formulated in solid form and redissolved or suspended immediately prior to use. Lyophilized forms are also included.

Alternatively, the compounds can be administered orally. For oral administration, the compounds are formulated into conventional oral dosage forms such as capsules, tablets and tonics.

Systemic administration can also be by transmucosal or transdermal. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be, for example, through nasal sprays or using suppositories.

For administration by inhalation, usually inhalable dry power compositions or aerosol compositions are used, where the size of the particles or droplets is selected to ensure deposition of the active ingredient in the desired part of the respiratory tract, e.g. throat, upper respiratory tract or lungs. Inhalable compositions and devices for their administration are well known in the art. For example, devices for the delivery of aerosol medications for inspiration are known. One such device is a metered dose inhaler that delivers the same dosage of medication to the patient upon each actuation of the device. Metered dose inhalers typically include a canister containing a reservoir of medication and propellant under pressure and a fixed volume metered dose chamber. The canister is inserted into a receptacle in a body or base having a mouthpiece or nosepiece for delivering medication to the patient. The patient uses the device by manually pressing the canister into the body to close a filling valve and capture a metered dose of medication inside the chamber and to open a release valve which releases the captured, fixed volume of medication in the dose chamber to the atmosphere as an aerosol mist. Simultaneously, the patient inhales through the mouthpiece to entrain the mist into the airway. The patient then releases the canister so that the release valve closes and the filling valve opens to refill the dose chamber for the next administration of medication. See, for example, U.S. Pat. No. 4,896,832 and a product available from 3M Healthcare known as Aerosol Sheathed Actuator and Cap.

For topical administration, the compounds of the invention are formulated into ointments, salves, gels, or creams, as is generally known in the art. If desired, solutions of the above compositions can be thickened with a thickening agent such as methyl cellulose. They can be prepared in emulsified form, either water in oil or oil in water. Any of a wide variety of pharmaceutically acceptable emulsifying agents can be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components can be mixed simply in a blender or other standard device to produce a concentrated mixture which can then be adjusted to the final concentration and viscosity by the addition of water or thickening agent and possibly a buffer to control pH or an additional solute to control tonicity.

The amounts of various compounds for use in the methods of the invention to be administered can be determined by standard procedures. Generally, a therapeutically effective amount is between about 100 mg/kg and $10^{-12}$ mg/kg depending on the age and size of the patient, and the disease or disorder associated with the patient.

The present invention also provides delivery vehicles suitable for delivery of a polynucleotide encoding a VEGF variant into cells (whether in vivo, ex vivo, or in vitro). Generally, a polynucleotide encoding a VEGF variant will be operably linked to a promoter and a heterologous polynucleotide. A polynucleotide encoding a VEGF variant can be contained within a cloning or expression vector, using methods well known in the art, or within a viral vector. These vectors (especially expression vectors) can in turn be manipulated to assume any of a number of forms, which may, for example, facilitate delivery to and/or entry into a target cell. Delivery of the polynucleotide constructs of the invention to eukaryotic cells, particularly to mammalian cells, more particularly to distal tubule cells of the kidney, can be accomplished by any suitable art-known method. Delivery can be accomplished in vivo, ex vivo, or in vitro.

The invention provides methods and compositions for transferring such expression constructs into cells, especially in vivo for performing the methods of the present invention. It is also an object of the invention to provide compositions for the treatment (including prevention) of the conditions listed above by providing for the prevention or repair of the underlying vascular injury and/or the associated damage to non-vascular tissues. Delivery vehicles suitable for incorporation of a polynucleotide encoding a VEGF variant of the present invention for introduction into a host cell include non-viral vehicles and viral vectors. Verma and Somia (1997) Nature 389:239-242.

A wide variety of non-viral vehicles for delivery of a polynucleotide encoding a VEGF variant are known in the art and are encompassed in the present invention. A polynucleotide encoding a VEGF variant can be delivered to a cell as naked DNA (U.S. Pat. No. 5,692,622; WO 97/40163). Alternatively, a polynucleotide encoding a VEGF variant can be delivered to a cell associated in a variety of ways with a variety of substances (forms of delivery) including, but not limited to cationic lipids; biocompatible polymers, including natural polymers and synthetic polymers; lipoproteins; polypeptides; polysaccharides; lipopolysaccharides; artificial viral envelopes; metal particles; and bacteria. A delivery vehicle can be a microparticle. Mixtures or conjugates of these various substances can also be used as delivery vehicles. A polynucleotide encoding a VEGF variant can be associated non-covalently or covalently with these various forms of delivery. Liposomes can be targeted to a particular cell type, e.g., to a glomerular epithelial cell.

Viral vectors include, but are not limited to, DNA viral vectors such as those based on adenoviruses, herpes simplex virus, poxviruses such as vaccinia virus, and parvoviruses, including adeno-associated virus; and RNA viral vectors, including, but not limited to, the retroviral vectors. Retroviral vectors include murine leukemia virus, and lentiviruses such as human immunodeficiency virus. Naldini et al. (1996) Science 272:263-267.

Non-viral delivery vehicles comprising a polynucleotide encoding a VEGF variant can be introduced into host cells and/or target cells by any method known in the art, such as transfection by the calcium phosphate coprecipitation technique; electroporation; electropermeabilization; liposome-mediated transfection; ballistic transfection; biolistic processes including microparticle bombardment, jet injection, and needle and syringe injection; or by microinjection. Numerous methods of transfection are known to the skilled worker in the field.

Viral delivery vehicles can be introduced into cells by infection. Alternatively, viral vehicles can be incorporated into any of the non-viral delivery vehicles described above for delivery into cells. For example, viral vectors can be mixed with cationic lipids (Hodgson and Solaiman (1996) Nature Biotechnol. 14:339-342); or lamellar liposomes (Wilson et al. (1977) Proc. Natl. Acad. Sci. USA 74:3471; and Faller et al. (1984) J. Virol. 49:269). For in vivo delivery, the delivery vehicle(s) can be introduced into an individual by any of a number of methods, each of which is familiar in the art.

The present invention also includes a method for creating a polypeptide capable of inhibiting angiogenesis by: (1) providing a native VEGF comprising a C-terminal heparin binding domain and (2) modifying said native VEGF to form a variant VEGF of the invention.

Further details of the present invention will be apparent from the following non-limiting Examples. All references cited throughout the specification, including the Examples, are hereby expressly incorporated by reference.

EXAMPLES

Example 1

293/KDR cells were from SibTech and maintained as described (Backer et al., 2005). Heparin and biotin heparin was from Sigma. Purified HS tetramer and HS oligomer were from Neoparin.

The following Gateway Entry (Invitrogen) clones (all 3.8 kB) were generated: Hs.VEGF165 Wild Type sequence (SEQ ID NO:28); Hs.VEGF165 R149E (SEQ ID NO:33); Hs.VEGF165 R150E (SEQ ID NO:32); Hs.VEGF165 R185E (SEQ ID NO:31); Hs.VEGF165 R149E/R150E (SEQ ID NO:30); Hs.VEGF165 R149E/R150E/R185E (SEQ ID NO:29); all plasmids were grown in *E. coli* with spectrinomycin (100 ug/ml) for plasmid selection.

Plasmids for mammalian expression of VEGF165 wild type and mutant forms (all 6.1 kB) under the control of a CMV/T7 promoter were generated from Gateway Entry clones (Invitrogen). All possess ampicillin resistance used for plasmid propagation (100 ug/ml), neomycin (G418) resistance for mammalian selection (500-800 ug/ml, depending on target cell type), the native VEGF165 signal peptide sequence and G418 resistance. The following clones of VEGF were generated for mammalian expression: Hs.VEGF165 wild type sequence; Hs.VEGF165 Wild Type sequence (SEQ ID NO:28); Hs.VEGF165 R149E (SEQ ID NO:33); Hs.VEGF165 R150E (SEQ ID NO:32); Hs.VEGF165 R185E (SEQ ID NO:31); Hs.VEGF165 R149E/R150E (SEQ ID NO:30); Hs.VEGF165 R149E/R150E/R185E (SEQ ID NO:29).

For proliferation assays, 293/KDR derived cell lines ($5\times10^4$ cellsper well) were seeded in 6-well culture plates in quadruplicate. Cell number per well was measured after 2, 3, 4, and 5 days of growth by removing cells with trypsin, collecting via centrifugation and counting suspended cells in triplicate in a Cellometer Automatic Cell Counter (Nexcelom Bioscience, Lawrence, Mass.). Purified recombinant VEGF-A protein used as an external standard quantitation as VEGF mass per mass total extracted cell protein. KDR autophosphorylation in cell lysates was measured similarly; cultured cells were serum-deprived for 48 h, where noted cells were stimulated for 20 min with WT or 3S VEGF-A alone or in combination at the indicated concentrations, then extracted with ice cold buffer containing non-ionic detergent, protease and phosphatase inhibitors. Cleared extracts were applied to assay plates and processing per the manufacturer's instructions.

KDR and VEGF content in cell lysates, tissue extracts and conditioned media was determined using two-site electrochemiluminescent immunoassays developed by Meso Scale Discovery (Gaithersburg, Md.) for use with the Meso Scale Discovery (MSD) SectorImager 2400 plate reader.

KDR autophosphorylation in cell lysates or tumor tissue extracts was measured similarly but included parallel detection with anti-receptor antibodies and specific anti-phosphoreceptor antibodies or 4G10 (Millipore). Cell lysates were prepared as described previously (Athauda et al., 2006). Tumor tissue non-ionic detergent extracts were prepared using the same buffer but accompanied by physical disruption in a Mini-BeadBeater-8 (Glen Mills Inc.) and clearing by centrifugation prior to immunoassay.

Ligand binding assays were also developed on the electrochemiluminescent platform. KDR-Ig ectodomain saturation binding to VEGF165 WT or 3S proteins that had been captured using a non-neutralizing monoclonal VEGF antibody; bound KDR was detected using tagged anti-KDR. All measurements were made on triplicate samples. GraphPad Prism software version 5.0 was used for statistical analyses and determination of $K_D$ and $IC_{50}$ values.

Example 2

To determine whether 3S VEGF 165 (SEQ ID NO:7) retained mitogenic activity relative to the WT VEGF 165 sequence, we stably transfected HEK293 cells that had been engineered to express $2.5\times10^6$ VEGFR2 per cell (293/KDR; 22) with expression plasmids encoding vector alone, WT or 3S VEGF 165. Ectopic VEGF protein production by transfectants was measured using a two-site immunoassay with a detection limit of 37.5 attomoles/25 ul (1.5 pM) VEGF (FIG. 3).

Among marker selected mass cultures, WT transfectants produced ~1.0 ng/ml/24 h VEGF165 protein in conditioned media, 3S transfectants produced ~2.5 ng/ml/24 h, and VEGF protein was undetectable in the empty vector control media (FIG. 4A, white bars). The VEGF content in low volume detergent extracts from the same cells was proportionally higher, as expected (FIG. 4A, gray bars). Molecular mass and antibody recognition of VEGF165 3S protein in conditioned media were indistinguishable from WT (FIG. 4B). Saturation binding of VEGF165 3S to KDR in vitro (FIG. 4C, squares; KD ~19 pM) was also equivalent to VEGF165 WT binding (FIG. 4C, circles; KD ~23 pM) and consistent with published steady-state binding affinity values (Ferrara, 2004).

KDR tyrosyl phosphorylation in each cell line was measured after 24 h of serum deprivation (FIG. 4D). The basal KDR phosphorylation level in empty vector transfectants (FIG. 4D, white bar) was indistinguishable from that of the parental cell line (not shown) or the 3S transfectants (FIG. 4D, dark gray bar). In contrast, WT transfectant basal KDR phosphorylation level was 4-fold higher than control or 3S (FIG. 4D, light gray bar; $p<0.001$). The KDR autophosphorylation level of the vector transfectant after 20 min exposure to exogenously added VEGF165 protein (2.5 nM) is shown for reference (FIG. 4D, black bar). Consistent with the levels of KDR activation among the transfectants, significant differences in cell proliferation rate in culture were observed from day 3 onward: WT transfectants (FIG. 4E, squares) grew significantly faster than the vector control (FIG. 4E, circles) or 3S transfectants (FIG. 4E, triangles; $p<0.001$ between WT and control or WT and 3S for days 3-5). These results suggested that the WT transfectants had acquired autocrine VEGF signaling, but not the 3S transfectants, even though 3S protein production was more than twice that of WT. In soft agar colony formation assays, empty vector transfectants and S3 transfectants grew modestly, if at all (FIG. 4F, left and middle panels), whereas VEGF165 WT transfectants grew robustly (FIG. 4F, right panel). All of these results indicated loss of signaling by VEGF165 3S, despite normal KDR binding.

Competitive antagonism of VEGF165 WT signaling by VEGF165 3S protein was assessed in intact cells and in vivo (FIG. 5). Concentrated conditioned media harvested from the 3S transfectants was added to 293/KDR cells in the presence of purified VEGF165 WT protein and phospho-KDR levels were measured (FIGS. 5A and B). Since the conditioned media could contain other inhibitors of KDR activation, VEGF165 3S was selectively removed from the media by immunodepletion with anti-VEGF antibody. A mock-immunodepletion was performed in parallel using a non-specific antibody and the VEGF165 3S content of the anti-VEGF and mock-immunodepleted media was measured (FIG. 5A). VEGF 3S levels in non-immunodepleted and mock immunodepleted media were nearly identical (1.93 and 1.89 ng/mg total cell protein, respectively; FIG. 5A, white bars), while immunodepletion with anti-VEGF removed 95% of the 3S protein (0.096 ng/mg total cell protein; FIG. 5A, gray bar). VEGF protein was not detected in media from empty vector transfectants before or after immunodepletion (FIG. 5A, right). KDR autophosphorylation stimulated by purified VEGF165 protein (10 ng/ml) in serum-deprived 293/KDR cells (FIG. 5B, 100%) was inhibited modestly by VEGF-immunodepleted media (FIG. 5B, circles), but mock-immunodepleted media showed significant, dose-dependent inhibition, with >80% inhibition by media containing 2.5-fold molar excess VEGF 3S protein (FIG. 5B, triangles). In soft agar colony formation assays, the robust anchorage independent growth of 293/KDR cells stably transfected with VEGF165 WT (FIG. 5C, upper left panel) was inhibited in a dose-dependent manner by pazopanib, a VEGFR-selective antagonist (FIG. 5C, middle and right upper panels), providing additional evidence that colony formation was driven by autocrine VEGF/KDR signaling. VEGF165 3S protein added at 0.06, 0.15 and 0.6 nM also resulted in significant, dose-dependent inhibition (FIG. 5C, lower panels).

To test whether VEGF165 3S protein could antagonize KDR-driven tumorigenicity in mice, animals were implanted subcutaneously with VEGF165 WT transfected 293/KDR cells ($3\times10^6$ per animal), with the same number of VEGF165 3S transfected cells, or with a suspension containing $1.5\times10^6$ cells of each line. Additional control groups received the empty vector 293/KDR cells ($3\times10^6$ per animal) or the empty vector cells combined with VEGF WT transfectants at $1.5\times10^6$ cells each. The latter group indicated the growth rate of tumors arising from $1.5\times10^6$ VEGF WT transfectants in the presence of "neutral" cells providing the same initial mass; a growth rate below this threshold in the group implanted with VEGF WT+VEGF 3S transfectants could be attributed to inhibition of VEGF WT-driven tumor growth by VEGF165 3S. Indeed, VEGF WT transfected 293/KDR cells formed tumors fastest (FIG. 5D, squares), whereas VEGF 3S transfectants did not form tumors prior to study termination (FIG. 5D, inverted triangles), and animals implanted with the WT+3S cell mix (FIG. 5D, diamonds) formed tumors at a significantly lower rate than the control WT+empty vector group (FIG. 5D, triangles) throughout the study ($p<0.05$). The ability of the parental cell line (FIG. 5D, circles) to form tumors in mice, in the absence of robust soft agar colony formation, suggests that endogenous murine VEGF drove tumorigenesis in a paracrine manner, and the failure of the 3S transfectants (FIG. 5D, triangles) to form tumors suggests antagonism of this pathway. The animal studies also indicate that autocrine VEGF/KDR-driven tumorigenesis by the VEGF165 WT transfectants (FIG. 5D, squares), potentially enhanced by murine VEGF, was competitively antagonized by secreted VEGF165 3S protein in animals receiving the WT+3S transfectant cell mix (FIG. 5D, diamonds).

Example 3

For proliferation assays, 293/KDR derived cell lines were seeded in 6-well culture plates in quadruplicate. Cell number per well was measured at regular intervals removal of adherent cells and counting in a Cellometer Automatic Cell Counter (Nexcelom Bioscience). Assays for colony formation in soft agar were performed as described (Castagnino et al., 2000).

SoftAgar Colony Formation Assays for colony formation in soft agar (representative of anchorage independent growth) were performed and quantitated as described previously. Briefly, U87 MG cells and U87 MG cells transfected with a plasmid encoding NK1 60/62/73 were suspended in 0.5% Seaplaque agarose (1×105 cells) in growth medium in duplicate 60 mm dishes. Cell colonies were visualized after staining with p-iodotetrazolium violet by brightfield microscopy using an Olympus inverted microscope. Digital images were acquired and recorded using a CCD video camera and IP Lab software. Consistent with prior results, 293/KDR cells stably transfected with an expression plasmid for WT VEGF165 displayed robust anchorage independent growth. Treatment with pazopanib, a VEGFR-selective competitive antagonist of ATP binding every other day at 0.3 and 3.0 nM over two weeks resulted in substantial and dose-dependent inhibition of colony formation, providing additional evidence that it was primarily driven by autocrine VEGF/KDR signaling. Treatment with 3S VEGF protein at 0.06, 0.15, and 0.6 nM also resulted in substantial and dose-dependent inhibition, consistent with the observed inhibition of KDR kinase activation.

Example 4

All experiments involving animals were performed in accordance with NIH Guidelines for Care and Use of Laboratory Animals using approved protocols. 293/KDR cells stably transfected with VEGF WT or 3S expression plasmids, or empty vector, were injected subcutaneously into SCID/Beige mice (Taconic, Inc.; $3\times10^6$ cells per animal total as indicated in the text, 5 mice/group) and tumor volumes were measured at regular intervals as described previously (Giubellino et al., 2007). Statistical analysis and curve fitting for all animal studies were performed using GraphPad Prism software version 5.0.

To test whether 3S VEGF could antagonize KDR-driven tumorigenicity in mice, groups of animals (n=5) were implanted subcutaneously with WT VEFG transfected 293/KDR cells ($3\times10^6$ per animal), with the same number of 3S VEGF transfected cells, or with a suspension containing half the number of cells of each type. Additional control groups received the empty vector 293/KDR cells ($3\times10^6$ per animal) or the empty vector cells combined with WT VEGF transfectants at $1.5\times10^6$ cells each. The latter group indicted the growth rate of tumors arising from $1.5\times10^6$ WT VEGF transfectants in the presence of "neutral" cells providing the same initial mass; a growth rate below this threshold in the group implanted with WT VEGF+3S VEGF transfectants could be attributed to inhibition by 3S VEGF. Indeed, WT VEGF transfected 293/KDR cells formed tumors fastest, 3S VEGF transfectants tumors grew most slowly, and animals implanted with the WT VEGF+ 3S VEGF transfectant mixture formed tumors at a significantly lower rate that the control WT VEGF+empty vector group throughout the study (paired two-tailed t test P=0.0108, t=4.497, df=4). These results strongly suggest that autocrine VEGF/KDR-driven tumorigenesis by the WT VEFG transfectants was competitively antagonized by secreted 3S VEGF protein. Together with our prior results with 3S HGF/NK1, the current work reinforces the theory that receptor occupancy combined with disruption of ternary HS binding may constitute an effective general strategy for antagonizing signaling by HS binding growth factors.

Example 5

The possibility that VEGF 3S had lost biological activity due to loss of its dimeric tertiary structure was investigated by SDS-PAGE and immunoblot analysis. We found that, like VEGF165 WT, VEGF 3S dimers and monomers of expected mass were detected under non-reducing and reducing conditions, respectively (FIG. 7). FIG. 7 shows VEGF165 3S (VEGF 3S; left) and VEGF165 WT (VEGF WT; middle) proteins in 24 h conditioned media prepared from 293/KDR transfectants, and purified recombinant VEGF165 protein (VEGF 4 ng; right), after SDS-PAGE under non-reducing (NR) and reducing (R) conditions and immunoblotting with anti-VEGF. Migration of molecular mass standards (kDa) is indicated by arrows. In addition to evidence already present in the application, these results strengthen the likelihood that changes engineered to the VEGF HS binding domain did not affect its tertiary structure.

As anticipated, found that heparin promoted clustering of VEGF165 WT, but not of VEGF165 3S (FIG. 8). FIG. 8 shows heparin-Sepharose mediated clustering of VEGF165 WT and VEGF165 3S analyzed by SDS-PAGE and immunodetection with anti-VEGF antibody. VEGF165 WT (left) or VEGF165 3S (right) conditioned media contained VEGF dimers (44 kDa) in both supernatant (super) and Heparin-Sepharose (HS beads) samples only in the presence of BS3. An 80 kDa complex consistent with tetrameric VEGF (and higher mass species of indeterminant copy number) was observed only in VEGF165 WT conditioned media in the presence of heparin (4th lane from left) and not in VEGF165 3S conditioned media (4th lane from the right). These findings further support the mechanism of action of VEGF 3S as antagonism of HS binding to the VEGF/VEGFR complex leading to instability of ligand/receptor/HS complexes and consequent disruption of downstream signaling.

Analysis of the spectrum of VEGF 3S antagonism showed that VEGF165 3S inhibited placenta growth factor (P1GF)-induced Akt activation (phospho-Akt/total Akt) in EA.hy 926 cells, which express VEGFR1 and R2, with potency similar to pazopanib (FIG. 9A). In contrast, VEGF 3S did not block Akt activation induced by VEGF-D in SCC-25 cells, which express VEGFR1, R2 and R3 (FIG. 9B, C). Thus the pattern of VEGF 3S inhibition followed the pattern of VEGF-A binding to VEGFR1 and R2, but not homodimers of VEGFR3, as anticipated. FIG. 9(A) shows dose dependent inhibition of VEGF-or P1GF-induced Akt activation (phospho Akt/total Akt) in EA.hy 926 cells. VEGF 3s blocked Akt activation by VEGF-A (dark circles) or P1GF (squares). VEGF 2S blocked Akt activation by VEGF-A (dark circles) or P1GF (squares) with potency similar to pazopanib (triangles and inverted triangles, respectively). FIG. 9(B) shows dose-dependent Akt activation (phosphor-Akt/total Akt) was measured by electrochemilumnescent two-site immunoassays in detergent extracts prepared from intact, serum deprived SCC-25 squamous cell carcinoma cells stimulated with VEGF165 (10-1000 pM) or VEGFD (100-10,000 pM) for 15 minutes at 37 degrees C. SCC-25 cells express all three VEGFRs. FIG. 9(C) shows VEGF165 3S antagonism of Akt activation by VEGF-A (at 100 pM) but not VEGF-D (at 1000 pM). These results suggest that VEGF165 3S antagonism follows the pattern of VEGF-A binding as anticipated: VEGF-A binding to VEGFR1 and R2 should be antagonized, whereas VEGF-D binding to VEGFR3 homodimers should not be affected.

VEGF165 3S antagonism was found to be independent of NRP1-VEGF-A protein-protein interaction. NRP1 binds to the VEGF-A HS binding domain primarily at R165 and secondarily at K147, E152 and E155, i.e., to a surface opposite that of HS. Crosslinking studies further showed that VEGF165 WT and VEGF165 3S bound similarly to NRP1 in vitro (FIG. 10A). Functionally, VEGF165 3S antagonized VEGF signaling similarly in 293/KDR derived cells, which lack NRP1 (FIG. 10B, lanes 4-6), and in EA.hy 926 cells which are NRP1 positive (FIG. 10B, lane 2).

In FIG. 10(A) Covalent affinity crosslinking analysis of NRP1 binding to VEGF165 WT and VEGF165 3S. Purified recombinant NRP1-Fc (Sino Biologics) was added as indicated (−NRP1 or +NRP1) to 24 h conditioned media from vector transfected 293/KDR cells(left lanes), 293/KDR/VEGF 3S transfectants (middle lanes), or 293/KDR/VEGF WT transfectants (right lanes) in the absence (−) or presence (+) of the crosslinking reagent BS3 (Thermo Fisher Pierce). Samples were resolved by SDS-PAGE under reducing conditions, transferred to PVDF and immunodetected with anti-Fc antibody (top panel; Thermo Fisher Pierce) or anti-VEGF (lower panels; R&D Systems). A 160 kDa band, consistent with a 1:1 complex of NRP1-Fc and VEGF dimer, was detected by both antibodies specifically in the presence of NRP1-Fc in media from 293/KDR/VEGF 3S transfectants and 293/KDR/VEGF WT transfectants but not the vector control. Another band of approximately 250 kDa was observed with the same pattern; the stoichiometry of this complex is indeterminant. Monomeric (22 kDa) is present in all lanes where VEGF media was added, and serves as a loading control. Dimeric VEGF (44 kDa) is captured from both 293/KDR/VEGF 3S media and 293/KDR/VEGF WT media only in the presence of BS3 in the reducing SDS-PAGE conditions used.

FIG. 10(B) The relative abundance of NRPI protein (upper panel) in PC3 prostate adenocarcinoma cells (lane 1), EA.hy 926 cells (lane 2), HEK293 cells (lane 3), 293/KDR vector transfected cells (lane 4), 293/KDR/VEGF165 WT cells (lane 5) and 293/KDR/VEGF165 3S cells (lane 6), determined by SDS-PAGE and immunoblotting with anti-NRPI (Cell Signaling). The bottom panel shows a GAPDH immunoblot of the same samples as a loading control.

Experimental Procedures

Reagents and Cell Culture: Purified VEGF proteins and antibodies for VEGF165 and CD44 were from R&D Systems, ABR Affinity Bioreagent and Santa Cruz Biotech. Pazopanib was from Tocris. Heparin and biotin heparin were from Sigma; HS tetramer and oligomer were from Neoparin. The cell lines 184B5, U87 MG, SK-LMS-1, B16, PC3M, EA.hy 926 and SCC-25 were cultured as described (Athauda et al., 2006; Giubellino et al., 2007; Lalla et al., 2003). 293/KDR cells from SibTech and maintained as described (Backer et al., 2005). Transfection reagents were from Amaxa Biosystems.

Plasmids for VEGF165: Plasmids for mammalian expression of VEGF165 WT (R123, R124 and R159) and VEGF165 3S (R123E/R124E/R159E) under the control of a CMV promoter were generated from Gateway Entry clones (Invitrogen) and possess the native VEGF165 signal peptide sequence and G418 resistance.

Immunoassays: KDR and VEGF content in cell lysates, tissue extracts and conditioned media was determined using 2-site electrochemiluminescent immunoassays developed for use with the Meso Scale Discovery (MSD) SectorImager 2400 plate reader (Gaithersburg, Md.). KDR activation in cell lysates or tumor tissue extracts included parallel detection with anti-receptor antibodies and specific anti-phosphoreceptor antibodies or 4G10 (Millipore). Cell lysates were prepared similarly for analysis of activated (phospho-) Akt, and total Akt using immunoassays from MSD. All measurements were made on triplicate samples. GraphPad Prism software version 5.0 was used for all statistical analyses: protein content values determined by 2-site immunoassay were interpolated from standard curves by nonlinear regression analysis (4 parameter logistic equation); saturation and competitive binding curves were fit after determination of specific binding and assuming a one site binding model.

Covalent Affinity Crosslinking: Assays. Heparin-mediated clustering of VEGF165 WT and VEGF165 3S was investigated using concentrated conditioned media from 293/KDR/VEGF165 WT or 293/KDR/VEGF165 3S transfectants incubated at 40 C for 16 h in the presence of Heparin Sepharose 6 Fast Flow (GE Healthcare). Heparin Sepharose beads were used as both a source of heparin and to efficiently capture heparin-clustered VEGF from the conditioned media after crosslinking. Samples were then incubated with or without BS3 at room temperature for 1 h. After pelleting the beads by brief centrifugation, samples were obtained from the supernatants for SDS-PAGE and immunoblot analysis. The beads were then washed by five centrifugation/resuspension cycles in PBS, and bound proteins were eluted with boiling SDS-PAGE sample buffer. Supernatant and bead-captured samples were then resolved by SDS-PAGE under reducing conditions, transferred to PVDF and immunodetected with anti-VEGF antibody.

The invention claimed is:

1. A method for treating a disease characterized by pathological angiogenesis, comprising administering to a patient in need thereof a pharmaceutically effective amount of a vascular endothelial cell growth factor (VEGF) variant polypeptide having the ability to antagonize VEGF mediated angiogenesis and comprising (1) a polypeptide comprising a polypeptide selected from the group consisting of SEQ ID NO:25 wherein the amino acid at positions 149, 150, and 185 of SEQ NO:25 is glutamic acid or aspartic acid, SEQ ID NO:26 wherein the amino acid at positions 123, 124, and 159 of SEQ ID NO:26 is glutamic acid or aspartic acid, or (2) a polypeptide comprising a polypeptide having at least 95% identity to a polypeptide of (1) and having the identified amino acid substitutions of (1).

2. The method of claim 1 wherein the affinity of the variant polypeptide for both VEGFR-1 (FLT-1) and VEGFR-2 (KDR/FLK-1) is substantially maintained in comparison to said native VEGF.

3. The method of claim 1, wherein the variant polypeptide is selected from the group consisting of: (1) a polypeptide comprising a polypeptide selected from the group consisting of SEQ ID NO:6, SEQ ID NO:7, and (2) a polypeptide having at least 95% identity to a polypeptide of (1) and having the identified R to E substitutions of (1).

4. The method of claim 1, wherein the variant polypeptide comprises SEQ ID NO:7.

5. The method of claim 1, wherein the disease characterized by pathological angiogenesis is cancer, macular degeneration, or diabetic retinopathy.

6. The method of claim 5, wherein the cancer is a metastatic cancer.

* * * * *